(12) United States Patent
Ignon et al.

(10) Patent No.: US 11,241,357 B2
(45) Date of Patent: Feb. 8, 2022

(54) DEVICES, SYSTEMS AND METHODS FOR PROMOTING HAIR GROWTH

(71) Applicant: EDGE SYSTEMS LLC, Signal Hill, CA (US)

(72) Inventors: Roger Ignon, Redondo Beach, CA (US); Ed F. Nicolas, Signal Hill, CA (US); William Cohen, Los Alamitos, CA (US)

(73) Assignee: Edge Systems LLC, Long Beach, CA (US)

( * ) Notice: Subject to any disclaimer, the term of this patent is extended or adjusted under 35 U.S.C. 154(b) by 0 days.

(21) Appl. No.: 15/204,939

(22) Filed: Jul. 7, 2016

(65) Prior Publication Data

US 2017/0036002 A1 Feb. 9, 2017

Related U.S. Application Data

(60) Provisional application No. 62/190,243, filed on Jul. 8, 2015, provisional application No. 62/320,476, filed on Apr. 9, 2016.

(51) Int. Cl.
*A61M 37/00* (2006.01)
*A61N 5/06* (2006.01)
(Continued)

(52) U.S. Cl.
CPC ............. *A61H 7/001* (2013.01); *A61H 7/005* (2013.01); *A61H 9/0007* (2013.01);
(Continued)

(58) Field of Classification Search
CPC .......... A61M 37/00; A61M 2037/0007; A61H 9/0007; A61H 9/0021; A61H 9/0028; A61H 9/005; A61H 9/0057; A61H 9/0091
See application file for complete search history.

(56) References Cited

U.S. PATENT DOCUMENTS

| | | |
|---|---|---|
| 1,651,585 A | 12/1927 | Clair |
| 2,608,032 A | 8/1952 | Garver |

(Continued)

FOREIGN PATENT DOCUMENTS

| | | |
|---|---|---|
| AT | 400 305 | 12/1995 |
| AU | 1 014 299 | 5/1999 |

(Continued)

OTHER PUBLICATIONS

International Search Report for related PCT Application (App. No. PCT/US2016/041340, dated Nov. 4, 2016).

(Continued)

*Primary Examiner* — Benjamin J Klein
(74) *Attorney, Agent, or Firm* — Knobbe, Martens, Olson & Bear, LLP

(57) ABSTRACT

According to some embodiments, a method of promoting hair growth or hair stimulation in a subject comprises applying vacuum or suction using a handpiece assembly along a targeted portion of the subject's skin surface where hair growth or hair stimulation is desired and providing at least one treatment material to said targeted portion of the subject's skin surface, wherein the application of vacuum or suction helps promote hair growth or stimulate hair.

19 Claims, 23 Drawing Sheets

(51) Int. Cl.
*A61H 7/00* (2006.01)
*A61H 9/00* (2006.01)
*A61H 15/00* (2006.01)
*A61H 15/02* (2006.01)
*A61N 1/32* (2006.01)
*A61H 23/02* (2006.01)

(52) U.S. Cl.
CPC ......... *A61H 9/0028* (2013.01); *A61H 9/0057* (2013.01); *A61H 9/0071* (2013.01); *A61H 15/0085* (2013.01); *A61H 15/02* (2013.01); *A61N 5/0617* (2013.01); *A61N 5/0625* (2013.01); *A61H 23/0245* (2013.01); *A61H 2015/0064* (2013.01); *A61H 2201/013* (2013.01); *A61H 2201/0207* (2013.01); *A61H 2201/0214* (2013.01); *A61H 2201/0228* (2013.01); *A61H 2201/0285* (2013.01); *A61H 2201/10* (2013.01); *A61H 2201/105* (2013.01); *A61H 2201/5082* (2013.01); *A61H 2205/021* (2013.01); *A61N 1/322* (2013.01); *A61N 1/325* (2013.01); *A61N 2005/0663* (2013.01)

(56) References Cited

U.S. PATENT DOCUMENTS

| | | | |
|---|---|---|---|
| 2,631,583 A | 3/1953 | Lavergne |
| 2,701,559 A | 2/1955 | Cooper |
| 2,712,823 A | 7/1955 | Kurtin |
| 2,867,214 A | 1/1959 | Wilson |
| 2,881,763 A | 4/1959 | Robbins |
| 2,921,585 A | 1/1960 | Schumann |
| 3,037,509 A | 6/1962 | Schutz |
| 3,085,573 A | 4/1963 | Meyer et al. |
| 3,214,869 A | 11/1965 | Stryker |
| 3,468,079 A | 9/1969 | Kaufman |
| 3,476,112 A | 11/1969 | Elstein |
| 3,481,677 A | 12/1969 | Abrahamson |
| 3,505,993 A | 4/1970 | Lewes et al. |
| 3,560,100 A | 2/1971 | Spatz |
| 3,574,239 A | 4/1971 | Sollerud |
| 3,715,838 A | 2/1973 | Young et al. |
| 3,865,352 A | 2/1975 | Nelson et al. |
| 3,866,264 A | 2/1975 | Engquist |
| 3,930,598 A | 1/1976 | Slagle |
| 3,948,265 A | 4/1976 | Al Ani |
| 3,964,212 A | 6/1976 | Karden |
| 3,968,789 A | 7/1976 | Simoncini |
| 3,977,084 A | 8/1976 | Sloan |
| 4,121,388 A | 10/1978 | Wilson |
| 4,155,721 A | 5/1979 | Fletcher |
| 4,170,821 A | 10/1979 | Booth |
| 4,182,329 A | 1/1980 | Smit et al. |
| 4,203,431 A | 5/1980 | Abura et al. |
| 4,216,233 A | 8/1980 | Stein |
| 4,225,254 A | 9/1980 | Holberg et al. |
| 4,289,158 A | 9/1981 | Nehring |
| 4,299,219 A | 11/1981 | Norris, Jr. |
| 4,342,522 A | 8/1982 | Mackles |
| 4,378,804 A | 4/1983 | Cortese |
| 4,500,222 A | 2/1985 | Clading-Boel |
| 4,560,373 A | 12/1985 | Sugino et al. |
| 4,646,480 A | 3/1987 | Williams |
| 4,646,482 A | 3/1987 | Chitjian |
| 4,655,743 A | 4/1987 | Hyde |
| 4,676,749 A | 6/1987 | Mabille |
| 4,706,676 A | 11/1987 | Peck |
| 4,718,467 A | 1/1988 | Di Gianfilippo et al. |
| 4,754,756 A | 7/1988 | Shelanski |
| 4,757,814 A | 7/1988 | Wang et al. |
| 4,764,362 A | 8/1988 | Barchas |
| 4,795,421 A | 1/1989 | Blasius, Jr. et al. |
| 4,811,734 A | 3/1989 | McGurk-Burleson et al. |
| 4,836,192 A | 6/1989 | Abbate |
| 4,875,287 A | 10/1989 | Creasy et al. |
| 4,886,078 A | 12/1989 | Shiftman |
| 4,887,994 A | 12/1989 | Bedford |
| 4,900,316 A | 2/1990 | Yamamoto |
| 4,917,086 A | 4/1990 | Feltovich et al. |
| 4,925,450 A | 5/1990 | Imonti et al. |
| 4,940,350 A | 7/1990 | Kim |
| 4,957,747 A | 9/1990 | Stiefel |
| 5,006,004 A | 4/1991 | Dirksing et al. |
| 5,006,339 A | 4/1991 | Bargery et al. |
| 5,012,797 A | 5/1991 | Liang et al. |
| 5,035,089 A | 7/1991 | Tillman et al. |
| 5,037,431 A | 8/1991 | Summers et al. |
| 5,037,432 A | 8/1991 | Molinari |
| 5,054,339 A | 10/1991 | Yacowitz |
| 5,100,412 A | 3/1992 | Rosso |
| 5,100,424 A | 3/1992 | Jang |
| 5,119,839 A | 6/1992 | Rudolph |
| 5,122,153 A | 6/1992 | Harrel |
| 5,171,215 A | 12/1992 | Flanagan |
| 5,192,269 A | 3/1993 | Poli et al. |
| 5,207,234 A | 5/1993 | Rosso |
| 5,222,956 A | 6/1993 | Waldron |
| 5,242,433 A | 9/1993 | Smith et al. |
| 5,254,109 A | 10/1993 | Smith et al. |
| 5,368,581 A | 11/1994 | Smith et al. |
| 5,387,215 A | 2/1995 | Fisher |
| 5,391,151 A | 2/1995 | Wilmot |
| 5,417,674 A | 5/1995 | Smith et al. |
| 5,419,772 A | 5/1995 | Teitz et al. |
| 5,441,490 A | 8/1995 | Svedman |
| 5,460,620 A | 10/1995 | Smith et al. |
| 5,470,323 A | 11/1995 | Smith et al. |
| 5,484,427 A | 1/1996 | Gibbons |
| 5,490,736 A | 2/1996 | Haber et al. |
| 5,512,044 A | 4/1996 | Duer |
| 5,562,642 A | 10/1996 | Smith et al. |
| 5,562,643 A | 10/1996 | Johnson |
| 5,611,687 A | 3/1997 | Wagner |
| 5,612,797 A | 3/1997 | Clarke |
| 5,674,235 A | 10/1997 | Parisi |
| 5,676,643 A | 10/1997 | Cann et al. |
| 5,676,648 A | 10/1997 | Henley |
| 5,683,971 A | 11/1997 | Rose et al. |
| 5,697,920 A | 12/1997 | Gibbons |
| 5,707,383 A | 1/1998 | Bays |
| 5,713,785 A | 2/1998 | Nishio |
| 5,735,833 A | 4/1998 | Olson |
| 5,759,185 A | 6/1998 | Grinberg |
| 5,762,640 A | 6/1998 | Kajiwara et al. |
| 5,779,519 A | 7/1998 | Oliver |
| 5,800,446 A | 9/1998 | Banuchi |
| 5,807,353 A | 9/1998 | Schmitz |
| 5,810,842 A | 9/1998 | Di Fiore et al. |
| 5,813,416 A | 9/1998 | Rudolph |
| 5,817,050 A | 10/1998 | Klein |
| 5,834,510 A | 11/1998 | Yu et al. |
| 5,846,215 A | 12/1998 | Zygmont |
| 5,848,998 A | 12/1998 | Marasco, Jr. |
| 5,857,995 A | 1/1999 | Thomas et al. |
| 5,861,142 A | 1/1999 | Schick |
| 5,873,881 A | 2/1999 | McEwen et al. |
| 5,879,323 A | 3/1999 | Henley |
| 5,882,201 A | 3/1999 | Salem |
| 5,885,260 A | 3/1999 | Mehl, Sr. et al. |
| 5,908,401 A | 6/1999 | Henley |
| 5,919,152 A | 7/1999 | Zygmont |
| 5,954,730 A | 9/1999 | Bernabei |
| 5,971,999 A | 10/1999 | Naldoni |
| 5,980,555 A | 11/1999 | Barbut et al. |
| 6,019,749 A | 2/2000 | Fields et al. |
| 6,023,639 A | 2/2000 | Hakky et al. |
| 6,024,733 A | 2/2000 | Eggers et al. |
| 6,027,402 A | 2/2000 | Oliver |
| 6,039,745 A | 3/2000 | Di Fiore et al. |
| 6,042,552 A | 3/2000 | Cornier |
| 6,080,165 A | 6/2000 | DeJacma |
| 6,080,166 A | 6/2000 | McEwen et al. |
| 6,090,085 A | 7/2000 | Mehl, Sr. et al. |

(56) References Cited

U.S. PATENT DOCUMENTS

| | | |
|---|---|---|
| 6,120,512 A | 9/2000 | Bernabei |
| 6,129,701 A | 10/2000 | Cimino |
| 6,136,008 A | 10/2000 | Becker et al. |
| 6,139,553 A | 10/2000 | Dotan |
| 6,139,554 A | 10/2000 | Karkar et al. |
| 6,142,155 A | 11/2000 | Rudolph |
| 6,149,634 A | 11/2000 | Bernabei |
| 6,159,226 A | 12/2000 | Kim |
| 6,162,218 A | 12/2000 | Elbrecht et al. |
| 6,162,232 A | 12/2000 | Shadduck |
| 6,165,059 A | 12/2000 | Parkin et al. |
| 6,183,451 B1 | 2/2001 | Mehl, Sr. et al. |
| 6,183,483 B1 | 2/2001 | Chang |
| 6,193,589 B1 | 2/2001 | Khalaj |
| 6,196,982 B1 | 3/2001 | Ball |
| 6,231,593 B1 | 5/2001 | Meserol |
| 6,235,039 B1 | 5/2001 | Parkin et al. |
| 6,238,275 B1 | 5/2001 | Metcalf et al. |
| 6,241,739 B1 | 6/2001 | Waldron |
| 6,264,666 B1 | 7/2001 | Coleman et al. |
| 6,277,128 B1 | 8/2001 | Muldner |
| 6,283,978 B1 | 9/2001 | Cheski et al. |
| 6,299,620 B1 | 10/2001 | Shadduck |
| 6,306,119 B1 | 10/2001 | Weber et al. |
| 6,306,147 B1 | 10/2001 | Bernabei et al. |
| 6,322,548 B1 | 11/2001 | Payne et al. |
| 6,322,568 B1 | 11/2001 | Bernabei et al. |
| 6,332,886 B1 | 12/2001 | Green et al. |
| 6,368,333 B2 | 4/2002 | Bernabei et al. |
| 6,387,103 B2 | 5/2002 | Shadduck |
| 6,401,289 B1 | 6/2002 | Herbert |
| 6,409,736 B1 | 6/2002 | Bernabei |
| 6,410,599 B1 | 6/2002 | Johnson |
| RE37,796 E | 7/2002 | Henley |
| 6,414,032 B1 | 7/2002 | Johnson |
| 6,420,431 B1 | 7/2002 | Johnson |
| 6,423,078 B1 | 7/2002 | Bays et al. |
| 6,423,750 B1 | 7/2002 | Johnson |
| 6,432,113 B1 | 8/2002 | Parkin et al. |
| 6,432,114 B1 | 8/2002 | Rosso |
| 6,471,712 B2 | 10/2002 | Burres |
| 6,477,410 B1 | 11/2002 | Henley et al. |
| 6,482,212 B1 | 11/2002 | Bernabei et al. |
| 6,488,646 B1 | 12/2002 | Zygmont |
| 6,494,856 B1 | 12/2002 | Zygmont |
| 6,500,183 B1 | 12/2002 | Waldron |
| 6,503,256 B2 | 1/2003 | Parkin et al. |
| 6,508,813 B1 | 1/2003 | Altshuler |
| 6,511,486 B2 | 1/2003 | Mercier et al. |
| 6,514,262 B1 | 2/2003 | Di Fiore et al. |
| 6,527,783 B1 | 3/2003 | Ignon |
| 6,535,761 B2 | 3/2003 | Bernabei |
| 6,537,242 B1 | 3/2003 | Palmer |
| 6,540,757 B1 | 4/2003 | Hruska et al. |
| 6,562,013 B1 | 5/2003 | Marasco, Jr. |
| 6,562,050 B1 | 5/2003 | Owen |
| 6,564,093 B1 | 5/2003 | Ostrow et al. |
| 6,565,535 B2 | 5/2003 | Zaias et al. |
| 6,582,442 B2 | 6/2003 | Simon et al. |
| 6,589,218 B2 | 7/2003 | Garcia |
| 6,592,595 B1 | 7/2003 | Mallett et al. |
| 6,626,445 B2 | 9/2003 | Murphy et al. |
| 6,629,927 B1 | 10/2003 | Mesaros et al. |
| 6,629,983 B1 | 10/2003 | Ignon |
| 6,641,591 B1 | 11/2003 | Shadduck |
| 6,645,184 B1 | 11/2003 | Zelickson et al. |
| 6,652,888 B2 | 11/2003 | Rhoades |
| 6,666,874 B2 | 12/2003 | Heitzmann et al. |
| 6,673,081 B1 | 1/2004 | Tavger et al. |
| 6,673,082 B2 | 1/2004 | Mallett et al. |
| D486,915 S | 2/2004 | Warschewske et al. |
| 6,685,853 B1 | 2/2004 | Angelopoulous et al. |
| 6,687,537 B2 | 2/2004 | Bernabei |
| 6,695,853 B2 | 2/2004 | Karasiuk |
| 6,735,470 B2 | 5/2004 | Henley et al. |
| 6,743,211 B1 | 6/2004 | Prausnitz et al. |
| 6,743,215 B2 | 6/2004 | Bernabei |
| 6,764,493 B1 | 7/2004 | Weber et al. |
| D496,101 S | 9/2004 | Davison |
| 6,800,083 B2 | 10/2004 | Hiblar et al. |
| 6,869,611 B1 | 3/2005 | Kligman et al. |
| 6,905,487 B2 | 6/2005 | Zimmerman |
| 6,911,031 B2 | 6/2005 | Muldner |
| 6,924,649 B2 | 8/2005 | Knoedgen |
| 6,926,681 B1 | 8/2005 | Ramey et al. |
| 6,938,805 B2 | 9/2005 | Brincat |
| 6,942,649 B2 | 9/2005 | Ignon et al. |
| 6,960,206 B2 | 11/2005 | Keane |
| 7,001,355 B2 | 2/2006 | Nunomura et al. |
| 7,004,933 B2 | 2/2006 | McDaniel |
| 7,044,938 B2 | 5/2006 | La Bianco et al. |
| 7,051,907 B2 | 5/2006 | Brincat |
| 7,052,503 B2 | 5/2006 | Bernabei |
| D522,360 S | 6/2006 | Caserta et al. |
| 7,069,073 B2 | 6/2006 | Henley et al. |
| 7,070,488 B2 | 7/2006 | Suissa et al. |
| 7,083,580 B2 | 8/2006 | Bernabei |
| 7,087,063 B2 | 8/2006 | Carson et al. |
| 7,094,252 B2 | 8/2006 | Koop |
| 7,115,275 B2 | 10/2006 | Clarot et al. |
| 7,135,011 B2 | 11/2006 | Powers et al. |
| 7,153,311 B2 | 12/2006 | Chung |
| 7,166,086 B2 | 1/2007 | Haider et al. |
| 7,197,359 B1 | 3/2007 | Tokudome et al. |
| 7,198,623 B2 | 4/2007 | Fischer et al. |
| 7,232,444 B2 | 6/2007 | Chang |
| 7,241,208 B2 | 7/2007 | Suissa et al. |
| D553,005 S | 10/2007 | Py et al. |
| 7,276,051 B1 | 10/2007 | Henley et al. |
| 7,293,930 B2 | 11/2007 | Chuang |
| 7,314,326 B2 | 1/2008 | Rosenberg |
| 7,316,657 B2 | 1/2008 | Kleinhenz et al. |
| 7,316,671 B2 | 1/2008 | Lastovich et al. |
| 7,318,828 B1 | 1/2008 | Revivo |
| 7,320,691 B2 | 1/2008 | Pilcher et al. |
| 7,320,801 B2 | 1/2008 | Kelly |
| 7,354,423 B2 | 4/2008 | Zelickson et al. |
| 7,364,565 B2 | 4/2008 | Freeman |
| 7,384,405 B2 | 6/2008 | Rhoades |
| 7,422,567 B2 | 9/2008 | Lastovich et al. |
| 7,427,273 B2 | 9/2008 | Mitsui |
| 7,458,944 B2 | 12/2008 | Liste et al. |
| 584,151 A1 | 1/2009 | Murphy |
| 7,476,205 B2 | 1/2009 | Erdmann |
| 7,477,938 B2 | 1/2009 | Sun et al. |
| 7,482,314 B2 | 1/2009 | Grimes et al. |
| 7,485,125 B2 | 2/2009 | Sjostrom |
| 7,489,989 B2 | 2/2009 | Sukhanov et al. |
| 7,507,228 B2 | 3/2009 | Sun et al. |
| 7,582,067 B2 | 9/2009 | Van Acker |
| 7,597,900 B2 | 10/2009 | Zimmer et al. |
| 7,597,901 B2 | 10/2009 | Clarot et al. |
| 7,658,742 B2 | 2/2010 | Karasiuk |
| 7,678,120 B2 | 3/2010 | Shadduck |
| 7,744,582 B2 | 6/2010 | Sadowski et al. |
| 7,789,886 B2 | 9/2010 | Shadduck |
| 7,837,695 B2 | 11/2010 | Hart et al. |
| 7,857,806 B2 | 12/2010 | Karpowicz et al. |
| 7,901,373 B2 | 3/2011 | Tavger |
| 7,951,156 B2 | 5/2011 | Karasiuk |
| 7,993,333 B2 | 8/2011 | Oral et al. |
| 8,025,669 B1 | 9/2011 | David et al. |
| RE42,960 E | 11/2011 | Waldron |
| 8,048,089 B2 | 11/2011 | Ignon et al. |
| 8,066,716 B2 | 11/2011 | Shadduck |
| 8,088,085 B2 | 1/2012 | Thiebaut et al. |
| 8,105,295 B2 | 1/2012 | Blott et al. |
| 8,128,638 B2 | 3/2012 | Karasiuk et al. |
| D664,254 S | 7/2012 | Yokoyama et al. |
| 8,221,437 B2 | 7/2012 | Waldron et al. |
| 8,231,292 B2 | 7/2012 | Rabe et al. |
| 8,236,008 B2 | 8/2012 | Boone, III et al. |
| 8,277,287 B2 | 10/2012 | Hart |
| 8,337,513 B2 | 12/2012 | Shadduck |

(56) References Cited

U.S. PATENT DOCUMENTS

| | | |
|---|---|---|
| 8,343,116 B2 | 1/2013 | Ignon et al. |
| D678,783 S | 3/2013 | Wilcox et al. |
| 8,475,507 B2 | 7/2013 | Dewey et al. |
| 8,573,874 B2 | 11/2013 | Neuner |
| 8,579,916 B2 | 11/2013 | Cheney |
| 8,721,662 B2 | 5/2014 | Karasiuk |
| D709,617 S | 7/2014 | Iliesco de Grimaldi et al. |
| 8,814,836 B2 | 8/2014 | Ignon et al. |
| 8,858,570 B2 | 10/2014 | Chang |
| 8,939,669 B2 | 1/2015 | Le et al. |
| D722,172 S | 2/2015 | Amemiya et al. |
| 8,945,104 B2 | 2/2015 | Boone, III et al. |
| 9,050,133 B1 | 6/2015 | Boone, III et al. |
| 9,056,193 B2 | 6/2015 | Ignon et al. |
| 9,072,533 B2 | 7/2015 | Liu et al. |
| D743,558 S | 11/2015 | Kim et al. |
| 9,468,464 B2 | 10/2016 | Shadduck |
| 9,474,886 B2 | 10/2016 | Ignon et al. |
| 9,486,615 B2 | 11/2016 | Ignon et al. |
| 9,498,610 B2 | 11/2016 | Ignon et al. |
| 9,517,085 B2 | 12/2016 | Karasiuk |
| 9,550,052 B2 | 1/2017 | Ignon et al. |
| 9,566,088 B2 | 2/2017 | Ignon et al. |
| D787,054 S | 5/2017 | Rini et al. |
| 9,642,997 B2 | 5/2017 | Ignon et al. |
| 9,662,482 B2 | 5/2017 | Ignon et al. |
| 9,700,684 B2 | 7/2017 | Vlodaver et al. |
| 9,731,053 B2 | 8/2017 | Alai |
| 9,775,645 B2 | 10/2017 | Boone, III |
| 9,775,646 B2 | 10/2017 | Shadduck |
| 9,814,868 B2 | 11/2017 | Ignon et al. |
| 9,833,261 B2 | 12/2017 | Boone, III et al. |
| 9,861,442 B2 | 1/2018 | Tankovich et al. |
| D811,381 S | 2/2018 | Morohoshi et al. |
| 9,918,727 B1 | 3/2018 | Boone, III et al. |
| 9,949,552 B2 | 4/2018 | Rabe et al. |
| 9,950,147 B2 | 4/2018 | Mehta |
| 9,955,769 B2 | 5/2018 | Rabe et al. |
| D822,845 S | 7/2018 | Shimobayashi et al. |
| 10,035,007 B2 | 7/2018 | Ignon et al. |
| D825,763 S | 8/2018 | Lim et al. |
| 10,076,646 B2 | 9/2018 | Casasanta, III et al. |
| 10,130,390 B1 | 11/2018 | Hart et al. |
| D836,781 S | 12/2018 | Meurer et al. |
| 10,172,644 B2 | 1/2019 | Ignon et al. |
| 10,179,229 B2 | 1/2019 | Ignon et al. |
| 10,188,193 B2 | 1/2019 | Rabe et al. |
| 10,206,743 B2 | 2/2019 | Tankovich et al. |
| 10,220,122 B2 | 3/2019 | Clark, III et al. |
| 10,238,812 B2 | 3/2019 | Ignon |
| 10,251,675 B2 | 4/2019 | Ignon et al. |
| D851,759 S | 6/2019 | Jones et al. |
| 10,314,378 B2 | 6/2019 | Rabe et al. |
| D852,962 S | 7/2019 | Chang |
| 10,357,641 B2 | 7/2019 | Ignon et al. |
| 10,357,642 B2 | 7/2019 | Ignon et al. |
| 10,334,933 B2 | 8/2019 | Rosario et al. |
| 10,369,073 B2 | 8/2019 | Rosario et al. |
| D861,913 S | 10/2019 | Stamm et al. |
| 10,456,321 B2 | 10/2019 | Shadduck |
| 10,456,567 B2 | 10/2019 | Streeter |
| D867,587 S | 11/2019 | Holtz |
| 10,485,983 B1 | 11/2019 | Boone, III et al. |
| D868,981 S | 12/2019 | Salamon et al. |
| 10,524,835 B2 | 1/2020 | Shadduck et al. |
| 10,556,096 B2 | 2/2020 | Ignon et al. |
| 10,556,097 B2 | 2/2020 | Ignon et al. |
| 10,667,985 B2 | 6/2020 | Decaux et al. |
| D893,024 S | 8/2020 | Whiteside |
| 10,737,080 B2 | 8/2020 | Patterson |
| 10,758,261 B2 | 9/2020 | Richardson |
| 10,918,190 B2 | 2/2021 | Laudati |
| 10,946,191 B2 | 3/2021 | Cazares Delgadillo |
| 10,993,743 B2 | 5/2021 | Ignon et al. |
| 11,020,577 B2 | 6/2021 | Ignon et al. |
| 2001/0023351 A1 | 9/2001 | Eilers |
| 2001/0037118 A1 | 11/2001 | Shadduck |
| 2001/0049511 A1 | 12/2001 | Coleman et al. |
| 2002/0016601 A1 | 2/2002 | Shadduck |
| 2002/0041891 A1 | 4/2002 | Cheski |
| 2002/0058952 A1 | 5/2002 | Weber et al. |
| 2002/0107527 A1 | 8/2002 | Burres |
| 2002/0128663 A1 | 9/2002 | Mercier et al. |
| 2002/0133110 A1 | 9/2002 | Citow |
| 2002/0133176 A1 | 9/2002 | Parkin et al. |
| 2002/0151826 A1 | 10/2002 | Ramey et al. |
| 2002/0151908 A1 | 10/2002 | Mallett, Sr. et al. |
| 2002/0162863 A1 | 11/2002 | Brincat |
| 2002/0188261 A1 | 12/2002 | Hruska |
| 2003/0012415 A1 | 1/2003 | Cossel |
| 2003/0018252 A1 | 1/2003 | Duchon et al. |
| 2003/0060834 A1 | 3/2003 | Muldner |
| 2003/0093040 A1 | 5/2003 | Mikszta et al. |
| 2003/0093089 A1 | 5/2003 | Greenberg |
| 2003/0097139 A1 | 5/2003 | Karasiuk |
| 2003/0167032 A1 | 9/2003 | Ignon |
| 2003/0187462 A1 | 10/2003 | Chang |
| 2003/0208159 A1 | 11/2003 | Ignon et al. |
| 2003/0212127 A1 | 11/2003 | Glassman et al. |
| 2003/0212415 A1 | 11/2003 | Karasiuk |
| 2004/0010222 A1 | 1/2004 | Nunomura et al. |
| 2004/0010269 A1 | 1/2004 | Grimes et al. |
| 2004/0015139 A1 | 1/2004 | La Bianco |
| 2004/0087972 A1 | 5/2004 | Mulholland et al. |
| 2004/0092895 A1 | 5/2004 | Harmon |
| 2004/0092959 A1 | 5/2004 | Bernaz |
| 2004/0097967 A1 | 5/2004 | Ignon |
| 2004/0122447 A1 | 6/2004 | Harmon et al. |
| 2004/0127914 A1 | 7/2004 | Chung |
| 2004/0138680 A1 | 7/2004 | Twitchell et al. |
| 2004/0143274 A1 | 7/2004 | Shadduck |
| 2004/0162565 A1 | 8/2004 | Carson et al. |
| 2004/0166172 A1 | 8/2004 | Rosati et al. |
| 2004/0219179 A1 | 11/2004 | McDaniel |
| 2004/0236291 A1 | 11/2004 | Zelickson et al. |
| 2004/0243149 A1 | 12/2004 | Lee, Jr. |
| 2004/0254587 A1 | 12/2004 | Park |
| 2004/0267285 A1 | 12/2004 | Chang |
| 2005/0037034 A1 | 2/2005 | Rhoades |
| 2005/0038448 A1 | 2/2005 | Chung |
| 2005/0059940 A1 | 3/2005 | Weber et al. |
| 2005/0084509 A1 | 4/2005 | Bernstein |
| 2005/0148958 A1 | 7/2005 | Rucinski |
| 2005/0203111 A1 | 9/2005 | David |
| 2005/0209611 A1 | 9/2005 | Greenberg |
| 2005/0283176 A1 | 12/2005 | Law |
| 2006/0002960 A1 | 1/2006 | Zoeteweij et al. |
| 2006/0116674 A1 | 6/2006 | Goble et al. |
| 2006/0161178 A1 | 7/2006 | Lee |
| 2006/0189964 A1 | 8/2006 | Anderson |
| 2006/0191562 A1 | 8/2006 | Numomura |
| 2006/0200099 A1 | 9/2006 | La Bianco et al. |
| 2006/0200172 A1 | 9/2006 | Shadduck |
| 2006/0200173 A1 | 9/2006 | Shadduck |
| 2006/0212029 A1 | 9/2006 | Arcusa Villacampa et al. |
| 2006/0222445 A1 | 10/2006 | Chuang |
| 2006/0253125 A1 | 11/2006 | Ignon |
| 2006/0264893 A1 | 11/2006 | Sage, Jr. et al. |
| 2006/0269580 A1 | 11/2006 | Cole et al. |
| 2007/0005078 A1 | 1/2007 | Hart et al. |
| 2007/0043382 A1 | 2/2007 | Cheney |
| 2007/0065515 A1 | 3/2007 | Key |
| 2007/0088371 A1 | 4/2007 | Karasiuk |
| 2007/0123808 A1 | 5/2007 | Rhoades |
| 2007/0139630 A1 | 6/2007 | Kleman et al. |
| 2007/0154502 A1 | 7/2007 | Hattendorf et al. |
| 2007/0156124 A1 | 7/2007 | Ignon et al. |
| 2007/0178121 A1 | 8/2007 | First et al. |
| 2007/0198031 A1 | 8/2007 | Kellogg |
| 2007/0208353 A1 | 9/2007 | Shadduck |
| 2007/0239173 A1 | 10/2007 | Khalaj |
| 2008/0027328 A1 | 1/2008 | Klopotek et al. |
| 2008/0091179 A1 | 4/2008 | Durkin et al. |
| 2008/0103563 A1 | 5/2008 | Powell |

(56) References Cited

U.S. PATENT DOCUMENTS

| | | |
|---|---|---|
| 2008/0119781 A1 | 5/2008 | King |
| 2008/0132914 A1 | 6/2008 | Bossard et al. |
| 2008/0139974 A1 | 6/2008 | Da Silva |
| 2008/0154161 A1 | 6/2008 | Abbott |
| 2008/0193493 A1 | 8/2008 | Rhoades |
| 2008/0200861 A1 | 8/2008 | Shalev et al. |
| 2008/0208146 A1 | 8/2008 | Brandwein et al. |
| 2008/0214987 A1 | 9/2008 | Xu |
| 2008/0215068 A1 | 9/2008 | Hart et al. |
| 2008/0221548 A1 | 9/2008 | Danenberg et al. |
| 2008/0243039 A1 | 10/2008 | Rhoades |
| 2008/0287864 A1 | 11/2008 | Rosenberg |
| 2008/0300529 A1 | 12/2008 | Reinstein |
| 2008/0300552 A1 | 12/2008 | Cichocki et al. |
| 2009/0048557 A1 | 2/2009 | Yeshurun et al. |
| 2009/0053390 A1 | 2/2009 | Sakou et al. |
| 2009/0062815 A1 | 3/2009 | Karasiuk et al. |
| 2009/0099091 A1 | 4/2009 | Hantash |
| 2009/0099093 A1 | 4/2009 | Hantash |
| 2009/0124985 A1 | 5/2009 | Hasenoehrl et al. |
| 2009/0138026 A1 | 5/2009 | Wu |
| 2009/0177171 A1 | 7/2009 | Ignon et al. |
| 2009/0192442 A1* | 7/2009 | Ignon ............... A61M 35/003 604/22 |
| 2009/0222023 A1 | 9/2009 | Boone, III et al. |
| 2010/0023003 A1 | 1/2010 | Mulholland |
| 2010/0045427 A1 | 2/2010 | Boone, III et al. |
| 2010/0049177 A1 | 2/2010 | Boone, III et al. |
| 2010/0049210 A1 | 2/2010 | Boone, III et al. |
| 2010/0217357 A1 | 8/2010 | Da Silva |
| 2010/0305495 A1 | 12/2010 | Anderson et al. |
| 2011/0054490 A1 | 3/2011 | Hart |
| 2011/0066162 A1 | 3/2011 | Cohen |
| 2011/0082415 A1* | 4/2011 | Ignon ............... A61M 35/003 604/22 |
| 2011/0295273 A1 | 12/2011 | Waldron et al. |
| 2012/0022435 A1 | 1/2012 | Ignon et al. |
| 2012/0041338 A1 | 2/2012 | Chickering, III et al. |
| 2012/0136374 A1 | 5/2012 | Karasiuk |
| 2013/0004230 A1 | 1/2013 | Kirk, III et al. |
| 2013/0018317 A1 | 1/2013 | Bobroff et al. |
| 2013/0066336 A1 | 3/2013 | Boone, III et al. |
| 2013/0096577 A1 | 4/2013 | Shadduck |
| 2013/0102978 A1 | 4/2013 | Ignon et al. |
| 2013/0144207 A1 | 6/2013 | Gonon |
| 2013/0144280 A1 | 6/2013 | Eckhouse et al. |
| 2013/0158547 A1 | 6/2013 | David |
| 2014/0079686 A1* | 3/2014 | Barman ............... A61K 8/69 424/94.67 |
| 2014/0234004 A1 | 8/2014 | Thorpe et al. |
| 2014/0343481 A1 | 11/2014 | Ignon |
| 2014/0343574 A1 | 11/2014 | Ignon et al. |
| 2014/0378887 A1 | 12/2014 | Chang et al. |
| 2015/0032047 A1 | 1/2015 | Ignon et al. |
| 2015/0230824 A1 | 8/2015 | Shadduck |
| 2015/0230825 A1 | 8/2015 | Shadduck |
| 2015/0231379 A1 | 8/2015 | Ignon et al. |
| 2015/0265822 A1 | 9/2015 | Ignon et al. |
| 2015/0272623 A1 | 10/2015 | Ignon et al. |
| 2015/0290442 A1 | 10/2015 | Ignon et al. |
| 2016/0018100 A1 | 1/2016 | Batt et al. |
| 2016/0038183 A1 | 2/2016 | Ignon et al. |
| 2016/0235257 A1 | 8/2016 | Daffer |
| 2016/0250415 A1 | 9/2016 | Yagi et al. |
| 2016/0256671 A1 | 9/2016 | Ignon et al. |
| 2017/0043150 A1 | 2/2017 | Kim |
| 2017/0065801 A1 | 3/2017 | Ignon et al. |
| 2017/0209894 A1 | 7/2017 | Sporrer |
| 2017/0224972 A1 | 8/2017 | Ignon et al. |
| 2017/0245876 A1 | 8/2017 | Ignon et al. |
| 2017/0266424 A1 | 9/2017 | Ignon et al. |
| 2017/0319835 A1 | 11/2017 | Ignon et al. |
| 2017/0319836 A1 | 11/2017 | Ignon et al. |
| 2017/0333689 A1 | 11/2017 | Ignon et al. |
| 2018/0140329 A1 | 5/2018 | Beijens et al. |
| 2018/0185675 A1 | 7/2018 | Kern et al. |
| 2018/0318568 A1 | 11/2018 | Ignon et al. |
| 2019/0070069 A1 | 3/2019 | Gertner et al. |
| 2019/0133642 A1 | 5/2019 | Ignon et al. |
| 2019/0143089 A1 | 5/2019 | Ignon et al. |
| 2019/0151637 A1 | 5/2019 | Groop et al. |
| 2019/0223914 A1 | 7/2019 | Ignon et al. |
| 2019/0336740 A1 | 11/2019 | Ignon et al. |
| 2020/0009007 A1 | 1/2020 | Shadduck |
| 2020/0016342 A1 | 1/2020 | Ignon |
| 2020/0171288 A1 | 6/2020 | Ignon et al. |
| 2020/0171289 A1 | 6/2020 | Ignon et al. |
| 2020/0179220 A1 | 6/2020 | Jablow |
| 2020/0289161 A1 | 9/2020 | Scooros |
| 2020/0316270 A1 | 10/2020 | Dijkstra et al. |
| 2020/0338586 A1 | 10/2020 | Park |
| 2020/0390468 A1 | 12/2020 | Alexander |
| 2021/0085367 A1 | 3/2021 | Shadduck et al. |
| 2021/0145480 A1 | 5/2021 | Ignon et al. |
| 2021/0145481 A1 | 5/2021 | Ignon et al. |
| 2021/0154453 A1 | 5/2021 | Ignon et al. |
| 2021/0154454 A1 | 5/2021 | Ignon et al. |
| 2021/0154455 A1 | 5/2021 | Ignon et al. |
| 2021/0177463 A1 | 6/2021 | Ignon et al. |

FOREIGN PATENT DOCUMENTS

| | | |
|---|---|---|
| CA | 2 340 154 | 9/2002 |
| CN | 107920948 | 4/2018 |
| DE | 59 95 21 | 7/1934 |
| DE | 24 15 633 | 10/1975 |
| DE | 33 38 057 | 8/1984 |
| DE | 34 21 390 A1 | 12/1985 |
| DE | 234 608 | 4/1986 |
| DE | 35 03 343 | 8/1986 |
| DE | 83 30 191 | 6/1987 |
| DE | 37 40 902 | 12/1988 |
| DE | 42 37 940 | 5/1993 |
| DE | 298 08 395 | 8/1998 |
| DE | 10 2004 015815 A1 | 11/2005 |
| EP | 0 258 901 | 9/1987 |
| EP | 0 564 392 | 3/1993 |
| EP | 0 784 997 | 7/1997 |
| EP | 1238643 | 4/2000 |
| EP | 1 453 558 | 9/2004 |
| EP | 2544563 | 9/2015 |
| EP | 2106780 | 3/2016 |
| EP | 3 217 899 | 5/2016 |
| EP | 2240099 | 2/2018 |
| EP | 3 302 319 | 4/2018 |
| EP | 2967633 | 4/2018 |
| EP | 3319573 | 5/2018 |
| EP | 3 340 908 | 7/2018 |
| EP | 2451367 | 1/2020 |
| EP | 3388006 | 3/2020 |
| EP | 2618797 | 4/2020 |
| EP | 3237055 | 8/2020 |
| EP | 3795204 | 3/2021 |
| EP | 3437575 | 4/2021 |
| ES | 1 037 776 | 4/1998 |
| FR | 2 712 172 | 5/1995 |
| FR | 2 773 461 | 7/1999 |
| GB | 1 372 609 | 10/1974 |
| GB | 2306351 | 5/1997 |
| IT | 553 076 | 12/1956 |
| IT | 118 49 22 | 3/1985 |
| JP | S55-034863 | 8/1963 |
| JP | H05-042060 | 2/1993 |
| JP | 1993-088552 | 12/1993 |
| JP | 09-294747 | 11/1997 |
| JP | 2003-534881 | 11/2003 |
| JP | 2003-339713 | 12/2003 |
| JP | 2004-275721 | 10/2004 |
| JP | 2006-503627 | 2/2006 |
| JP | 2006-204767 | 10/2006 |
| JP | 2010/042243 | 2/2010 |
| JP | 2012527967 | 11/2012 |
| JP | 5508285 | 3/2014 |
| JP | 2018-527052 | 9/2018 |

(56) References Cited

FOREIGN PATENT DOCUMENTS

| | | |
|---|---|---|
| KR | 20-0280320 | 7/2002 |
| KR | 10-20070070173 | 7/2007 |
| KR | 10-2018-0030607 | 3/2018 |
| KR | 10-1836310 | 3/2018 |
| WO | WO 1994/024980 | 11/1994 |
| WO | WO 1997/011650 | 3/1997 |
| WO | WO 2000/015300 | 3/2000 |
| WO | WO 00/79540 | 12/2000 |
| WO | WO 2001/93931 | 12/2001 |
| WO | WO 2003/073917 | 9/2003 |
| WO | WO 2004/037098 | 5/2004 |
| WO | WO 2005/070313 | 8/2005 |
| WO | WO 2006/018731 | 2/2006 |
| WO | WO 2006/031413 | 3/2006 |
| WO | WO 2007/114904 | 10/2007 |
| WO | WO 2009/088884 | 7/2009 |
| WO | WO 2009/097451 | 8/2009 |
| WO | WO 2011/006009 | 1/2011 |
| WO | WO 2011/110840 | 9/2011 |
| WO | WO 2012/145667 | 10/2012 |
| WO | WO 2014/091035 | 6/2014 |
| WO | WO 2014/151104 | 9/2014 |
| WO | WO 2016/106396 | 6/2016 |
| WO | WO 2017/007939 | 1/2017 |
| WO | WO 2021/018765 | 2/2021 |

OTHER PUBLICATIONS

Cox III et al., *Decreased Splatter in Dermabrasion*, Arch Facial Plastic Surgery, Jan.-Mar. 2000, vol. 2, pp. 23-26.

Ditre et al., *Effect of α-hydroxy acids on photoaged skin: A pilot clinical, histologic, and ultrastructural study*, Journal of American Academy of Dermatology, Feb. 1996, vol. 34, No. 2, Part 1, pp. 187-195.

Harris et al., *Combining Manual Dermasanding with Low Strength Trichloroacetic Acid to Improve Antinically Injured Skin*, The Journal of Dermatologic Surgery and Oncology, Jul. 1994, vol. 20, No. 7, pp. 436-442.

Microdermabrader Pepita Instruction Manual, Mattioli Engineering S.R.L., PEP_USA2.doc Rev 1.1, Sep. 29, 1997.

U.S. Appl. No. 15/588,102, filed May 5, 2017, Devices for Treating Skin Using Treatment Materials Located Along a Tip.

U.S. Appl. No. 15/344,357, filed Nov. 4, 2016, Devices and Methods for Skin Treatment.

U.S. Appl. No. 11/417,396 (U.S. Pat. No. 7,678,120), May 3, 2006, Instruments and Techniques for Controlled Removal of Epidermal Layers.

U.S. Appl. No. 14/702,486 (U.S. Pat. No. 9,468,464), filed May 1, 2015, Methods for Treating the Skin Using Vacuum.

U.S. Appl. No. 15/660,777 (U.S. Pat. No. 10/357,642), filed Jul. 26, 2017, Removable Tips for Use With Skin.

U.S. Appl. No. 14/734,995, filed Jun. 9, 2015, Devices and Systems for Treating Skin Surfaces.

U.S. Appl. No. 16/241,572, filed Jan. 7, 2019, Devices, Systems and Methods for Treating the Skin.

Hydrafacial® Tower—User guide. Edge Systems. Revised Jun. 23, 2016. p. 16.

U.S. Appl. No. 09/648,025 (U.S. Pat. No. 6,641,591), filed Aug. 25, 2000, Instruments and Techniques for Controlled Removal of Epidermal Layers.

U.S. Appl. No. 10/699,747 (U.S. Pat. No. 7,789,886), filed Nov. 3, 2003 Instruments and Techniques for Controlled Removal of Epidermal Layers.

U.S. Appl. No. 11/739,615 (U.S. Pat. No. 8,337,513), filed Apr. 24, 2007, Instruments and Techniques for Controlled Removal of Epidermal Layers.

U.S. Appl. No. 11/417,709 (U.S. Pat. No. 8,066,716), filed May 3, 2006, Instruments and Techniques for Controlled Removal of Epidermal Layers.

U.S. Appl. No. 11/417,396 (U.S. Pat. No. 7,678,120), filed May 3, 2006, Instruments and Techniques for Controlled Removal of Epidermal Layers.

U.S. Appl. No. 13/620,164, filed Sep. 14, 2012, Instruments and Techniques for Controlled Removal of Epidermal Layers.

U.S. Appl. No. 14/702,509 (U.S. Pat. No. 9,775,646), filed May 1, 2015, Devices and Systems for Treating the Skin Using Vacuum.

U.S. Appl. No. 14/702,486 (U.S. Pat. No. 9,468,464), filed May 1, 2015, Using Vacuum Methods for Treating the Skin.

U.S. Appl. No. 15/953,337, filed Apr. 13, 2018, Instruments and Techniques for Controlled Removal of Epidermal Layers.

U.S. Appl. No. 11/392,348 (U.S. Pat. No. 8,048,089), filed Mar. 29, 2006, Apparatus and Methods for Treating the Skin.

U.S. Appl. No. 13/267,554 (U.S. Pat. No. 9,474,886), filed Oct. 6, 2011, Removable Tips for Skin Treatment Systems.

U.S. Appl. No. 14/698,673 (U.S. Pat. No. 9,550,052), filed Apr. 28, 2015 Console System for the Treatment of Skin.

U.S. Appl. No. 14/698,713 (U.S. Pat. No. 9,662,482), filed Apr. 28, 2015, Methods and Systems for Extraction of Materials From Skin.

U.S. Appl. No. 14/700,789 (U.S. Pat. No. 9,814,868), filed Apr. 30, 2015, Tip With Embedded Materials for Skin Treatment.

U.S. Appl. No. 15/660,750 (U.S. Pat. No. 10/357,641), filed Jul. 26, 2017, Tips for Skin Treatment Device.

U.S. Appl. No. 15/660,777 (U.S. Pat. No. 10/357,642), filed Jul. 26, 2017, Removable Tips for Use With Skin Treatment Systems.

U.S. Appl. No. 16/517,268, filed Jul. 19, 2019, Devices and Methods for Treating Skin.

U.S. Appl. No. 17/165,820, filed Feb. 2, 2021, Devices and Methods for Treating Skin.

U.S. Appl. No. 17/165,807, filed Feb. 2, 2021, Devices and Methods for Treating Skin.

U.S. Appl. No. 29/679,299, filed Feb. 4, 2019, Skin Treatment System.

U.S. Appl. No. 29/679,306, filed Feb. 4, 2019, Handpiece Assembly Tip.

U.S. Appl. No. 29/679,302, filed Feb. 4, 2019, Handpiece Assembly Tip.

U.S. Appl. No. 09/294,254 (U.S. Pat. No. 6,162,232), filed Apr. 19, 1999, Instruments and Techniques for High-Velocity Fluid Abrasion of Epidermal Layers With Skin Cooling.

U.S. Appl. No. 09/475,480 (U.S. Pat. No. 6,299,620), filed Dec. 30, 1999, Instruments and Techniques for Inducing Neocollagenesis in Skin Treatments.

U.S. Appl. No. 09/475,479 (U.S. Pat. No. 6,387,103), filed Dec. 30, 1999, Instruments and Techniques for Inducing Neocollagenesis in Skin Treatments.

U.S. Appl. No. 11/370,200, filed Mar. 7, 2006, Microdermabrasion Method and Apparatus.

U.S. Appl. No. 12/362,353 (U.S. Pat. No. 9,056,193), filed Jan. 29, 2009, Apparatus and Method for Treating the Skin.

U.S. Appl. No. 14/734,995 (U.S. Pat. No. 11,020,577), filed Jun. 9, 2015, Devices and Systems for Treating Skin Surfaces.

U.S. Appl. No. 17/332,897, filed May 27, 2021, Devices, Systems, and Methods for Treating the Skin.

U.S. Appl. No. 12/832,663 (U.S. Pat. No. 8,814,836), filed Jul. 8, 2010, Devices, Systems and Methods for Treating the Skin Using Time-Release Substances.

U.S. Appl. No. 14/455,762 (U.S. Pat. No. 9,642,997), filed Aug. 8, 2014, Devices for Treating Skin Using Treatment Materials Located Along a Tip.

U.S. Appl. No. 15/588,102 (U.S. Pat. No. 10,556,097), filed May 5, 2017, Devices for Treating Skin Using Treatment Materials Located Along a Tip.

U.S. Appl. No. 16/784,850, filed Feb. 7, 2020, Devices and Methods for Treating Skin.

U.S. Appl. No. 12/346,582 (U.S. Pat. No. 8,343,116), filed Dec. 30, 2008, Apparatus and Method for Treating the Skin.

U.S. Appl. No. 13/620,376 (U.S. Pat. No. 9,486,615), filed Sep. 14, 2012. Microdermabrasion Apparatus and Method.

U.S. Appl. No. 15/344,357 (U.S. Pat. No. 10,556,096), filed Nov. 4, 2016, Devices and Methods for Skin Treatment.

U.S. Appl. No. 16/784,044, filed Feb. 6, 2020, Devices and Methods for Skin Treatment.

(56) References Cited

OTHER PUBLICATIONS

U.S. Appl. No. 09/540,945 (U.S. Pat. No. 6,592,595), filed Mar. 31, 2000, Microdermabrasion and Suction Massage Apparatus and Method.
U.S. Appl. No. 09/698,409 (U.S. Pat. No. 6,527,783), filed Oct. 27, 2000, Microdermabrasion and Suction Massage Apparatus and Method.
U.S. Appl. No. 10/177,173 (U.S. Pat. No. 6,673,082), filed Jun. 20, 2002, Microdermabrasion Handpiece With Supply and Return Lumens.
U.S. Appl. No. 10/315,478 (U.S. Pat. No. 6,942,649), filed Dec. 10, 2002, Microdermabrasion Fluid Application System and Method.
U.S. Appl. No. 09/699,220 (U.S. Pat. No. 6,629,983), filed Oct. 27, 2000, Apparatus and Method for Skin/Surface Abrasion.
U.S. Appl. No. 14/211,089 (U.S. Pat. No. 10,238,812), filed Mar. 14, 2014, Skin Treatment Systems and Methods Using Needles.
U.S. Appl. No. 16/363,310, filed Mar. 25, 2019, Skin Treatment Systems and Methods Using Needles.
U.S. Appl. No. 14/211,290 (U.S. Pat. No. 9,566,088), filed Mar. 14, 2014, Devices, Systems and Methods for Treating the Skin.
U.S. Appl. No. 15/430,209 (U.S. Pat. No. 10,251,675), filed Feb. 10, 2017, Devices, Systems and Methods for Treating the Skin.
U.S. Appl. No. 16/376,956, filed Apr. 5, 2019, Devices, Systems and Methods for Treating the Skin.
U.S. Appl. No. 14/774,641 (U.S. Pat. No. 10,172,644), filed Sep. 10, 2015, Devices, Systems and Methods for Treating the Skin.
U.S. Appl. No. 16/241,572 (U.S. Pat. No. 10,993,743), filed Jan. 7, 2019 Devices, Systems and Methods for Treating the Skin.
U.S. Appl. No. 17/163,128, filed Jan. 29, 2021, Devices, Systems and Methods for Treating the Skin.
U.S. Appl. No. 17/163,199, filed Jan. 29, 2021, Devices, Systems and Methods for Treating the Skin.
U.S. Appl. No. 17/163,237, filed Jan. 29, 2021, Devices, Systems and Methods for Treating the Skin.
U.S. Appl. No. 17/163,240, filed Jan. 29, 2021, Devices, Systems and Methods for Treating the Skin.
U.S. Appl. No. 14/998,375 (U.S. Pat. No. 9,498,610), filed Dec. 23, 2015, Devices and Methods for Treating the Skin Using a Rollerball or a Wicking Member.
U.S. Appl. No. 15/354,754 (U.S. Pat. No. 10,035,007), filed Nov. 17, 2016, Devices and Methods for Treating the Skin.
U.S. Appl. No. 16/040,397, filed Jul. 19, 2018, Devices and Methods for Treating the Skin.
U.S. Appl. No. 17/164,580, filed Feb. 1, 2021, Devices and Methods for Treating the Skin.
U.S. Appl. No. 15/498,416 (U.S. Pat. No. 10,179,229), filed Apr. 26, 2017, Devices and Methods for Treating the Skin Using a Porous Member.
U.S. Appl. No. 16/246,306, filed Jan. 11, 2019, Devices and Methods for Treating the Skin Using a Porous Member.

\* cited by examiner

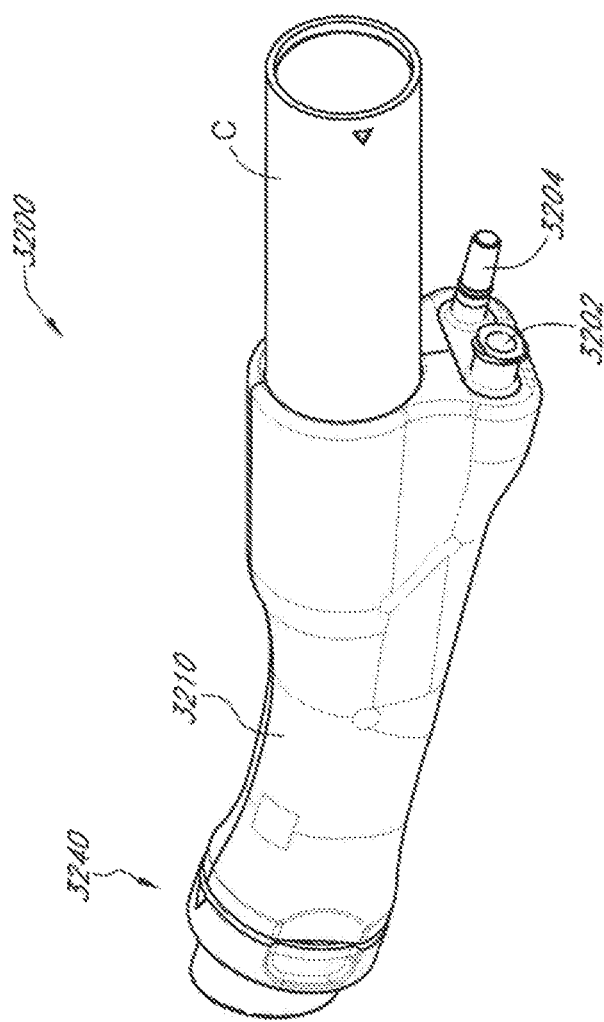

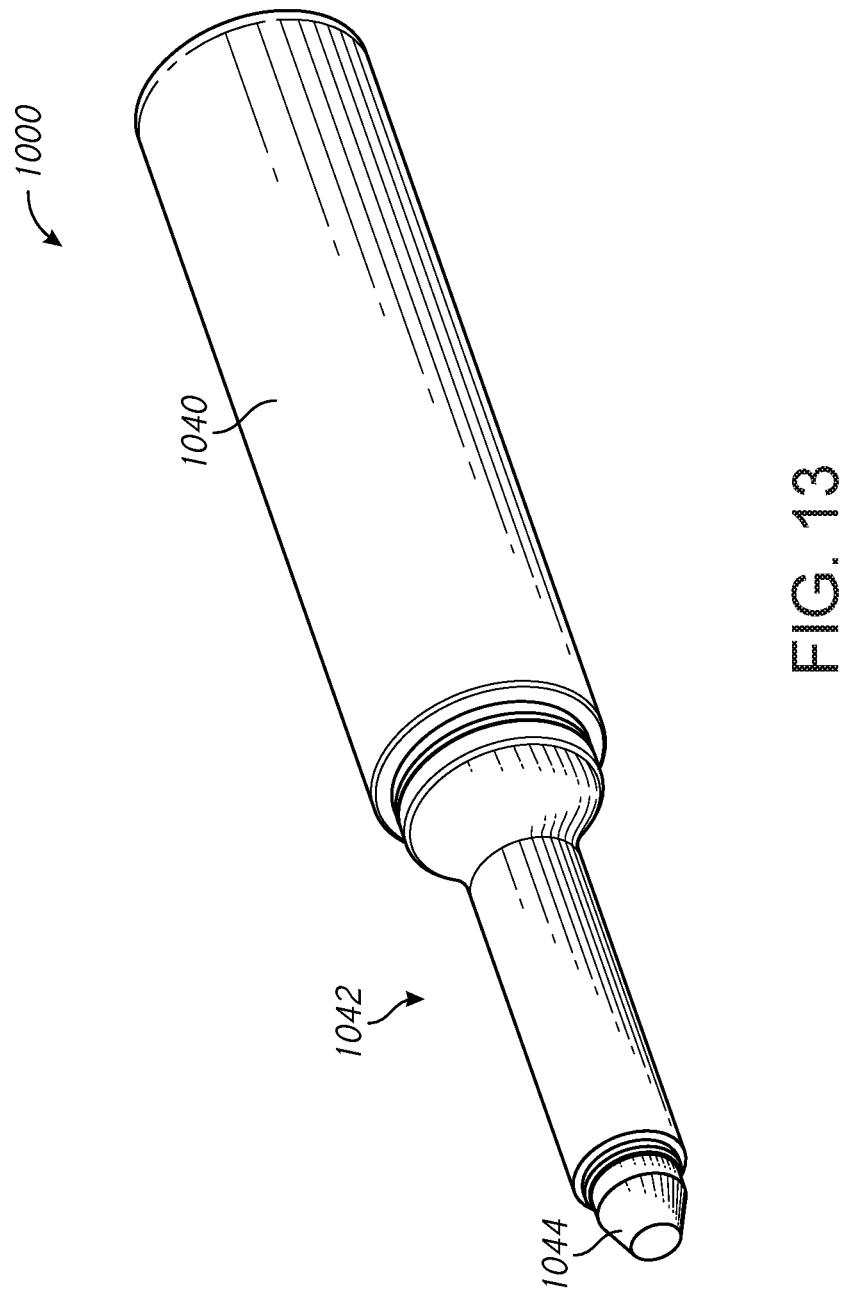

DEVICES, SYSTEMS AND METHODS FOR PROMOTING HAIR GROWTH

CROSS-REFERENCE TO RELATED APPLICATIONS & INCORPORATION BY REFERENCE

This application claims priority to U.S. Provisional Patent Application No. 62/190,243, filed Jul. 8, 2015, and U.S. Provisional Patent Application No. 62/320,476, filed Apr. 9, 2016, the entire contents of both of which are incorporated herein by reference in their entireties.

The entireties of U.S. patent application Ser. No. 12/346,582, filed Dec. 30, 2008 and issued on Jan. 1, 2013 as U.S. Pat. No. 8,343,116, U.S. patent application Ser. No. 11/392,348, filed Mar. 29, 2006 and issued on Nov. 1, 2011 as U.S. Pat. No. 8,048,089, U.S. patent application Ser. No. 12/832,663, filed Jul. 8, 2010 and issued on Aug. 26, 2014 as U.S. Pat. No. 8,814,836, International Patent Application No. PCT/US2014/024992, filed Mar. 12, 2014 and published on Sep. 25, 2014 as PCT Publ. No. WO 2014/151104 and International Patent Application No. PCT/US2015/067531, filed Dec. 22, 2015 and published on Jun. 30, 2106 as PCT Publ. No. WO 2016/106396 are hereby incorporated by reference herein and made a part of the present specification.

BACKGROUND

Field

This application relates generally to the promotion of hair growth, and more specifically, to apparatuses, systems and methods for facilitating hair growth by treatment of a subject's adjacent skin tissue. The application also has applicability to any other type of skin treatment procedure and other skin treatment devices and systems.

SUMMARY

According to some embodiments, embodiments of the devices, systems and methods disclosed herein have specific relevance to treatment devices, systems and methods for the promotion of hair growth and the preparation/treatment of skin in connection with such hair growth. However, the features, advantages and other characteristics disclosed herein may have direct or indirect applicability in other applications, such as, for example, medical devices and procedure, mechanical devices and non-skin treatment devices and methods and/or the like. For example, the various devices, systems and related methods described herein can be used in other types of skin treatment procedures and protocols (non-hair growth procedures), such as, e.g., for microdermabrasion of skin, for treatment of acne, oily skin and other skin ailments and conditions, for the removal of blackheads, sebum and/or other substances from skin, for skin tightening, skin lightening, anti-aging, anti-oxidant treatment and/or for any other type of skin or tissue treatment.

According to some embodiments, devices, systems and methods can be used to promote the growth of hair. For instance, one or more fluids and/or other substances can be selectively delivered to and/or into the scalp (e.g., at least partially into a subject's skin tissue) to help stimulate hair follicle growth and/or otherwise promote hair growth. As discussed in greater detail herein, the delivery of such materials on and/or into a subject's skin surface (e.g., scalp) can be facilitated with the assistance one or more infusion or penetration features and methods. For example, the delivery of the desired or required treatment materials (e.g., growth factors) can be facilitated by use of one or more of the following: use of suction or vacuum (e.g., to stimulate blood flow), use of force, pressure and/or mechanical agitation (e.g., mechanical pulsing using air delivery to a targeted skin surface), use of needles or other tissue penetration devices or tools, use of exfoliation or massaging to targeted skin tissue, use of thermal conditioning (e.g., heating or cooling) of the targeted skin tissue, use of energy delivery simultaneously with the delivery of treatment materials (e.g., ultrasound, laser, radiofrequency energy, microwave energy, electric current or stimulation, iontophoresis, etc.), use of light (e.g., red light, ultraviolet light, etc.), use of hair implants or other hair growth systems, methods and/or technologies) and/or the like.

According to some embodiments, an engagement member or shroud configured to be positioned along a distal end of a handpiece assembly, the engagement member comprising a proximal end configured to attach to a proximal component of a handpiece assembly, a distal end configured to contact and engage with a skin surface being treated, a body extending between the proximal end and the distal end that is configured to accommodate for irregularities and other contours along the skin surface being treated, wherein the engagement member is flexible, and wherein the engagement member is configured to facilitate capture of liquids present along the skin surface being treated during use.

According to some embodiments, the engagement member or shroud comprises a rubber or other elastomeric material (e.g., silicone rubber). In some embodiments, the engagement member comprises at least one bellow or other collapsible member to facilitate the maneuverability of the engagement member relative to the skin surface being treated.

In some embodiments, the engagement member or shroud is configured to couple to a tip of the handpiece assembly, wherein the proximal end of the engagement member is configured to fixedly or removably coupled to the tip. In some embodiments, the engagement member or shroud is configured to couple to a main body portion of the handpiece assembly, wherein the proximal end of the engagement member is configured to fixedly or removably coupled to the main body portion of the handpiece assembly.

According to some embodiments, a method of promoting hair growth or hair stimulation in a subject comprises applying vacuum or suction using a handpiece assembly along a targeted portion of the subject's skin surface where hair growth or hair stimulation is desired and providing at least one treatment material to said targeted portion of the subject's skin surface, wherein the application of vacuum or suction helps promote hair growth or stimulate hair.

According to some embodiments, a method of promoting hair growth or hair stimulation in a subject comprises applying positive pressure using a handpiece assembly along a targeted portion of the subject's skin surface where hair growth or hair stimulation is desired and providing at least one treatment material to said targeted portion of the subject's skin surface, wherein the application of positive pressure helps promote hair growth or stimulate hair.

According to some embodiments, the vacuum or suction is applied continuously or intermittently. In some embodiments, the vacuum or suction is applied intermittently using a pulsing device. In one embodiment, the pulsing device is configured to create alternating first and second pressure s along the subject's skin surface, wherein the first pressure is greater than the second pressure, and wherein the second pressure is a vacuum or suction. In some embodiments, the first pressure is a positive pressure. In some embodiments, the first pressure is a vacuum or suction.

According to some embodiments, a distal end of the handpiece assembly is configured to contact the subject's skin surface. In some embodiments, the distal end of the handpiece assembly comprises a tip. In some embodiments, the tip is removable from a proximal portion of the handpiece assembly. In one embodiment, the tip comprises at least one suction port or opening through which vacuum or suction is selectively applied.

According to some embodiments, the at least one treatment material comprises one or more of the following: growth factors (e.g., human-derived, non-human derived, liposome (courier) chemically altered growth factors, etc.), amino acids (e.g., leucine, isoleucine, valine, etc.), antioxidants, minoxidil, other antihypertensive vasodilators, finasteride, dutasteride, ketoconazole, spironolactone, flutamide, catechin, epicatechin, other phytochemicals, carnitine, rejuvaplex, copper peptides, other hair growth-stimulating agents, other pharmaceuticals and non-pharmaceuticals, plant-derived products, cleansing or pre-cleansing shampoos, other cleansing or pre-cleansing solutions (e.g., salicylic acid, GlySal™ (glycolic acid and salicylic acid mix), other acids, etc.), and other natural and synthetic materials. In some embodiments, the at least one treatment material is contained in a bottle, said bottle being in fluid communication with the handpiece assembly. In one embodiment, the at least one treatment material is contained in a cartridge, said cartridge being configured to secure to the handpiece assembly. In some embodiments, the at least one treatment material is positioned on a tip of the handpiece assembly, wherein the at least one treatment material is configured to at least partially dissolve or release in the presence of a liquid.

According to some embodiments, the application of vacuum or suction helps promote blood flow at or near the targeted portion of the subject's skin surface. In some embodiments, the method further comprises at least partially exfoliating the skin surface of the subject. In some embodiments, at least partially exfoliating the skin surface of the subject comprises exfoliating using an abrasive surface or member. In one embodiment, at least partially exfoliating the skin surface of the subject comprises exfoliating using a chemical exfoliating agent. In some embodiments, at least partially exfoliating the skin surface of the subject precedes providing at least one treatment material to said targeted portion of the subject's skin surface. In some embodiments, the at least one treatment material comprises a growth factor.

According to some embodiments, the method further comprises providing a light treatment to the skin tissue. In some embodiments, the light treatment comprises providing red or blue light to the skin tissue. In one embodiment, the light treatment is used to activate the at least one treatment material to facilitate hair growth or stimulate hair.

According to some embodiments, the method additionally comprises at least partially penetrating the skin surface of the subject. In some embodiments, penetrating the skin surface of the subject comprises using at least one needle assembly configured to selectively penetrate skin tissue. In some embodiments, the at least one needle assembly is configured to open up passages within the skin of the subject, said passages leading to or near a subject's follicles. In some embodiments, the at least one needle assembly is coated or otherwise provided with at least one treatment material. In one embodiment, the at least one needle assembly comprises a plurality of hollow needles, wherein at least one treatment material is configured to be delivered through passages of the hollow needles.

According to some embodiments, the method further comprises massaging or otherwise agitating the targeted portion of the subject's skin surface to facilitate the delivery of the at least one treatment material deeper into said skin surface. In some embodiments, the massaging or agitating results in at least partially opening pores along the subject's skin surface to facilitate the passage of the at least one treatment materials therethrough. In one embodiment, the massaging or agitating comprises moving a handpiece comprising a surface with at least one non-linear feature relative to said skin surface. In some embodiments, the at least one non-linear feature comprises an undulating yet smooth surface or feature.

According to some embodiments, the method additionally comprises performing the procedure at or near a portion of skin tissue that has received hair implants. In some embodiments, the method further comprises implanting at least a plurality of hair follicles at or near the portion of the skin tissue being treated.

According to some embodiments, the method additionally comprises heating or cooling the targeted portion of the subject's skin surface being treated. In some embodiments, heating or cooling the skin surface comprises using a separate thermally-conditioned device (e.g., a thermoelectric device, Peltier element, etc.).

According to some embodiments, further comprises providing energy to the targeted portion of the subject's skin surface to enhance hair growth or hair stimulation. In some embodiments, wherein the energy provided to the skin tissue comprises one or more of the following: radiofrequency (RF) energy, microwave energy, ultrasound energy, iontophoresis and laser.

BRIEF DESCRIPTION OF THE DRAWINGS

These and other features, aspects and advantages of the present application are described with reference to drawings of certain embodiments, which are intended to illustrate, but not to limit, the present application and the inventions disclosed therein. It is to be understood that these drawings are for the purpose of illustrating the various concepts disclosed herein and may not be to scale.

FIGS. 3A-3E illustrate various views of a system comprising air pulsing, according to one embodiment;

FIG. 13 illustrates a perspective view of an assembly comprising a wicking member for use with a treatment system according to one embodiment;

DETAILED DESCRIPTION

Figure 1:
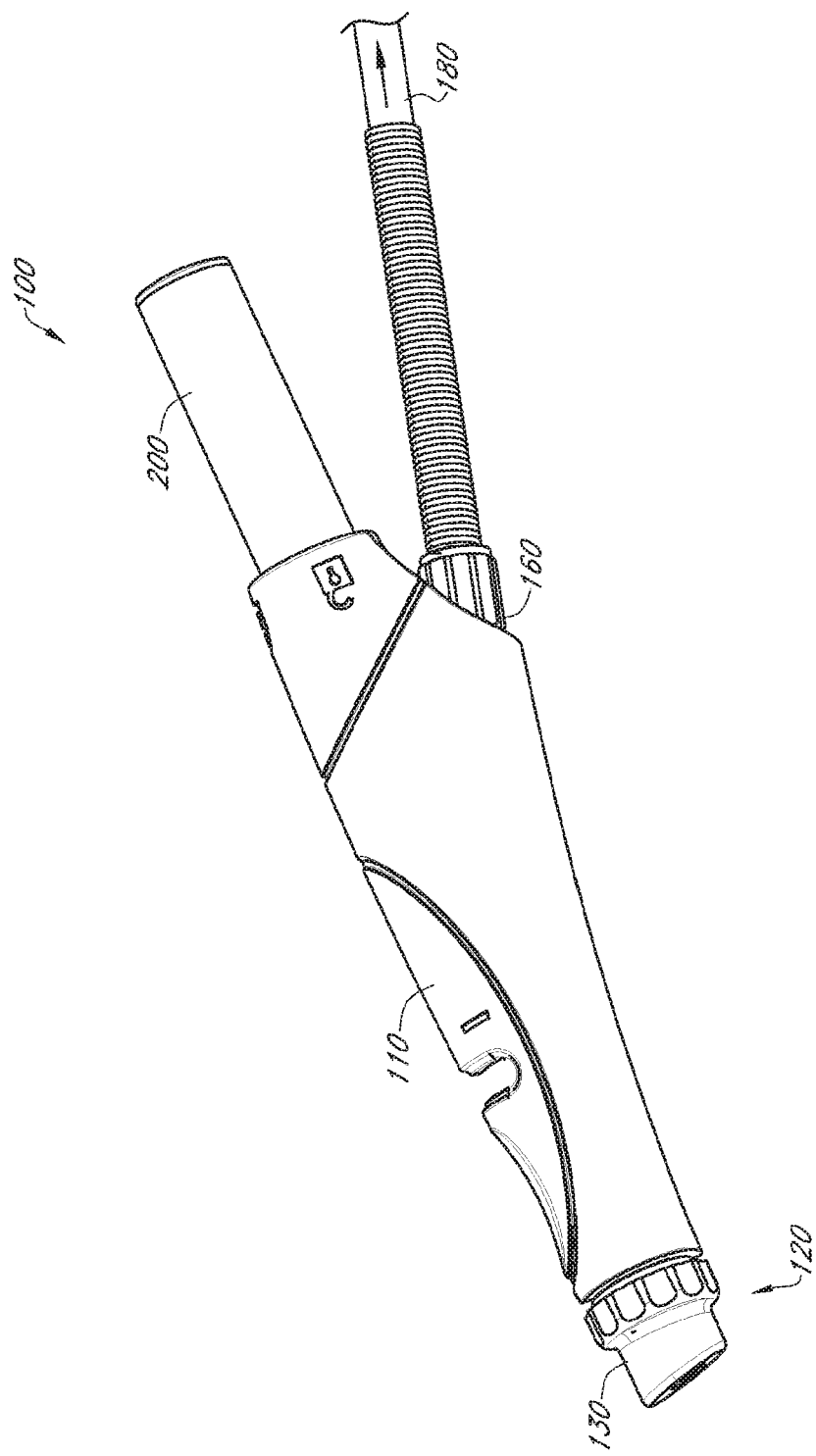
FIG. 1 illustrates a perspective view of a handpiece assembly configured for use with skin treatment systems, including those adapted to promote hair growth, according to one embodiment.

Although the various embodiments of the devices, systems and methods disclosed herein have specific relevance to treatment devices, systems and methods for the promotion of hair growth and the preparation/treatment of skin in connection with such hair growth, the features, advantages and other characteristics disclosed herein may have direct or indirect applicability in other applications, such as, for example, medical devices and procedure, mechanical devices and non-skin treatment devices and methods and/or the like. For example, the various devices, systems and related methods described herein can be used in other types of skin treatment procedures and protocols (non-hair growth procedures), such as, e.g., for microdermabrasion of skin, for treatment of acne, oily skin and other skin ailments and conditions, for the removal of blackheads, sebum and/or other substances from skin, for skin tightening, skin lightening, anti-aging, anti-oxidant treatment and/or for any other type of skin or tissue treatment.

According to some embodiments, devices, systems and methods can be used to promote the growth of hair. For instance, one or more fluids and/or other substances can be selectively delivered to and/or into the scalp (e.g., at least partially into a subject's skin tissue) to help stimulate hair follicle growth and/or otherwise promote hair growth. As discussed in greater detail herein, the delivery of such materials on and/or into a subject's skin surface (e.g., scalp) can be facilitated with the assistance one or more infusion or penetration features and methods. For example, the delivery of the desired or required treatment materials (e.g., growth factors) can be facilitated by use of one or more of the following: use of suction or vacuum (e.g., to stimulate blood flow), use of force, pressure and/or mechanical agitation (e.g., mechanical pulsing using air delivery to a targeted skin surface), use of needles or other tissue penetration devices or tools, use of exfoliation or massaging to targeted skin tissue, use of thermal conditioning (e.g., heating or cooling) of the targeted skin tissue, use of energy delivery simultaneously with the delivery of treatment materials (e.g., ultrasound, laser, radiofrequency energy, microwave energy, electric current or stimulation, iontophoresis, etc.), use of light (e.g., red light, ultraviolet light, etc.), use of hair implants or other hair growth systems, methods and/or technologies) and/or the like.

The various steps, technologies and/or other features described herein can be used alone or in conjunction with one another to effect a particular result, e.g., the promotion of hair growth in a subject, the strengthening of existing or new hair in a subject and/or the like. As noted above, the various devices, systems and related methods described herein can be used in other types of skin treatment procedures and protocols (non-hair growth procedures), such as, e.g., for microdermabrasion of skin, for treatment of acne, oily skin and other skin ailments and conditions, for the removal of blackheads, sebum and/or other substances from skin, for skin tightening, skin lightening, anti-aging, anti-oxidant treatment and/or for any other type of treatment.

Delivery of Treatment Fluids and/or Other Materials

In some embodiments, in order to promote hair growth in a targeted portion of a subject skin (e.g., the subject's scalp), one or more treatment fluids and/or other materials can be delivered to, and preferably into (at least partially), a subject's skin tissue. For example, in some arrangements, growth factors can be delivered to the subject's skin surface. Growth factors can include, among other things, human-derived growth factors (e.g., FGF9 and other fibroblast growth factors (FGF), human fibroblast conditioned media and other fibroblast growth factors, epidermal growth factor (EGF)-related ligands, transforming growth factor-beta (TGF-beta), insulin-like growth factor (IGF), hepatocyte growth factor/scatter factor (HGF/SF), platelet-derived growth factor (PDGF), etc.), synthetic growth factors, liposome (courier) chemically altered growth factors, other human-derived and/or non-human derived growth factors and/or the like. In some embodiments, the growth factors that are delivered to a subject's skin tissue for hair growth purposes include, but are not limited to, human growth factors, synthetic or laboratory-derived growth factors and/or the like. In other embodiments, one or more other substances can be delivered to the subject's skin, either in addition to or in lieu of growth factors. For example, in some embodiments, one or more of the following can be delivered to a targeted area or portion of the subject's skin to help promote hair growth: growth factors, amino acids (e.g., leucine, isoleucine, valine, etc.), antioxidants, minoxidil, other antihypertensive vasodilators, finasteride, dutasteride, ketoconazole, spironolactone, flutamide, catechin, epicatechin, other phytochemicals, carnitine, rejuvaplex, copper peptides, other hair growth-stimulating agents, other pharmaceuticals and non-pharmaceuticals, plant-derived products, cleansing or pre-cleansing shampoos, other cleansing or pre-cleansing solutions (e.g., salicylic acid, GlySal™ (glycolic acid and salicylic acid mix), other acids, etc.), other natural and synthetic materials and/or the like.

According to some embodiments, regardless of the exact material(s) or substance(s) utilized or combination thereof, the delivery of agents and/or other substances and materials can advantageously assist with the growth of hair along a subject's targeted skin surface. In some embodiments, the delivery of such fluids and/or other materials can help improve the health of native and/or translated hair, as desired or required.

By way of example, fluids and/or other materials can be delivered to the targeted portion of a subject skin (e.g., the subject's scalp) using a handpiece assembly identical or similar to the one illustrated and discussed herein with reference to FIGS. 5 to 9. In other embodiments, any other device (e.g., handpiece assembly) or method can be used to deliver one or more fluids to targeted skin of a subject. In some arrangements, for instance, a handpiece similar or identical to the one illustrated in FIG. 1 herein can be used.

FIG. 1 illustrates one embodiment of a handpiece assembly 100 configured for use with a skin treatment system. As shown in FIG. 1, a handpiece assembly 100 can include a main body portion 110 configured to receive a tip 130 along its distal end 120. In some embodiments, the tip 130 is removably attached to the distal end of the main body portion 110. Alternatively, however, the tip can be permanently attached to the main body portion 110, as desired or required. The tip can include one or more abrasive features, surfaces and/or the like that are configured to selectively abrade skin when the handpiece assembly 100 is moved relative to a subject's skin. For example, the tip can include one or more posts, spiral members, other abrasive and/or sharp ridges or features and/or the like. Therefore, the tip can be configured to conduct the microdermabrasion of the targeted skin surface. Additional details regarding possible tip options that can be incorporated into any of the embodiments disclosed herein are provided in U.S. patent application Ser. No. 11/392,348, filed on Mar. 29, 2006 and issued as U.S. Pat. No. 8,048,089 on Nov. 1, 2011, the entirety of which is incorporated by reference herein and made a part of the present application.

With continued reference to FIG. 1, the handpiece assembly 100 can be sized, shaped and otherwise configured to receive one or more vials or cartridges 200. For example, as shown, the handpiece assembly can include a recess or other opening into which a vial 200 can be placed and secured. Such vials or other containers 200 can include one or more fluids and/or other materials that can be selectively delivered to the subject's skin surface during use in order to promote hair growth.

In some embodiments, one or more materials can be strategically embedded, impregnated, placed, stored and/or otherwise disposed on one or more surfaces or areas of the tip or other portion or component of the skin treatment system. Such materials can comprise solids, semi-solids, other dried substances, gels, concentrated solutions and/or the like. For example, such materials can be provided in loose form (e.g., positioned on or within a recess, other portion of the tip, within a cartridge or other container, adhered to one or more surfaces, etc.), as a tablet, capsule, pill, disc or other dissolvable solid, saturated within a foam pad or other sponge-like material and/or the like. Thus, in certain arrangements, water (e.g., distilled, tap water, filtered, etc.), saline, other dilutants and/or other fluids which are delivered to the tip can selectively dissolve, liquefy, melt, soften, dilute or otherwise prepare the materials embedded, impregnated and/or otherwise positioned on the tip, within a cartridge or other container and/or on or within another portion or component of a skin treatment system (e.g., handpiece assembly, fluid line upstream of the handpiece assembly, etc.). Accordingly, any desired hair growth materials or formulations can be advantageously provided to the skin surface being treated, as desired or required.

In addition, as illustrated in FIG. 1, the handpiece assembly 100 can be connected to a vacuum. For example, the waste conduit 180 of the handpiece assembly can be placed in fluid communication with a suction or vacuum source (not shown) in order to remove exfoliated skin, spent fluids, waste materials and/or other substances away from the treatment surface. As noted above, the handpiece assembly 100 can be configured to receive one or more removable tips 130, which may be selected based upon the specific procedure being performed, the desired result and/or any other considerations. The distal portion 120 of the handpiece assembly 100 can include one or more 0-rings 138 or other sealing members to prevent undesirable leaks between the main body portion 110 and the tip 130. Additional details regarding removable tips are provided in U.S. patent application Ser. No. 12/832,663, filed on Jul. 8, 2010 and published as U.S. Publ. No. 2011/0082415 on Apr. 7, 2011, the entirety of which is hereby incorporated by reference herein (see, for example and without limitation, FIGS. 5B and 8A through 16B of the referenced application).

With continued reference to FIG. 1, the handpiece assembly 100 can be configured to receive one or more types of vials or cartridges 200. For example, a vial 200 can include, without limitation, a standard or non-standard vial, ampoule or any other container. In some embodiments, hair growth agents and/or any other treatment fluids or materials contained within the cartridge 200 can be drawn toward the tip 130 using one or more suction sources (e.g., the vacuum source configured to remove waste materials from the tip). In other embodiments, the fluids and/or other materials contained within the cartridge (e.g., fluids and/or other materials configured to promote and/or stimulate hair growth) gravity flow toward the tip 130 or are conveyed with the help of a fluid transfer device. The cartridge 200 can be selectively removed from the handpiece assembly 100 when a desired volume or other amount of serum or other material has been delivered to the tip 130.

In some embodiments, a vacuum in fluid communication with the waste conduit 180 can be configured to remove waste materials from the tip 130 and help deliver serums, other fluids and/or any other materials from the vial or cartridge 200 to the tip 130. When the tip 130 is positioned against the subject's skin, suction created by the vacuum source can be transmitted to one or more fluid channels or conduits of the handpiece assembly 100. Such a suction force created within the corresponding channels or conduits of the handpiece assembly can remain intact as long as the tip 130 is maintained against or substantially against the subject's skin. Consequently, the suction force created by the vacuum source can be transferred to one or more fluid delivery channels of the assembly 100, thereby transferring fluids and/or other materials from the vial or other container toward the tip 130.

In some embodiments, serums, other fluids and/or other materials can be delivered to the tip 130 (e.g., from a cartridge, an external source, etc.) through one or more peripheral or other non-centrally located channels, conduits and/or other lines or fittings. For instance, in the handpiece assembly 100 illustrated in FIG. 1, such fluids and/or other materials can be routed through one or more internal channels of the assembly and/or waste conduits of the tip. Thus, in some embodiments, one or more of the channels, connectors and/or other hydraulic components may need to be reconfigured to adequately place the non-centrally located delivery openings of the tip in fluid communication with corresponding delivery lines of the handpiece assembly 100.

Figure 2:
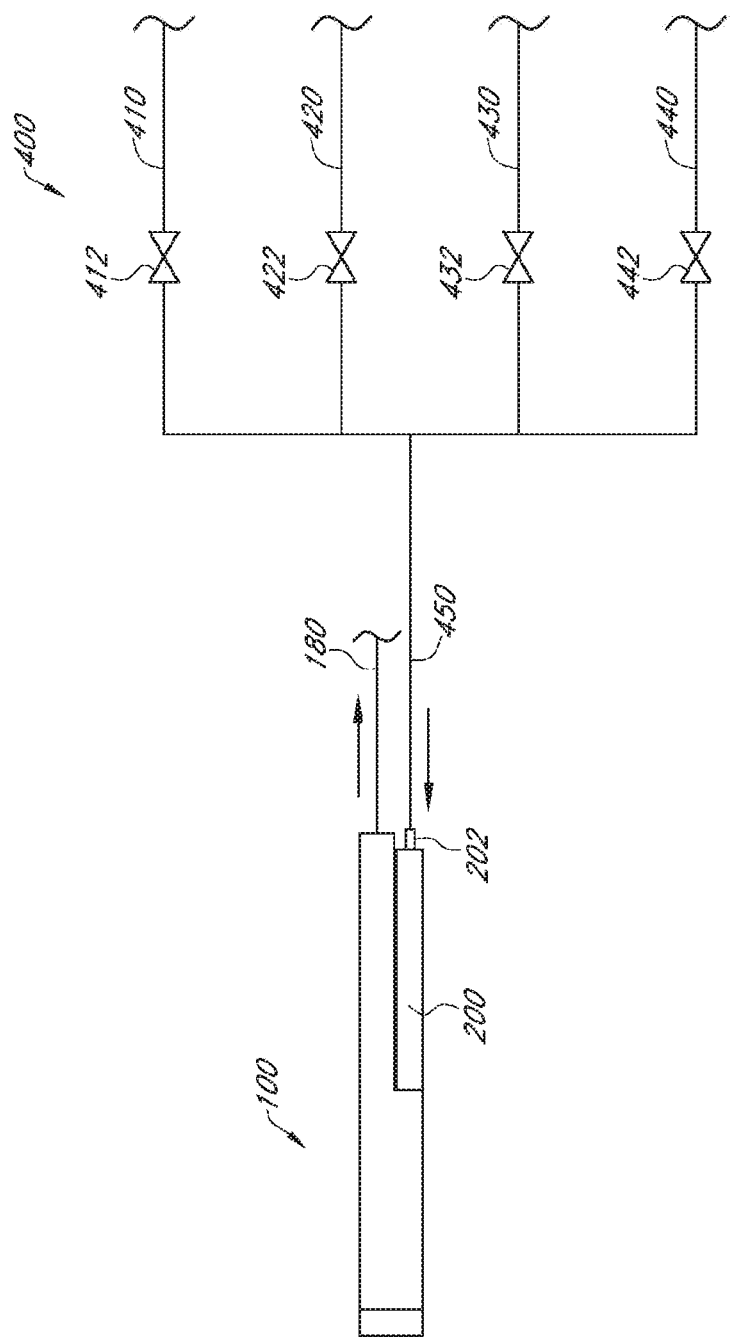
FIG. 2 schematically illustrates a handpiece assembly being in fluid communication with a fluid delivery system or manifold system according to one embodiment.

According to certain embodiments, as illustrated in FIG. 2, a vial, cartridge or other container 200 is placed in fluid communication with a manifold system 400 that may comprise a plurality of individual fluid conduits 410, 420, 430, 440. In turn, one or more of these fluid conduits 410, 420, 430, 440 can be in fluid communication with a separate container (not shown). For example, in some embodiments, such fluid conduits can be in fluid communication with containers of a tower system (see, e.g., FIGS. 9-11). In the illustrated embodiment, the individual fluid lines 410, 420, 430, 440 are in fluid communication with a main fluid conduit 450, which connects to a nozzle 202 along a proximal end of a vial or other container 200 secured within the handpiece assembly 100. One or more of the fluid conduits can comprise a valve 412, 422, 432, 442 or other flow control device or feature to selectively regulate the transfer of fluids and/or other materials (e.g., hair growth fluids and/or materials) to the handpiece assembly 100. In the illustrated arrangement, the manifold system 400 comprises a total of four fluid branches. However, a system can comprise more or fewer fluid branches (e.g., 1, 2, 3, 4, 5, 6, 7, 8, more than 8, etc.), as desired or required by a particular application or use.

According to certain embodiments, one or more of the fluid lines fluid conduits of the manifold system illustrated in FIG. 2 are configured to provide a serum, other treatment fluid and/or the like, including fluids and materials that are adapted to promote hair growth. Alternatively, however, one or more of the conduits can be configured to receive water (e.g., distilled, tap water, filtered, etc.), saline, other dilutants or dissolvents, other fluids and/or the like to the handpiece assembly 100. As discussed in greater detail herein, such fluids can be adapted to contact and dissolve, dilute, liquefy, soften and/or otherwise mix with one or more solids, gels and/or other materials positioned within or on various surfaces or portions of the handpiece assembly 100 (e.g., tip). This can provide a convenient method of providing one or more materials at the skin-tip interface and/or any other location where such materials are desired or required.

Suction/Vacuum

In some arrangements, vacuum, suction or negative pressure can be applied to a targeted skin surface (e.g., a subject's scalp) to facilitate the transmission, infusion, diffusion and/or progression of one or more treatment materials into skin surface, to stimulate blood flow along or near the targeted skin surface and/or to provide one or more other advantages or benefits. Consequently, the effectiveness of a hair growth procedure and the likelihood of success can be improved. Such vacuum can be applied using a handpiece that is specially-designed to engage the skin and provide such a vacuum force. For example, a handpiece that is identical or similar to an embodiment disclosed in any of the following applications can be used: U.S. patent application Ser. No. 12/346,582, filed Dec. 30, 2008 and issued on Jan. 1, 2013 as U.S. Pat. No. 8,343,116, U.S. patent application Ser. No. 11/392,348, filed Mar. 29, 2006 and issued on Nov. 1, 2011 as U.S. Pat. No. 8,048,089, U.S. patent application Ser. No. 12/832,663, filed Jul. 8, 2010 and issued on Aug. 26, 2014 as U.S. Pat. No. 8,814,836 and International Patent Application No. PCT/US2014/024992, filed Mar. 12, 2014 and published on Sep. 25, 2014 as PCT Publ. No. WO 2014/151104. As noted herein, the entireties of all of the foregoing are hereby incorporated herein. The embodiments discussed herein with reference to FIGS. 1 and 2 provide example systems that utilize vacuum to assist in the delivery of fluids and other treatment materials from one or more containers (e.g., vials, bottles includes in a tower or manifold system, etc.) to the skin interface.

The use of such handpieces and/or other devices or systems can provide one or more benefits or advantages during a treatment (e.g., hair growth promotion or strengthening) procedure. For example, the delivery of suction or vacuum to the targeted skin surface can facilitate blood flow to the targeted skin surface (e.g., the superficial and/or deep layers or tissues at, near or adjacent the targeted hair growth area). This can, in certain circumstances, therapeutically benefit the targeted tissue to help create an environment where the likelihood of hair growth can be improved. In addition, the delivery of fluids and/or other materials (e.g., growth factors, amino acids, antioxidants, Minoxidil, other antihypertensive vasodilator agents, other hair growth-stimulating agents, other natural or synthetic materials, etc.) deeper into the targeted skin tissue can be further enhanced by the use of vacuum or suction.

Pressure & Pulsing and Positive Pressure with Vacuum

In some embodiments, the infusion or transfer of fluids within targeted skin tissue can be enhanced using the delivery of pressure (e.g. the application of force, either constant or intermittent) and/or mechanical pulsing of the tissue surface. For example, a handpiece assembly and/or other device or system can be used to deliver pulsed air to a targeted skin tissue of a subject (e.g., the subject's scalp, other skin region where hair growth is desired, etc.). In some embodiments, the use of pressure, pulsing and/or similar technologies can assist with the delivery of treatment fluids and/or substances deeper into skin tissue to facilitate a treatment procedure (e.g., a hair growth promotion protocol or method). In such arrangements, the use of mechanical force (e.g., via pressure, pulsing, etc.) can help push or drive treatment fluids and/or other substances delivered to or near the tip of a handpiece or other device or system deeper into skin tissue. In some embodiments, the ability to deliver at least a portion of treatment fluid and/or other materials deeper into skin tissue can facilitate the overall process and help promote health and hair growth ability in such tissue.

According to some arrangements, a device or system that is configured to deliver air at a desired pulse rate or frequency can be used to help "drive" treatment fluids and/or other materials deeper into a targeted skin surface (e.g., the subject's scalp). Additional details regarding the use of pulsing (e.g., air-based pulsing) are provided in International Patent Application No. PCT/US2014/024992, filed Mar. 12, 2014 and published on Sep. 25, 2014 as PCT Publ. No. WO 2014/151104, the entirety of which is hereby incorporated herein.

FIGS. 3A to 4E illustrate non-limiting embodiments of handpiece assemblies that are configured to provide one or more fluids and/or other treatment materials (e.g., hair growth promoting agents) to a skin interface in conjunction with air delivery (e.g., pulsing) and/or needling.

According to some embodiments, as discussed herein, the effectiveness of performing a treatment procedure (e.g., hair growth stimulation procedure) can be enhanced by the delivery of mechanical agitation to the skin surface being treated. For example, air or other fluid can be selectively pulsed or otherwise delivered to the skin surface at the same time that exfoliation and/or treatment fluid delivery occurs. In other embodiments, other forms of mechanical energy (e.g., acoustic energy, needle penetrations, etc.) can be used, either in lieu of or in addition to fluid delivery. This can be conducted concurrently with a skin treatment procedure and/or before or after a skin treatment procedure as desired or required. As noted above, in some embodiments, it may be beneficial to provide air or other fluid to the skin surface being treated. The air can be delivered at a particular flowrate, pressure, intensity, pulsing rate or frequency and/or time duration to help achieve a particular effect on the skin surface. For example, air or other fluid can be pulsed onto the skin during, before and/or after a microdermabrasion procedure to promote and facilitate the transfer of serums, other liquids and/or other materials at least partially into the subject's skin tissue. In some embodiments, air pulsing can comprise square wave pulsing (e.g., having sequential air delivery and no air delivery phases, one after another, etc.).

In some embodiments, air is delivered through the air delivery passage in individual puffs. Accordingly, depending on their volume, intensity, pressure and/or other properties, such puffs can help exert an intermittent force along the subject's skin. As noted above, such mechanical or pneumatic agitation of the skin can provide one or more benefits. For example, the resulting force or pressure on the skin can help drive serums, liquids and/or other substances being delivered to the tip (e.g., via the fluid delivery passage) deeper into the skin tissue. The repetitive agitation created by the air puffs can also help loosen dirt, oils and/or other unwanted materials from the pores along the skin surface being treated.

A handpiece assembly configured to deliver air or other gas during a skin treatment procedure can be configured to allow a user to adjust the manner in which air is delivered through one or more air delivery passages and/or the amount of negative pressure that is applied by the vacuum source through the suction passage (e.g., or the amount negative pressure that is realized along the tip). In some embodiments, the negative pressure within the suction passage is sufficiently high to maintain contact between the subject's skin and the peripheral and inner lips during use. This can help maintain a steady and consistent flow of treatment fluids to the working surface while a skin surface (e.g., a subject's scalp or other skin region where hair growth is desired) is exfoliated or otherwise treated. A sufficiently high vacuum along the tip can also help ensure that the lips will not lose contact with the skin surface as air is delivered (e.g. in puffs) to the skin surface.

According to some embodiments, one or more needles or other piercing members can be used to agitate and/or penetrate certain areas or regions of the subject's skin, before, during or following a microdermabrasion or other skin treatment procedure. The needles or other penetrating members can be moved in and out of adjacent skin tissue over a period of time. Consequently, a plurality of the small diameter passages can be created in the targeted skin tissue, at least temporarily. Such passages can allow serums, other treatment agents and/or other substances that are delivered or otherwise applied to the skin to be advantageously carried deeper into the skin tissue.

FIGS. 3A-3E illustrate various views of another embodiment of a skin treatment device 3200 comprising a main body 3210 and a tip 3240 positioned along the distal end of the main body. In some embodiments, the tip 3240 can be removably secured to the main body 3210. As illustrated in frontal view of FIG. 3B, the tip 3240 can comprise an outer or peripheral lip 3260 that is configured to contact the skin surface (e.g., a subject's scalp) when the device 3200 is properly positioned relative to the subject's skin. The tip 3240 can additionally include an interior lip or ridge 3252 that is also configured to contact the skin surface being treated (e.g., simultaneously with the outer or peripheral lip or ridge 3260.

Figure 3A:
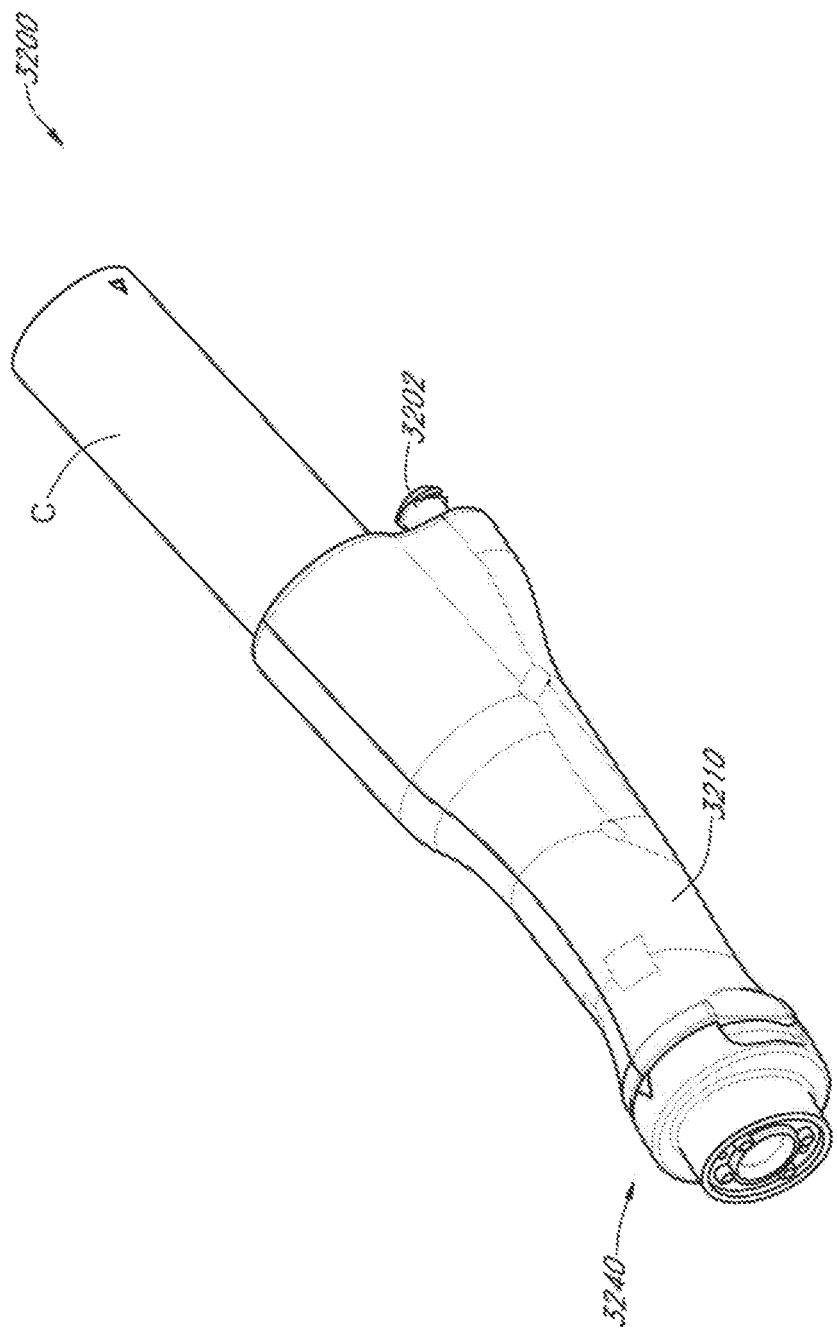
Figure 3B:
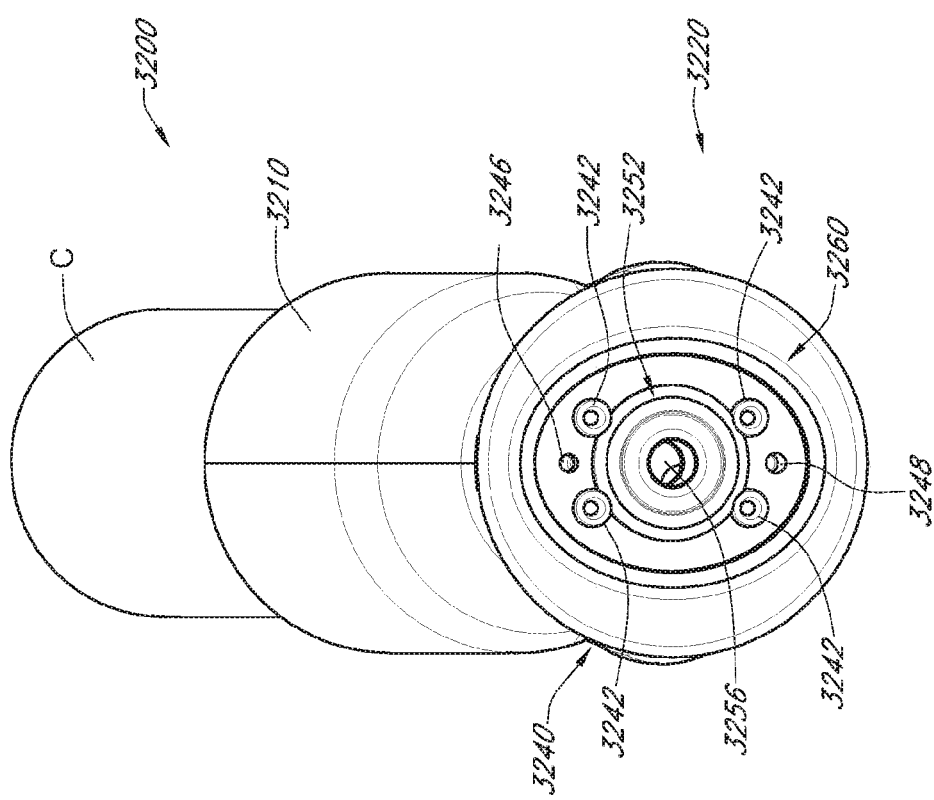
Figure 3D:
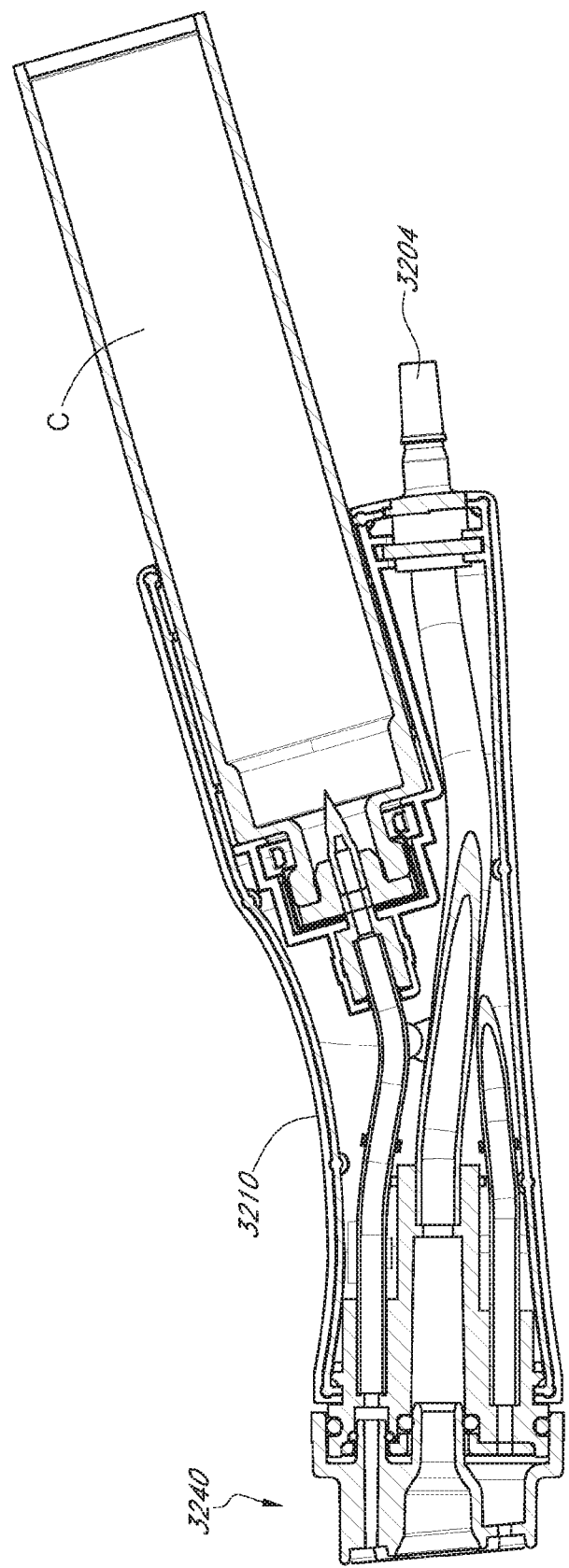
Figure 3E:
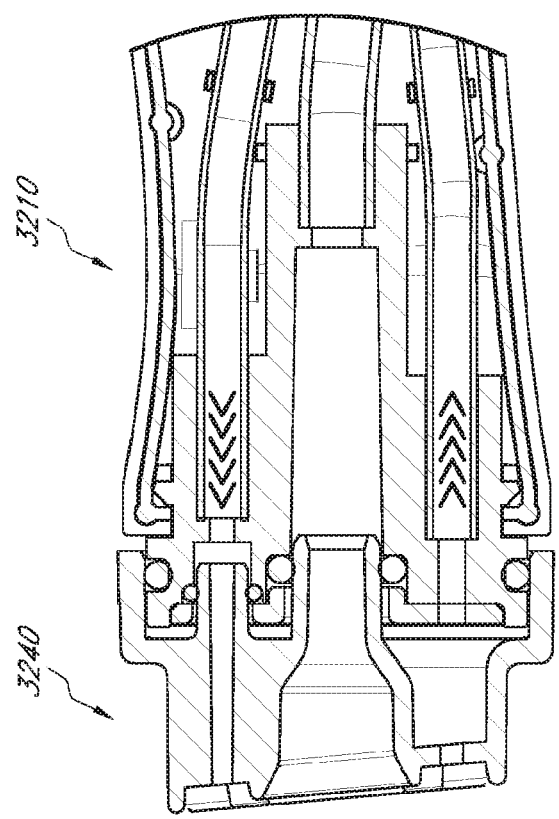

With continued reference to FIG. 3B, the generally annular area defined between the outer and inner lips or ridges 3260, 3252 can include one or more openings or ports. For example, as shown, the annular area can include one or more vacuum or suction ports 3242. In some embodiments, such ports 3242 comprise posts or other members that extend above the bottom surface of the annular region. As shown in FIG. 3B, the vacuum or suction ports 3241 can be strategically positioned adjacent or near (e.g., immediately surrounding) the inner ridge 3252. Such a configuration can assist to maintain contact between the lips or ridges 3260, 3252 and the subject's skin surface when the device 3200 is in use. The ability to consistently and adequately maintain contact between the tip and the subject's skin can be challenging when air or other fluid is being pulsed through the central opening 3256 of the tip, during use. As can be appreciated, the delivery of positive air pressure during pulsing can urge the tip (e.g., especially the inner lip 3252 and surrounding structures) to lose contact with the skin (e.g., the subject's scalp or other skin region where hair growth is desired). Therefore, the system can be configured to provide sufficient suction or vacuum along, near or adjacent the pulsing port 3256 to ensure that proper skin contact is maintained during use of the device. In other configurations, the suction ports or openings 3242 can be flush, generally flush and/or recessed relative to the bottom surface of the annular region of the tip. Further, the shape, size, orientation, spacing, location, quantity and/or other characteristics of the ports or openings 3242 can be different than illustrated in FIG. 3B, as desired or required.

As illustrated in FIG. 3B, the annular region defined between the two lips or ridges 3260, 3252 can also include one or more fluid delivery ports 3246 and/or additional vacuum or suction ports 3248. In one embodiment, as illustrated in FIG. 3B, a single fluid delivery port 3246 is generally opposite of a vacuum or suction port 3248, facilitating in the delivery of a treatment fluid across a larger surface area of the skin being treated. In other embodiments, the quantity, orientation, location, size, shape and/or other details about fluid delivery ports and/or additional suction ports can vary.

With continued reference to FIG. 3B, the region defined within the interior of the inner lip 3252 includes an opening 3256 that is in fluid communication with one or more passages that extend through an interior of the device 3200. As discussed in greater detail herein, such an opening 3256 can be used to selectively provide pulsed air or other fluid to the skin during a treatment procedure.

As shown in FIGS. 3B and 3C, the pulsing opening 3256 of the tip can be placed in fluid communication with a pulsing fluid connector 3204 toward the distal or rear portion of the device 3200 (e.g., via one or more interior lumens, conduits or other passages). Such a connector 3204 can be coupled to a pulsed air source, either directly or indirectly, to selectively deliver air to the tip and the skin surface at a desired frequency, duty cycle, volume and/or the like. As discussed, the delivery of such pulsed air or other fluid can assist with a deeper penetration of treatment fluids into the skin surface, thereby enhancing a skin treatment procedure (e.g., a hair growth procedure). For example, in some embodiments, the mechanical agitation of the pulsing of air can drive, push or otherwise force treatment fluids that have been delivered to the skin surface deeper into the skin.

According to some embodiments, one or more parameters related to the pulsing of air or gases in the device 3200 can be adjusted by a user, as desired or required. For example, in some embodiments, the high and low pressure levels during a pulsing sequence can be modified. As noted above, the low pressure level can be zero, positive or above zero, or negative or below zero (e.g., with respect to atmospheric pressure). Thus, in some embodiments, air is pulsed between positive and negative (e.g., suction) pressures during a specific cycle. In other embodiments, both high and low pressure levels can be above atmospheric. Thus, a pulsing cycle does not need to include a vacuum or suction phase. In other embodiments, the low pressure level is zero or around zero. These pulsing options can be applied to any embodiments disclosed herein that are configured or can be configured to be used with pulsed air delivery to the skin interface (e.g., for improved serum penetration into the targeted skin surface, such as a subject's scalp).

Although not illustrated in the embodiment of FIGS. 3A-3E, a tip 3240 that is configured to permit the pulsing of air along a skin interface can additionally comprise one or more abrading members (e.g., posts, spiral, ridges, brushes, sharp edges, roughened surfaces, etc.). Thus, in some embodiments, while the device 3200 is activated (e.g., during the delivery of pulsed air and/or during the maintenance of suction through corresponding vacuum ports, etc.), the user can selectively translate or move the tip of the device relative to the targeted skin surface to at least partially abrade and/or otherwise treat the skin (e.g., scalp, other skin region where hair growth is desired, etc.).

However, in other embodiments, the device 3200 comprises a non-abrading tip 3240 for the purpose of driving serums and/or other fluids deeper into the skin. This can be performed as part of a preliminary, intermediate (e.g., secondary) or follow-up (e.g., tertiary) step in a treatment process or protocol, as desired or required. For example, in some embodiments, such a non-abrading device is used (and the corresponding method is utilized) following an abrading or preparatory procedure, step or phase.

With continued reference to FIGS. 3A-3E, device 3200 can be configured to be placed in fluid communication with one or more serums and/or other treatment fluids contained in a cartridge C. As shown, such a cartridge can be secured within a corresponding recess of the handheld device 3200, which in the depicted arrangement is located along the distal end of the device. In other embodiments, however, the device can include a port along its distal end (or along any other portion). Such a port (not shown in the illustrated arrangement) can be placed in fluid communication with a main fluid delivery line. In some embodiments, for example, such a main fluid delivery line or conduit can be configured to deliver serums and/or other fluids from a manifold system, such as the one disclosed herein with reference to FIG. 2.

As shown in FIG. 3C, the handheld device 3200 can include additional ports 3202, 3204 for connecting to a vacuum source and/or a pulsed air source. Such fluid sources can be separate from the treatment system or may be at least partially incorporated into the system, as desired or required. In some embodiments, at a minimum, the vacuum and pulsed air sources are in data communication with a control module or other controller to permit a user of the device to advantageously regulate the level of suction and/or the level of pulsing during use.

According to some embodiments, the pulsed air concepts can be combined with a movable needle assembly that is configured to selectively penetrate skin. A system that combined needle penetrations with pulsed air delivery can provide more enhanced (e.g., deeper) infusion or penetration of serums and/or other liquids being delivered to the skin surface being treated (e.g., a subject's scalp). One embodiment of a combination needle penetration and pulsed air delivery device 3300 is illustrated in FIGS. 4A-4E. As discussed above with reference to FIGS. 3A-3E, the device 3300 can include an inner lip or ridge 3352 and an outer lip or ridge 3360. Such lips or ridges 3352, 3360 can be shaped, sized and otherwise configured to contact a skin surface when tip 3340 of the device 3300 is properly positioned against a subject.

Figure 4A:
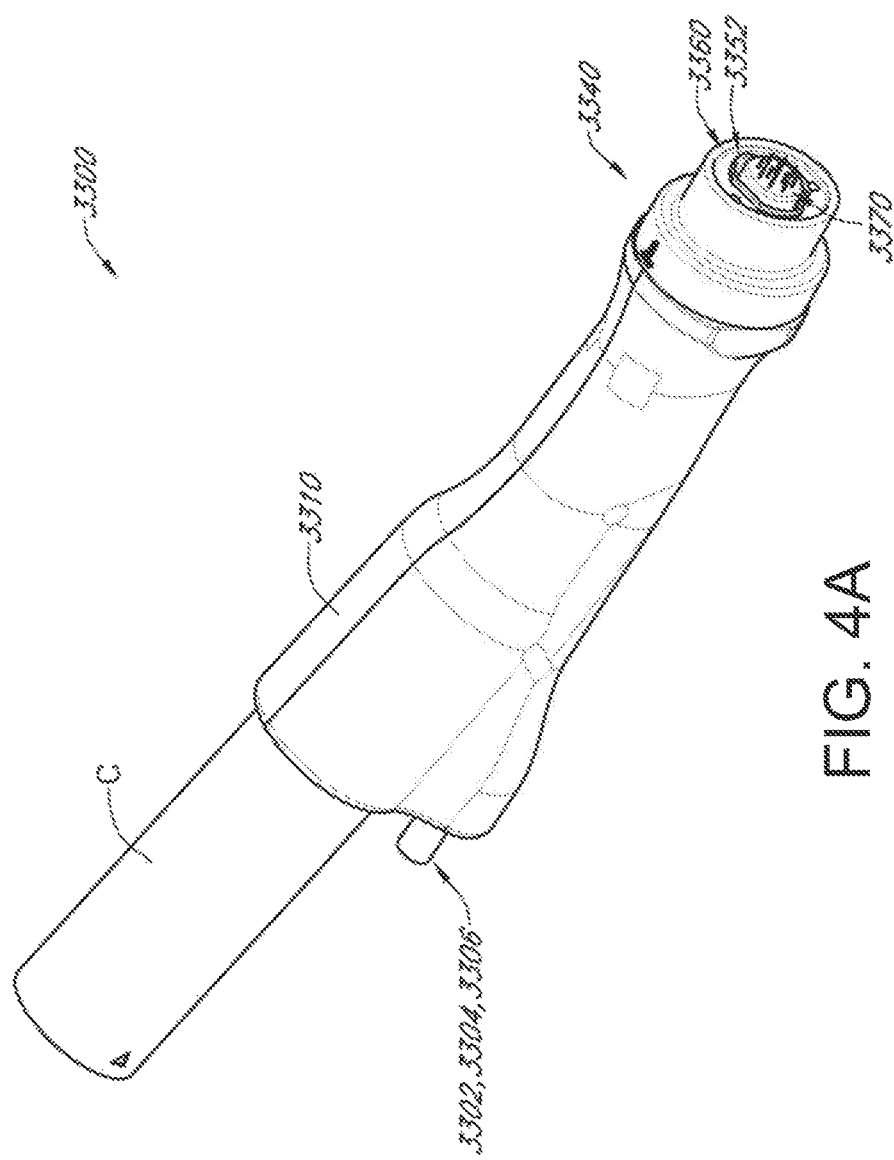
FIGS. 4A-4E illustrate various views of a system comprising air pulsing and needle penetration, according to one embodiment.
Figure 4B:
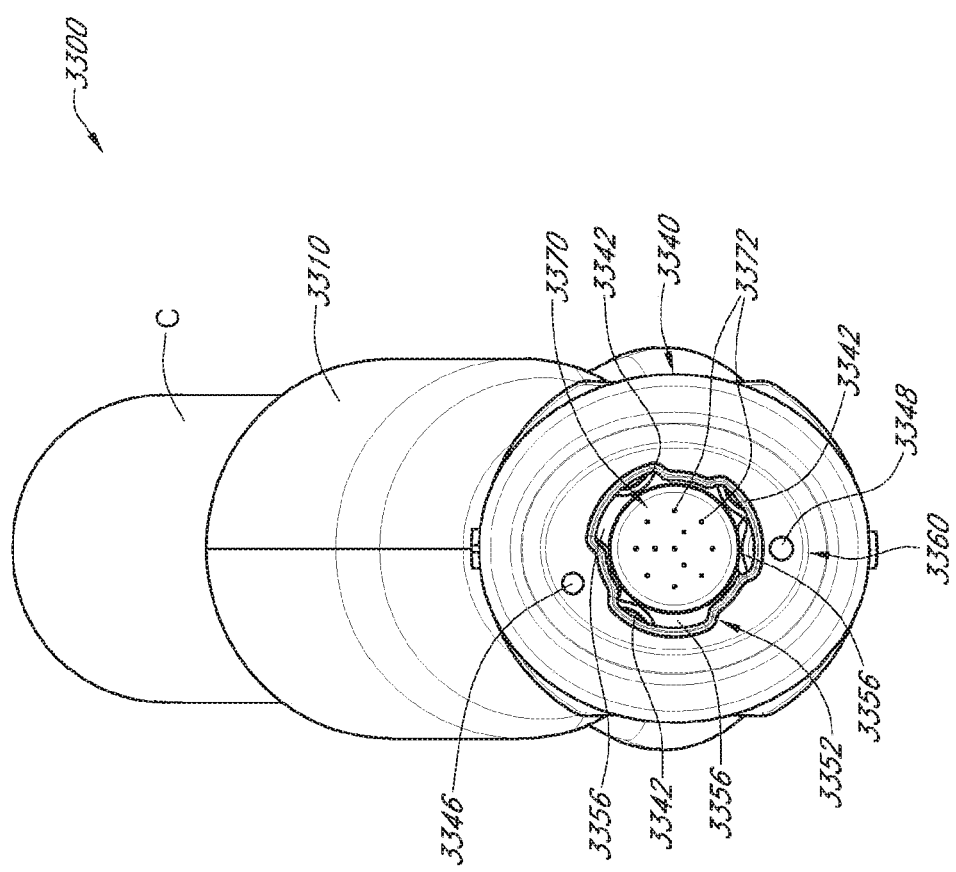

With reference to front view of the tip in FIG. 4B, as with other device embodiments disclosed herein, the area or space extending between the inner and outer lips or ridges 3352, 3360 can be configured to receive one or more treatment fluids when the device is in use. For example, when the lips or ridges 3352, 3360 contact a skin surface and a vacuum or suction source is activated, serum and/or other liquid from a fluid source (e.g., a cartridge C, as illustrated in FIGS. 4A-4E, a main fluid conduit that is coupled to a manifold system, etc.) can be delivered through one or more fluid delivery ports 3346 located between the ridges 3352, 3360. Spent fluid and/or other debris can be removed from the tip and the skin/device interface through a vacuum opening 3348, which, in the illustrated arrangement, is also located between the ridges 3352, 3360. As discussed above with reference to the device of FIGS. 3A-3E, the fluid delivery port 3346 and the suction or vacuum port 3348 can be spaced apart from each other by a desired separation distance, which can help ensure that the serums and/or other fluids that are delivered to the skin pass along at least a portion of the tip before being removed. In some embodiments, this can provide for longer contact time between the serums and/or other liquids and the skin, which can result in a better treatment outcome.

With continued reference to FIG. 4B, the inner ridge or lip 3352 can include one or more openings or passages 3356 that are adapted to provide pulsed air to the region defined by the ridge 3352. In the depicted embodiment, there are three separate openings or opening sections 3356 contained within an interior of the inner ridge or lip 3352. However, in other embodiments, the inner ridge can include more or fewer openings or opening sections, as desired or required. Pulsed air or other gas can be selectively provided through such openings 3356 to create a desired puffing or air-driven effect on the skin, as discussed in greater detail herein with reference to other air pulsing arrangements. In some embodiments, in order to maintain proper contact between the inner and outer ridges 3352, 3360 and the skin surface of the subject during use, one or more vacuum or suction ports 3342 can be strategically positioned along or near the inner ridge. Thus, the use of such suction can help prevent or reduce the likelihood of disengagement between the inner ridge 3352 and the skin surface being treated during use.

As shown in FIGS. 4A-4E, the device can additionally include a movable needle assembly 3370 within an interior portion of the tip 3340. In the illustrated embodiment, a single movable needle assembly is positioned along a central portion of the tip (e.g., within an interior of the inner ridge or lip 3352. However, in other embodiments, the size, shape, location, quantity and/or the details regarding the movable needle assembly 3370 can vary, as desired or required. The needle assembly can include a plurality of needles 3372 that extent outwardly (e.g., in a distal direction).

According to some embodiments, the needle assembly 3370 can be configured to reciprocate between proximal and distal positions during use. In some embodiments, the reciprocation or other movement of the needle assembly 3370 is accomplished pneumatically or mechanically. For example, in one embodiment, an air or other fluid line is coupled, at least partially, with a receptacle or housing in which the needle assembly 3370 is positioned. The delivery of positive and/or negative fluid pressure relative to the movable needle assembly 3370 (e.g., and/or a related receptacle or housing) can be used to move the needle assembly 3370 in a desired manner. In some embodiments, the movable needle assembly 3370 can be spring loaded (e.g., using a spring or other resilient member or assembly S located within the handpiece. Thus, in such configurations, the needle assembly 3370 can be resiliently biased in a retracted (or proximal) orientation by the spring or other resilient force. The exertion of a pressure or force on the needle assembly 3370 (e.g., using the selective delivery of air relative to the assembly 3370) can help displace the needle assembly 3370 away from its resiliently retracted position to a more distal orientation against the spring or biasing force. Once the force on the movable needle assembly is terminated, the needle can assume its retracted, proximal position.

According to some embodiments, the extent to which the needle assembly is moved distally can be precisely controlled. For example, the degree to which the needle assembly is advanced can depend on the spring force of the spring or other resilient member, the amount of force that is applied to the assembly 3370 and/or the like. Accordingly, such parameters can help control the depth of needle penetration into the scalp or other skin surface caused by the needle assembly 3370. Depth of needle penetration and the resulting effect on the subject's skin tissue (e.g., a subject's scalp) can also be altered using other methods. For example, the device 3300 can be provided to a user with a variety of tip options, each of which has a different maximum penetration distance (e.g., by varying the length, diameter, sharpness and/or other characteristics of the needles 3372 included in the assembly 3370). In some embodiments, the user is permitted to alter the maximum needle penetration distance by manipulation the tip and/or needle assembly. For example, in some embodiments, the height of the lips or ridges can be adjusted. In other arrangements, the user can change the orientation (e.g., depth) of the needle assembly within the handpiece to effectively modify the penetration depth.

In some embodiments, a user presses a button or manipulates one or more other controllers or features (e.g., switch, foot pedal, etc.) to selectively deploy the needle assembly 3370 distally (e.g., toward the skin surface). For example, in a pneumatically-controlled needle assembly configuration, the user can press a button to permit pressurized air to enter into the corresponding conduit of the handpiece so as to exert a force on the needle assembly. As a result, the needle assembly can be moved toward the skin. If sufficient force is applied to the needle assembly, the needle assembly may move sufficiently far (e.g., in the distal direction) to engage and at least penetrate an adjacent skin surface of the subject.

In other embodiments, the manipulation of a button or other controller can actuate a mechanically-generated force on the needle assembly 3370 to move the assembly distally against a spring or other resilient force. In yet other arrangements, the needle assembly is not resiliently biased (e.g., does not include a spring or other resilient member). For example, the movable assembly can moved between a proximal and a distal position using a motor, gear and/or the like. Regardless of the manner in which the needle assembly is moved toward and away from the skin surface of the subject, in some arrangements, the assembly can be moved along several different proximal/distal positions. In some embodiments, available positions can be distinct (e.g., only at certain distances) or continuous (e.g., along any position between fully retracted and fully extended), as desired or required.

In some embodiments, during use, the movable needle assembly 3370 can be actuated (e.g., to move distally to and through a skin surface) only when the treatment device 3300 is not being translated or moved relative to the subject's skin (e.g., a subject's scalp). Such a method of using these devices can help avoid undesirable harm to the subject. The use of needles to create passages within the one or more layers of skin being treated can provide additional benefits to the subject. For example, serums and/or other fluids delivered and/or otherwise located along the tip of the device can penetrate the subject's skin to a deeper extent. Such advantages and benefits can be further enhanced by the simultaneous air pulsing on the skin tissue.

Figure 4C:
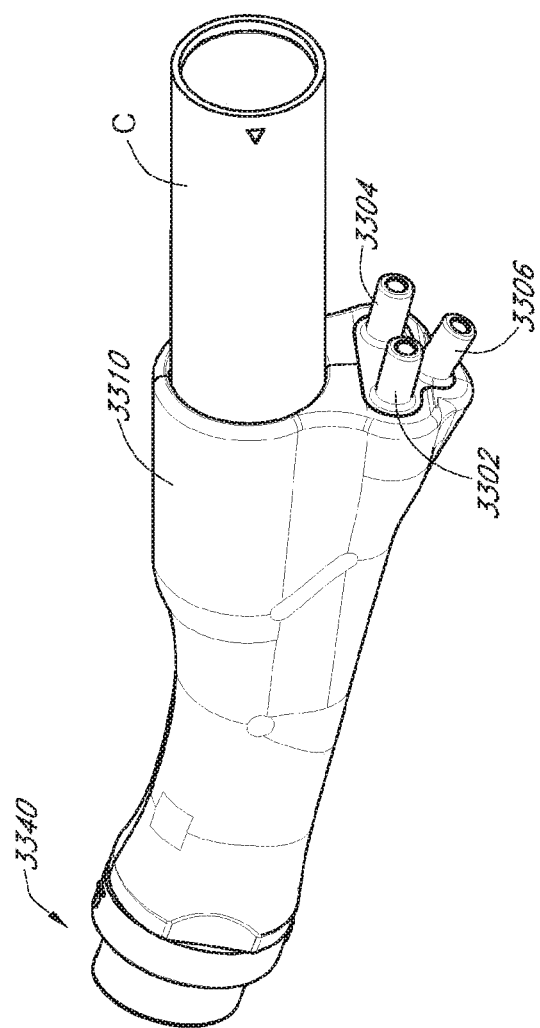
Figure 4D:
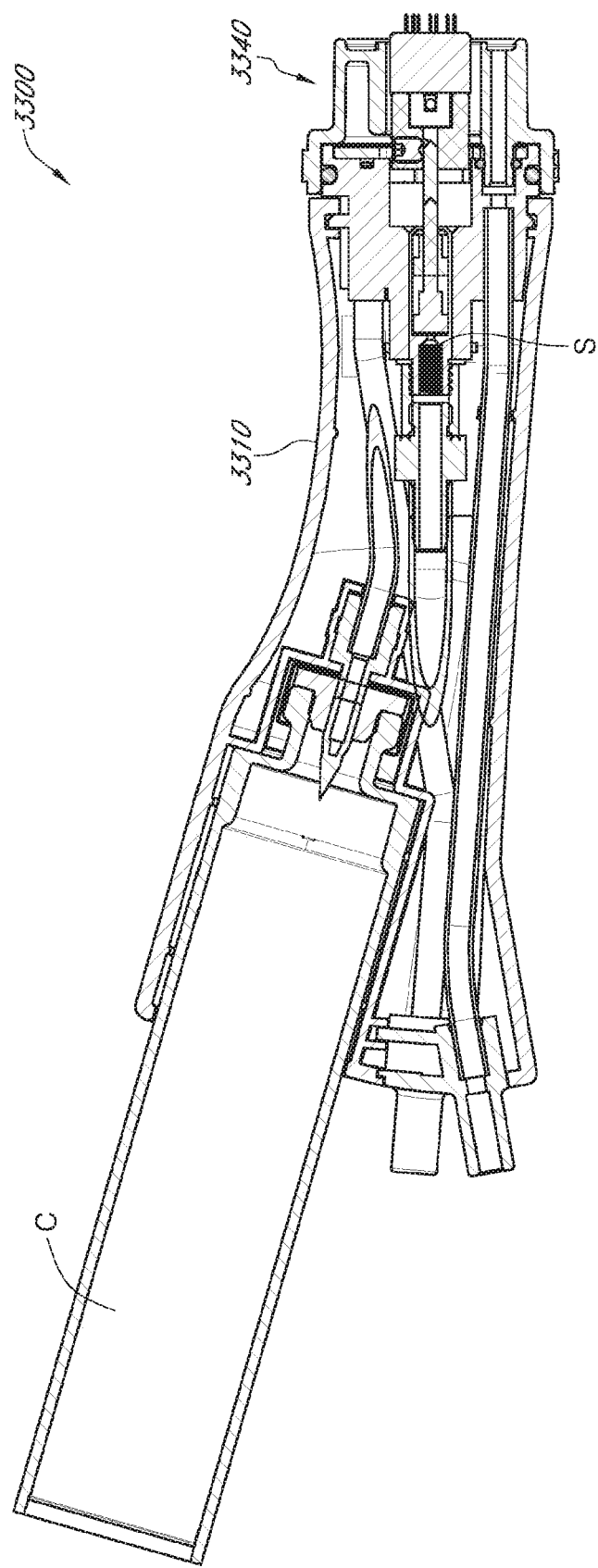
Figure 4E:
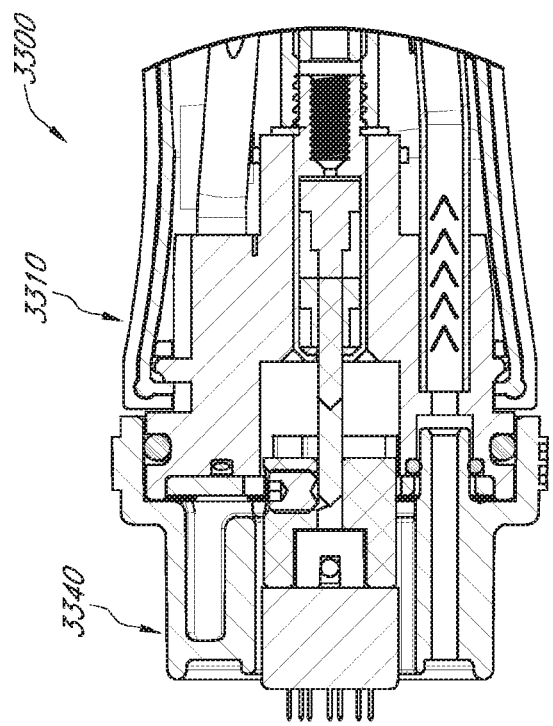

As shown in FIG. 4C, the device 3300 can include additional ports 3302, 3304, 3306 for connecting to a vacuum source (e.g., to the suction port), an air supply line (e.g., to the movable needle assembly; for selectively pneumatically actuating the assembly) and/or a pulsed air source (e.g., for providing pulsed air to the tip of the device). Such fluid sources can be separate from the treatment system or may be at least partially incorporated into the system, as desired or required. In some embodiments, at a minimum, the vacuum, air supply and pulsed air sources are in data communication with a control module or other controller to permit a user of the device to advantageously regulate the level of suction, position of the needle assembly and/or the level of pulsing during use. In some embodiments, the button or other controller associate with movement of the movable needle assembly can be coupled or incorporated into a valve structure in order to regulate the delivery of air or another gas to the assembly.

According to some embodiments, the needles 3372 of the needle assembly 3370 can be solid or hollow. In some embodiments, the needle diameter is 0.001-0.050 inches (e.g., 0.010 inches, 0.001-0.005, 0.005-0.010, 0.010-0.020, 0.020-0.030, 0.030-0.040, 0.040-0.050 inches, diameters between the foregoing ranges, etc.). In other embodiments, the needle diameter is less than 0.001 inches or greater than 0.050 inches (e.g., 0.050-0.060, 0.060-0.070, 0.070-0.080, 0.080-0.090, 0.090-0.100 inches, diameters between the foregoing ranges, greater than 0.100 inches, etc.). In some embodiments, the needle length is 0.05-5 mm (e.g., 0.5-2.5, 0.05-0.1, 0.1-0.2, 0.2-0.3, 0.3-0.4, 0.4-0.5, 0.5-0.6, 0.6-0.7, 0.7-0.8, 0.8-0.9, 0.9-1.0, 1-2, 2-3, 3-4, 4-5 mm, lengths between the foregoing ranges, greater than 5 mm, etc.).

In any of the embodiments disclosed herein that incorporate a needle assembly specially or any needle penetration technologies generally, the needles can be solid and/or hollow. In some embodiments, the needles can be configured to be selectively heated or cooled. For example, in one embodiment, the needles can be heated using resistive heating (e.g., via electrical energy, radiofrequency energy, etc.), using vapor (e.g., hot vapor) or similar techniques, thermoelectric devices and/or the like.

In any of the treatment embodiments disclosed herein, one or more pulsing parameters can be modified to create a desired effect on the subject's skin. For example, as noted above, the high and low pulse pressures can be adjusted. Further, in some embodiments, the duty cycle, frequency, air flowrate and/or other properties can be modified, as desired or required. For example, the duty cycle can be modified between 20 and 60% (e.g., 20-25, 25-30, 30-35, 35-40, 40-45, 45-50, 50-55, 55-60%, duty cycles between the foregoing ranges, etc.). In other embodiments, the duty cycle for the pulsed air system is greater than 60% (e.g., 60-70, 70-80, 80-90, 90-95%, duty cycles between the foregoing, greater than 95%, etc.) or less than 20% (e.g., 0-5, 5-10, 10-15, 15-20%, duty cycles between the foregoing ranges, etc.).

According to some embodiments, for any of the arrangements disclosed herein, the frequency of the pulsed air can vary between 2 and 15 Hz (e.g., 2-3, 3-4, 4-5, 5-6, 6-7, 7-8, 8-9, 9-10, 10-11, 11-12, 12,-13, 13-14, 14-15 Hz, frequencies between the foregoing ranges, etc.). In other embodiments, however, the frequency of pulsed air can be less than 2 Hz (e.g., 0-0.5, 0.5-1, 1-1.5, 1.5-2 Hz, frequencies between the foregoing ranges, etc.) or greater than 15 Hz (e.g., 15-20, 20-25, 25-30, 30-40, 40-50 Hz, frequencies between the foregoing ranges, greater than 50 Hz, etc.).

In other embodiments, an air-based pressure or force along the distal end of a handpiece or other device can be applied to push at least a portion of a treatment fluid or other material deeper into the skin surface. For example, a continuous delivery of air, a hammering or other mechanical impact device and/or the like can be used to help accomplish deeper infusion of fluids and/or other materials into the skin, promote blood flow and/or provide one or more other effects that may promote or otherwise facilitate hair growth along the targeted skin tissue, as desired or required.

In some embodiments, the pulsing (e.g., pneumatic, mechanical, etc.) along a distal end of a handpiece or other system can comprise alternating amounts of positive pressure (e.g., relative to atmospheric). Alternatively, the pulsing can include a first stage where a positive pressure is created (e.g., by air deliver, by mechanical or pneumatic impact, etc.) and a second stage where a negative pressure (or vacuum) is created. Such first and second stages can be alternates according to a desired or required frequency, which may be adjustable by a user.

In other arrangements, a handpiece or other treatment device or system is configured to simultaneously (as opposed to sequentially, as described in the above embodiments) deliver both positive and negative (vacuum) pressure to the skin interface. For example, in some embodiments, the distal end or tip of a handpiece assembly can be configured to separately create one or more positive pressure zones and one or more negative pressure (or vacuum) zones along its interface with the adjacent skin tissue of the subject being treated. Additional details related to these embodiments are disclosed in International Patent Application No. PCT/US2014/024992, filed Mar. 12, 2014 and published on Sep. 25, 2014 as PCT Publ. No. WO 2014/151104, the entirety of which is incorporated by reference herein.

Improved Handpiece Designs

Figure 5:
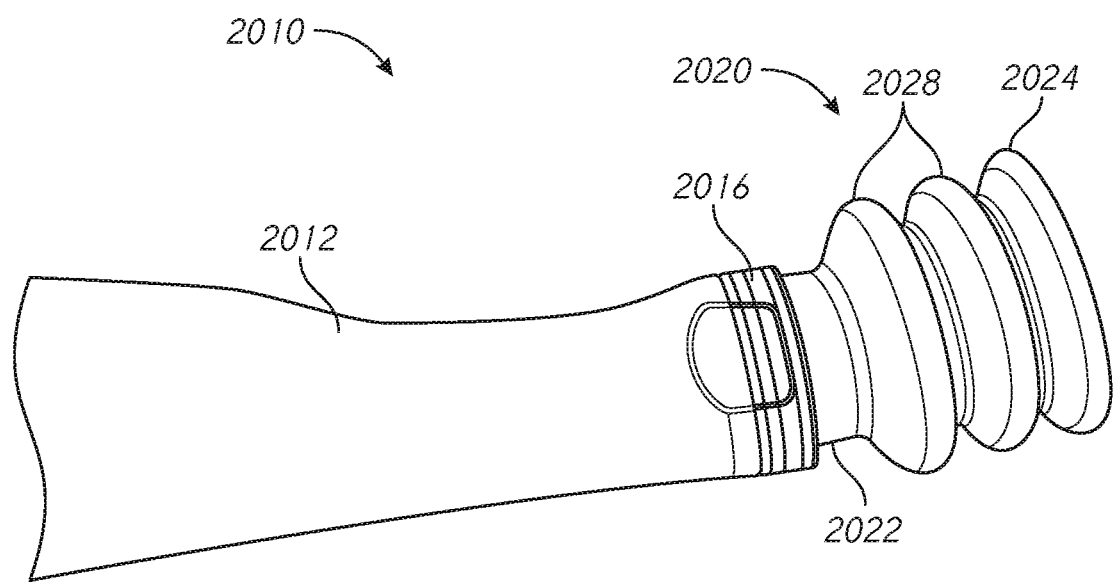
FIG. 5 illustrates a side view of a handpiece assembly having an engagement member or shroud along its distal end.

In some embodiments, as illustrated in FIG. 5, a handpiece assembly 2010 can include a flexible engagement member or shroud 2020 located along the distal end of the handpiece assembly 2010. As shown in FIG. 5, the engagement member 2020 can be secured or otherwise coupled to a tip 2016 that is configured to be removably secured to the distal end of the main body portion 2012 of the assembly 2010. In other embodiments, however, the engagement member 2020 and/or the tip 2016 can be fixedly secured to the main body portion 2012 of the handpiece assembly 2010. In yet other configurations, the engagement member 2020 can be sized, shaped and otherwise adapted to be removably or fixedly coupled to the main body portion 2010 (e.g., with or without a tip), as desired or required. In several embodiments, the main body portion 2010, the tip 2016 and/or the engagement member 2020 can form a unitary or monolithic structure. For example, some or all of the various components of the handpiece assembly 2010 can be combined into a single component or structure.

Regardless of its exact structure and/or design, the engagement member or shroud 2020 can be configured to engage a portion of a subject' skin and at least temporarily seal thereto. For example, in some embodiments, the engagement member 2020 can be configured to engage one or more contoured portions of a subject's scalp, face or other skin surface being treated. The engagement member 2020 can comprise one or more materials and/or features or configurations that facilitate the distal end of the engagement member 2020 contacting and adapting to the targeted skin surface. For example, the engagement member 2020 can comprises rubber (e.g., silicone rubber) and/or other elastomeric materials. As shown in FIG. 5, the engagement member 2020 can include one or more bellows or other portion, feature, component and/or configuration that is adapted to facilitate deformation of the engagement member 2020 such that it can contact and engage a targeted skin surface of a subject (e.g., a subject's scalp, face, etc.), as desired or required.

Figure 9:
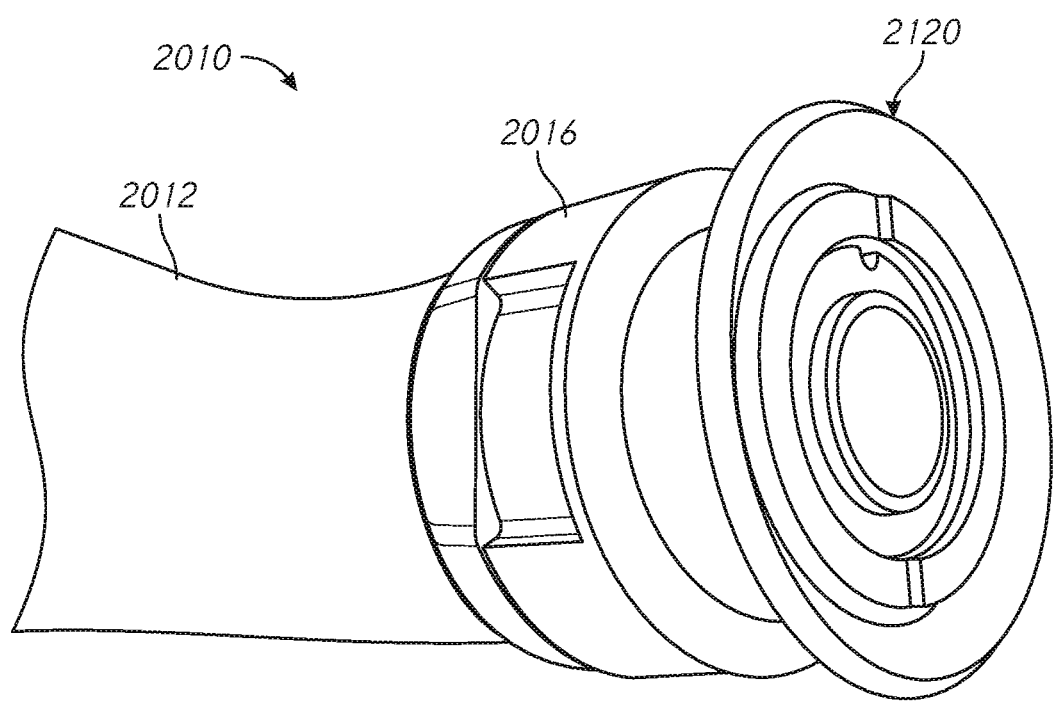
FIG. 9 illustrates a frontal perspective view of another embodiment of an engagement member or shroud positioned along the distal end of a handpiece assembly.

With continued reference to FIG. 5, the engagement member 2020 can comprises one, two or more (e.g., 3, 4, 5, more than 5, etc.) bellows or other collapsible members 2028. As noted herein, the bellows or other collapsible members can be configured to accommodate for a particular degree of irregularity along the distal end (e.g., along the end that is configured to contact and engage a subject's tissue, such as a scalp or face). In some embodiments, however, as illustrated in FIG. 9, the engagement member 2120 does not comprise any bellows or other collapsible members. Further, the engagement member or shroud 2020 can be configured to provide a desired level of rotation between the adjacent main body portion 2012 of the handpiece 2010 during use. In other words, in some arrangements, depending on the length and flexibility of the engagement member 2020, the engagement member 2020 can permit angles between 0 and 70 degrees (e.g., 0-10, 10-20, 20-30, 30-40, 40-50, 50-60, 60-70 degrees, angles between the foregoing ranges, etc.) between the longitudinal axis of the main body portion 12 and an axis perpendicular to the skin surface being treated (and thus, a plane forming the distal end of the engagement member), when the handpiece assembly is in use.

Figure 6:
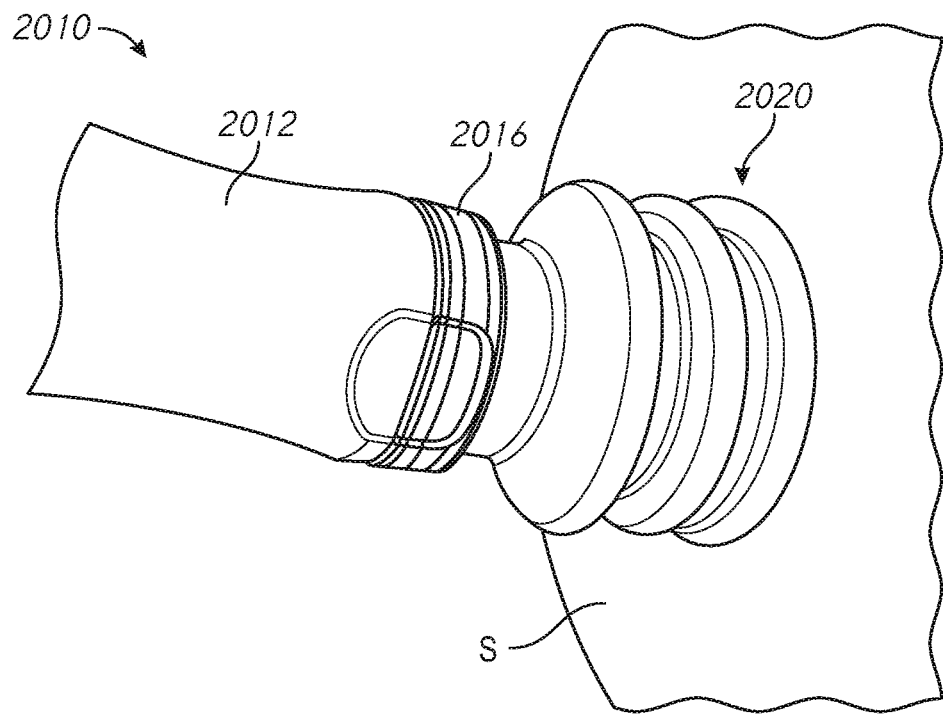
FIGS. 6 and 7 illustrate the embodiment of FIG. 5 in two different orientations during a skin treatment procedure.
Figure 7:
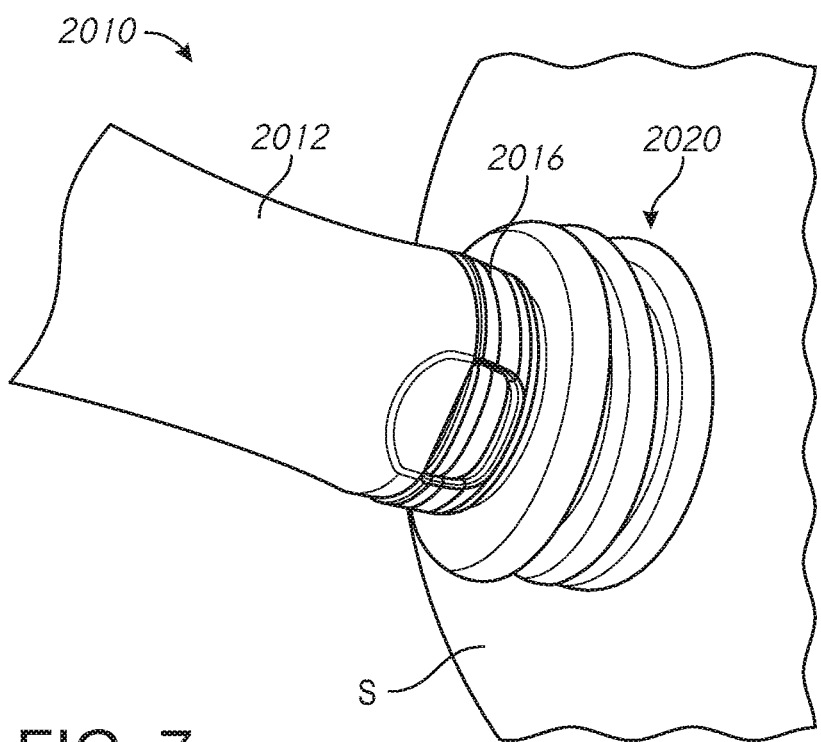

FIGS. 6 and 7 illustrate an embodiment of a handpiece assembly comprising an engagement member or a shroud 2020 being in use. Specifically, these figures show the engagement member 2020 during two different stages of operation for a handpiece assembly 2010 that is configured to provide a pulsed stream of fluid (e.g., air) to the distal end and to also provide a vacuum or suction force to the distal end. As depicted in FIG. 6, the engagement member or shroud 2020 is in a normal state, wherein its bellows 2028 are in an expanded configuration. In FIG. 7, the bellows 2028 are compressed or collapsed relative to each other. As discussed herein, such a collapse can be as a result of a vacuum force delivered to the interior space defined by the engagement member 2020, due to the user pushing or urging the handpiece assembly 2010 toward the targeted skin surface S (e.g., the scalp or face of a subject) and/or due to any other reason. According to some embodiments, the engagement member or shroud 2020, due to, e.g., the bellows, the use of flexible materials and/or the like, can be configured to collapse by 20 to 80% (e.g., 20-30, 30-40, 40-50, 50-60, 60-70, 70-80%, percentages between the foregoing, etc.) of its normal expanded length during use, as desired or required.

According to some embodiments, the engagement member or shroud 2020 can be configured to attach to existing handpiece tips. However, in other embodiments, the engagement member 2020 is configured to be provided together with the tip or is configured to be provided with the main body portion of a handpiece assembly (e.g., such that the handpiece assembly and the engagement member 2020 form a unitary or monolithic structure). Regardless of its exact configuration and incorporation into the handpiece assembly, the distal engagement member or shroud 2020 can advantageously compensate for and adapt to variations in the shape of a person's scalp (or other targeted skin surface, e.g., facial regions) and for variations in targeted skin surface shapes between individuals being treated.

As discussed herein, in the embodiment illustrated in FIG. 5, the engagement member 2020 can be a separate component that attaches (e.g., fixedly or removably) to a tip 2016. In other arrangements, however, the tip 2016 can be manufactured with the engagement member or shroud 2020, such that the tip 2016 is configured to form a unitary or monolithic structure with the engagement member 2020. The engagement member or shroud 2020 can be positioned or otherwise secured to any tips disclosed herein, including tips that are described and illustrated in applications that are incorporated by reference herein. For example, the engagement member can be coupled to tips that include both fluid delivery and suction ports, tips that include one or more abrasive structures (e.g., spiral members, posts, etc.) or abrasive surfaces, tips that are configured to provide air to the skin surface being treated (e.g., in a pulsed or non-pulsed manner) in addition to providing suction and fluid delivery to the skin surface, tips with or without needles, tips that include treatment materials (e.g., in solid, semi-solid, gel, other non-liquid forms, etc.) along the tip, such that water or other liquid delivered or otherwise present along the skin-tip interface will cause such treatment materials to dissolve and be released to the skin surface, etc. The tips from one or more of the following can be used together with an engagement member or shroud: U.S. patent application Ser. No. 12/346,582, filed Dec. 30, 2008 and issued on Jan. 1, 2013 as U.S. Pat. No. 8,343,116, U.S. patent application Ser. No. 11/392,348, filed Mar. 29, 2006 and issued on Nov. 1, 2011 as U.S. Pat. No. 8,048,089, U.S. patent application Ser. No. 12/832,663, filed Jul. 8, 2010 and issued on Aug. 26, 2014 as U.S. Pat. No. 8,814,836 and International Patent Application No. PCT/US2014/024992, filed Mar. 12, 2014 and published on Sep. 25, 2014 as PCT Publ. No. WO 2014/151104.

In embodiments where the engagement member or shroud 2020 is secured (e.g., fixedly or removably) to the tip (or directly to the main body portion or other component of the handpiece assembly), the engagement member or shroud 2020 can be secured using one or more attachment methods or devices. For example, the engagement member 2020 can be secured to the tip, main body portion and/or any other portion or component of the handpiece assembly 2010 using a press fit or friction fit connection, adhesives, a threaded connection, one or more fasteners, welding and/or the like, as desired or required.

As noted above, the attachment can comprise one or more soft, flexible materials (e.g., silicone rubber, foam, latex, vinyl, other types of rubbers and/or elastomeric materials, other natural and/or synthetic materials that are flexible, etc.) that are configured to conform to the surface of the scalp or other generally uneven or irregular skin surface being treated (e.g., facial skin tissue, neck, arms, legs, etc.). In some embodiments, the distal end of the engagement member or shroud 2020 is configured to form a seal between its peripheral member or portion and the adjacent targeted skin surface during use.

Figure 8:
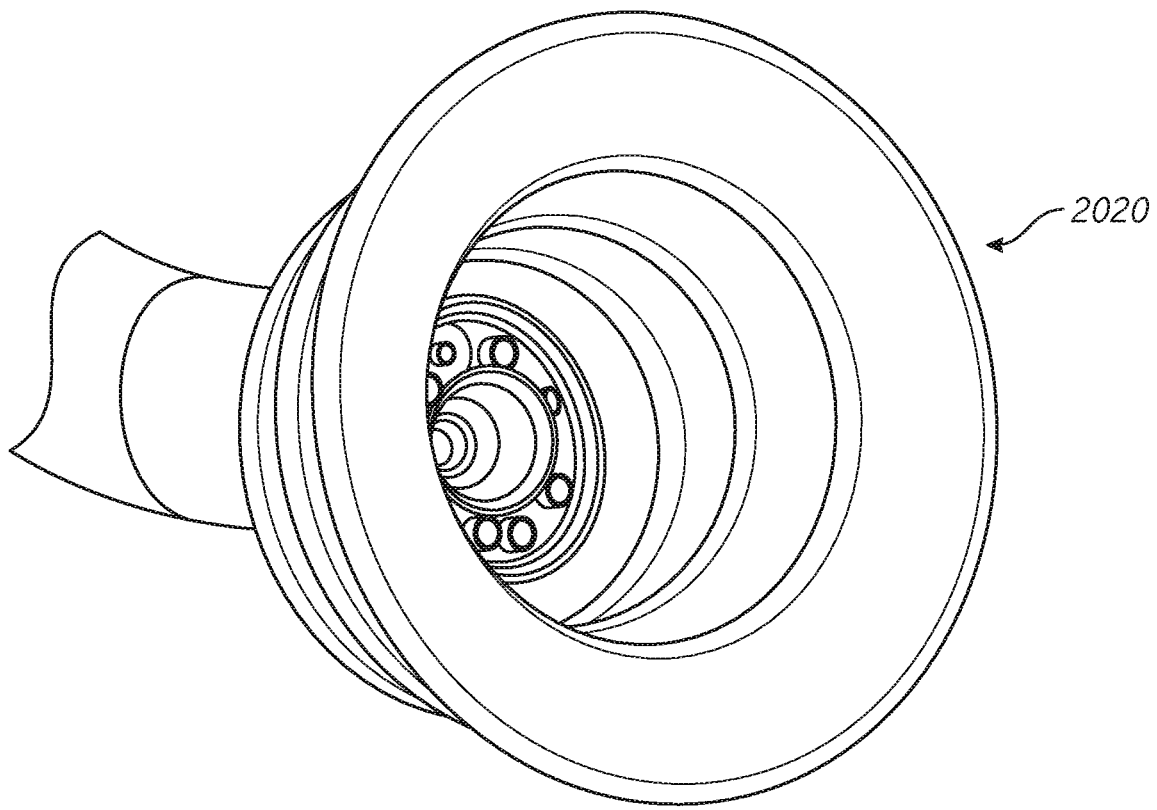
FIG. 8 illustrates a frontal perspective view of the engagement member and tip.

FIG. 8 illustrates an interior view of the engagement member or shroud 2020 that is secured to a tip configured to provide a suction force and fluid delivery to the tip, as well as a separate air stream to the tip (e.g., either in a pulsed or non-pulsed manner). For example, such tips are discussed in greater detail in U.S. Publ. No. 2014/0343574 (see, e.g., FIGS. 4 to 5C) and PCT Publ. WO/2014/151104 (see, e.g., FIGS. 4 to 5C and FIGS. 22A to 23E), both of which are incorporated by reference herein and made part of the present application.

In embodiments, such as the one illustrated in FIG. 8, the handpiece assembly is configured to provide fluid delivery (e.g., water, other serums and treatment materials, etc.) to the skin surface being treated, e.g., via one or more passages within and/or exterior to the main body portion and/or any other component of the assembly, as desired or required. As noted herein, the embodiment of FIG. 8 is also configured to provide a separate air stream that is configured to provide a force (e.g., continuously or intermittently) to the skin surface being treated. In some embodiments, such a stream of positive air pressure can facilitate the movement of fluids delivered or otherwise located along the skin surface being treated deeper into the tissue. Such techniques that help deliver fluids deeper into skin tissue can facilitate a skin treatment procedure and provide greater benefits to the subject being treated.

In embodiments, such as the one illustrated in FIG. 8, where a vacuum is created along the distal end of the handpiece assembly (e.g., and thus, at least partially within an interior of the engagement member or shroud 2020, the engagement member or shroud 2020 can be configured to constantly maintain a seal with adjacent tissue during use. For example, such a seal can be maintained despite the delivery of fluids to the skin surface, despite the delivery of a separate air stratum to the skin surface, despite the intermittent nature of the suction force created within the interior of the engagement member 2020 and/or despite any other factors or considerations. In other embodiments, however, the engagement member or shroud 2020 is configured to intermittently lose contact and lose the seal with the adjacent skin surface. Regardless of the exact manner in which the handpiece assembly, the engagement member or shroud 2020 and/or other components or features of the system are configured, the use of an engagement member or shroud 20 can facilitate making and maintaining contact with a variety of skin surfaces (e.g., irrespective of the irregularity of the skin surface). Relatedly, the engagement member 2020 can facilitate capturing and removing fluid from the skin surface being treated, thereby providing for a neater, less messy procedure.

As noted above, the engagement member or shroud can be shorter (e.g., include fewer bellows or other collapsible members than the embodiment of FIG. 5, or include no bellows or collapsible members). Such an arrangement for the engagement member 2120 is illustrated in FIG. 9. In some embodiments, such an engagement member or shroud 2120 can be used where the irregularity of the targeted scalp or other skin surface is reduced (e.g., the skin surface is more planar). In some embodiments, a user may prefer to use a shorter engagement member or shroud 120, such as the one illustrated in FIG. 9, for one or more reasons, e.g., to provide more directed control of the handpiece assembly vis-à-vis the skin surface, to provide less clearance between the tip and the skin surface and/or for any other reason or purpose, as desired or required.

As noted above, the engagement member or shroud can be used with any type of tip and/or in any type of skin treatment procedure. For example, a handpiece assembly can be provided with an engagement member or shroud for use in a hair growth procedure. For example, the engagement member can facilitate the delivery of hair growth agents deeper into the scalp, either before, during or after one or more other hair growth procedures or steps (e.g., hair transplant delivery, needling, abrasion, etc.). For example, in some embodiments, the use of the engagement member or shroud can help drive one or more treatment materials or other components deeper into the scalp or other targeted surface. Such materials and/or other components, include, without limitation, amino acids, antioxidants, Minoxidil, other antihypertensive vasodilator agents, other hair growth-stimulating agents, other natural or synthetic hairgrowth materials, skin tightening agents, platelet-rich plasma (PRP), exfoliation agents, peptides, bleaching agents, anti-acne agents, human growth factors, cytokines, soluble collagen, antioxidants, matrix proteins, Epicatechin, Catechin and/or other phenols and/or other anti-oxidants, neurotoxins, serums, salicylic acid, other anti-acne acids and materials, microcapsules, capsules, other time-release products and substances, water (e.g., distilled, tap water, filtered, etc.), saline, other dilution agents, dilutants or dissolvents, vitamins, chemical exfoliation agents, lotions, soothing agents, brightening or lightening agents, peptides, peeling agents, acids, anesthetics, medicants, other non-active or active compounds, other fluids or materials, combination or mixtures thereof and/or any other substance from one or more internal/external fluid sources.

However, the use of a handpiece assembly with a distal engagement member or shroud 2020, 2120 can be used in any other skin treatment procedures besides those targeting hair growth. For example, engagement member-equipped handpiece assemblies can be used for basic skin abrasion procedures (e.g., dermabrasion, with or without fluid delivery), acne, skin lightening, skin tightening, anti-aging, oily skin, lip repair/plumping, damaged skin, blackhead/sebum removal or extraction and/or the like.

Delivery of Hair Growth Treatment Agents with Other Steps or Procedures

As noted herein, the delivery of hair growth agents to and into a subject's skin can be facilitated and/or supplemented by one or more additional steps or procedures. Such steps or procedures can be performed or used before, during and/or after the delivery of fluids and/or other treatment materials to the targeted skin surface, as desired or required.

In some arrangements, for example, treatment fluids and/or other materials (e.g., amino acids, antioxidants, Minoxidil, other antihypertensive vasodilator agents, other hair growth-stimulating agents, other natural or synthetic materials and/or the like) are delivered to the targeted skin surface where hair growth is desired prior to, during and/or after exfoliation of skin. In some configurations, the fluids and/or other materials are delivered to the skin via a handpiece assembly (e.g., with the assistance of vacuum or suction to deliver one or more treatment fluids and/or other materials toward the tip or distal end of the handpiece assembly). The tip or distal end of the handpiece assembly can be configured to selectively abrade or exfoliate skin. For example, one or more abrading structures or features (e.g., spiral members, posts, other protruding members, abrasive discs or abrasive surfaces, diamonds, etc.) can be positioned along a tip or another portion along a distal end of the handpiece assembly. In some embodiments, as the handpiece assembly is moved relative to the targeted skin tissue, such abrading structures or features can selectively abrade or exfoliate skin tissue. As noted, the abrasion or exfoliation can facilitate the delivery of treatment fluids and/or other materials that are configured to promote hair growth deeper into the skin tissue, thereby enhancing the treatment procedure and increasing the likelihood that the treatment fluids and/or other materials will help to accomplish hair growth and/or other benefits related to hair health (e.g., strengthening hair, improving follicle viability, etc.).

Additional details regarding devices, systems and methods of skin abrasion and/or exfoliation are disclosed in U.S. patent application Ser. No. 12/346,582, filed Dec. 30, 2008 and issued on Jan. 1, 2013 as U.S. Pat. No. 8,343,116, U.S. patent application Ser. No. 11/392,348, filed Mar. 29, 2006 and issued on Nov. 1, 2011 as U.S. Pat. No. 8,048,089, U.S. patent application Ser. No. 12/832,663, filed Jul. 8, 2010 and issued on Aug. 26, 2014 as U.S. Pat. No. 8,814,836 and International Patent Application No. PCT/US2014/024992, filed Mar. 12, 2014 and published on Sep. 25, 2014 as PCT Publ. No. WO 2014/151104, the entireties of which are incorporated by reference herein.

The delivery of hair growth agents to a targeted skin surface accompanied by abrasion or exfoliation can comprise a multi-step (e.g., two-step process, three-step, more than three-step, etc.) process. For example, in some embodiments, a first step of the process comprises abrading and/or exfoliating skin tissue. During and/or following such abrading and/or exfoliation step, as noted above, one or more treatment fluids and/or other materials (e.g., amino acids, antioxidants, Minoxidil, other antihypertensive vasodilator agents, other hair growth-stimulating agents, other natural or synthetic materials and/or the like) can be advantageously delivered to the tissue. Such fluids and/or other materials can be configured to help promote skin growth.

According to some embodiments, as a follow-up step to abrasion/exfoliation and delivery of treatment fluids/other materials, one or more additional steps or procedures can be selectively performed. For instance, one or more light treatments can be performed on the targeted skin tissue to further help promote hair growth. Such light treatments can include, but are not necessarily limited to, the delivery of red (e.g., infrared) light, ultraviolet light and/or light of different frequencies and/or of different types, as desired or required. The delivery of light to skin can be beneficial for hair growth in one or more different ways. For example, light can be used to directly provide treatment to skin tissue. Alternatively, light can be used to activate or otherwise alter the function of a material that has been delivered to the skin. Embodiments of light-emitted wands that can be used in such procedures are discussed in greater detail below with reference to FIGS. 10A and 10B.

Figure 10B:
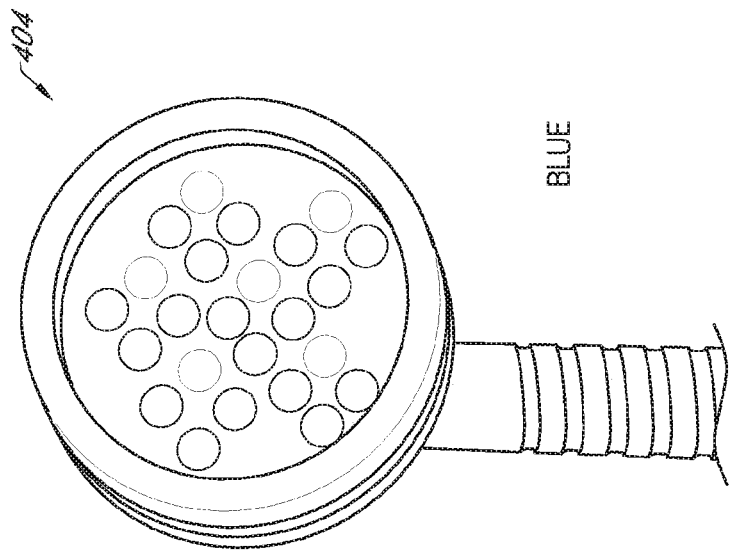
FIGS. 10A and 10B illustrate different embodiments of a light wand device configured for use with a hair growth and/or other skin treatment system.
Figure 10A:
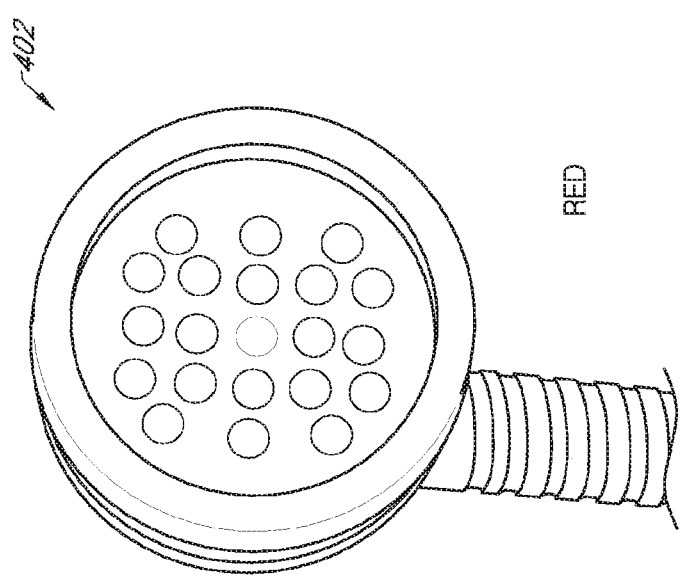

In some embodiments, one or more forms of light can be applied to the skin of the subject, before, during or after a hair growth or other skin treatment procedure. The type of light, its intensity, power, frequency, wavelength, duration of exposure and/or other properties can vary, as desired or required for a particular application or use. In some embodiments, one or more properties of the light source can be varied, during a procedure and/or between procedures. In some embodiments, as illustrated in FIGS. 10A and 10B, the light comprises one or more LEDs or other illumination sources. As with other modalities disclosed herein, the light can be incorporated or attached to a handpiece that is being used for microdermabrasion. However, in other embodiments, the light source is separate and distinct from a microdermabrasion handpiece assembly.

In some embodiments, two or more different types of light sources can be provided as options for the subject or the user performing a procedure on the subject. For example, with reference back to FIGS. 10A and 10B, one of the light wands 402 is configured to emit blue light (e.g., light having a wavelength of approximately 475 nm), while another light wand 404 is configured to emit red light (e.g., light having a wavelength of approximately 650 nm). In some embodiments, the application of light in the "red" wavelength range (e.g., 780 nanometer (nm) to 622 nm) can be helpful to hair stimulation and/or hair growth, either with or without one or more other treatment steps (e.g., delivery of fluids and/or other treatment materials to and/or within skin tissue, vacuum or positive air pressure, pulsing, needling, massaging, dermabrasion, other mechanical or other types of agitation, heating/cooling, etc.). One or more wands or other light sources can be provided having other target colors. Any other color or light can be emitted, as desired or required. For example, a single light wand can be selected that is adjustable so to select an exact wavelength of light (in addition to or in lieu of selecting intensity, power and/or any other properties).

One or more light sources can be incorporated directly or indirectly into any handpiece assembly disclosed herein that is configured to perform a hair growth treatment procedure. For example, an annular light can be positioned along or near (or embedded partially within) the lip at the distal tip of a handheld assembly (e.g., identical or similar to the ones discussed herein with reference to FIGS. 5 to 9). In other embodiments, the light can be removably mounted along an outside surface of the assembly.

In some embodiments, the use of light is configured to chemically or biochemically "activate" one or more treatment fluids and/or other substances have been or are being delivered to the skin surface of the subject. The activation of certain substances can provide one or more therapeutic or otherwise beneficial results. In other embodiments, the use of red, blue and/or other light can provide one or more direct benefits to the targeted skin tissue. In some embodiments, for example, red or blue light therapy can be used to complement the promotion of hair growth.

In some embodiments, light can be used to heat and/or at least partially modify or affect (e.g., at the cellular level) skin and adjacent tissue of the subject. For example, heat-producing or heat-inducing light source can be directed at the skin for a specific time period, before, during or after a skin treatment procedure (e.g., hair growth procedure with or without microdermabrasion or skin agitation). Light sources can include bulbs (e.g., incandescent, fluorescent, low-pressure sodium, high-intensity discharge, etc.), LEDs, lasers and/or the like. As discussed in greater detail below, heating of the skin can provide one or more benefits to the subject. For example, heating of skin tissue can enable the pores of the subject to open or dilate (e.g., allowing serums and/or other treatment fluids or substances to penetrate deeper into the skin surface). Heating of the skin can also increase blood circulation in the adjacent vessels (e.g., to help improve healing and recovery following a treatment procedure).

Additional details regarding light treatment are provided in International Patent Application No. PCT/US2014/024992, filed Mar. 12, 2014 and published on Sep. 25, 2014 as PCT Publ. No. WO 2014/151104, the entirety of which is incorporated by reference herein.

According to some embodiments, light treatment comprises treatment with light (e.g., using a light therapy handpiece or other device or system) that is configured to emit light at a wavelength of 610 to 650 nanometer (nm), e.g., in the "red" range. In other embodiments, light treatment comprises treatment with light that is configured to emit light at a wavelength of 800 to 1,050 nm, e.g., in the infrared range. In other embodiments, light treatment comprises treatment with light that is configured to emit light at a wavelength of 410 to 425 nm, e.g., in the "blue" range. In some embodiments, the power of the light provided to skin tissue can be 40 to 120 Joules/per $cm^2$. (e.g., 40-50, 50-60, 60-70, 70-80, 80-90, 90-100, 100-110, 110-120 Joules/$cm^2$, power levels between the foregoing, levels below 40 Joules/$cm^2$ or levels above 120 Joules/$cm^2$, as desired or required.

In any light treatment embodiments, light can be emitted using any source or configuration, including, without limitation, one or more LEDs. In some embodiments, emitted light (at one or more frequencies, wavelengths, power levels, etc.) can be selectively provided to skin to promote hair growth and/or hair stimulation, either alone or in combination with one or more treatment steps. The use of light can also assist skin in one or more other ways, such as helping with acne, anti-aging, wrinkles and/or the like.

One or more additional treatment steps and/or devices can be incorporated into a particular treatment procedure, as desired or required. For example, one or more of the following can be used to further enhance the likelihood of hair growth resulting from a particular treatment procedure, either in lieu of or in addition to skin abrasion/exfoliation and/or light treatment: other energy delivery (e.g., radiofrequency (RF) energy, microwave energy, ultrasound energy, laser, iontophoresis, etc.), thermal conditioning (e.g., cooling and/or heating of tissue before, during and/or after one or more other steps of a procedure), mechanical agitation, massaging and/or the like.

In some embodiments, in order to enhance a hair growth procedure, heat transfer can be provided to the targeted scalp or other skin surface. For example, as discussed above, the use of selective light delivery can help provide heat to a targeted skin surface. Heat transfer can comprise either heating or cooling, depending on the desired therapeutic effect, protocol and/or the like. Embodiments of separate handheld devices that are configured to heat or cool a targeted skin surface are discussed below with reference to FIGS. 11A and 11B.

In some arrangements, exposing the skin to hot and/or cold temperature can assist with various aspects associated with hair growth and/or other skin treatment techniques and procedures. For example, as discussed herein, heating skin can open the skin's pores, thereby allowing serums, other treatment fluids or materials and/or the like to enhance penetration and migration of such materials into the skin. Further, cooling the skin can cause pores to close, at least partially, allowing therapeutic fluids and/or other materials that previously entered the pores to stay within the skin for a longer time period.

Figure 11A:
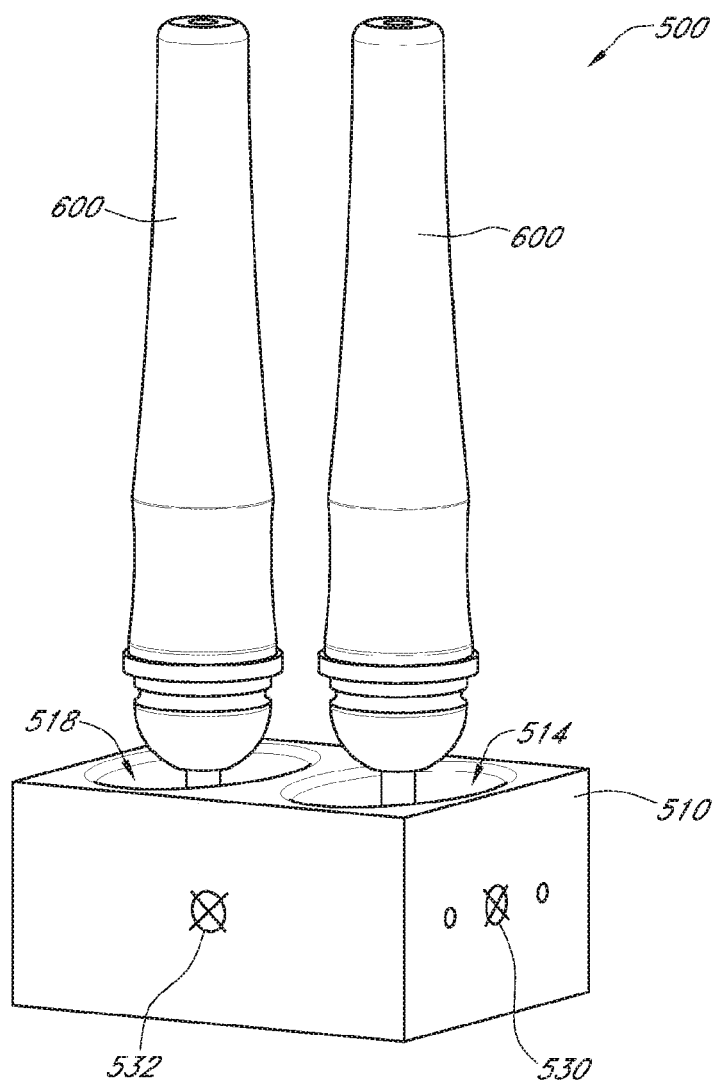
FIGS. 11A and 11B illustrate a station for a thermal conditioning system according to one embodiment.
Figure 11B:
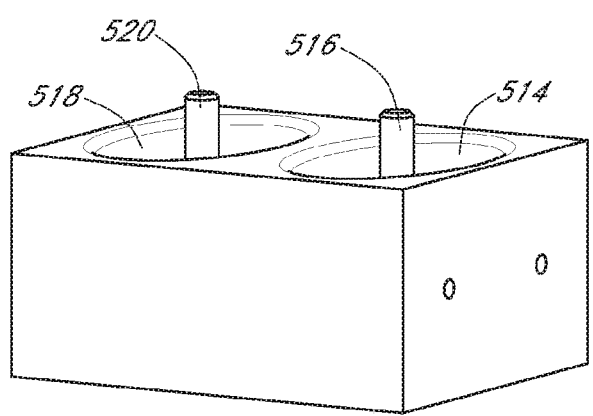

In some embodiments, one or more devices (e.g., handheld devices) can be used to conductively cool and/or heat skin, before, during and/or after a skin treatment procedure (e.g., hair growth promotion procedure). One embodiment of such a heating and cooling system is illustrated in FIGS. 11A and 11B. As shown, the system can include a thermal docking station 510. In some embodiments, the docking station 510 comprises one or more wells, ports or openings 514, 518 for receiving and thermally recharging thermal conditioning handheld assemblies 600.

With continued reference to FIGS. 11A and 11B, the thermal recharging station 510 can be in thermal communication with one or more heating and/or cooling devices (not shown). In some embodiments, one or more thermoelectric devices (e.g., Peltier devices) are positioned along the outside, the inside and/or within the walls of the station 510. However, any other type of heating and/or cooling device can be used. In some embodiments, thermal conditioning devices are positioned along the exterior surfaces of the docking station walls (e.g., as schematically represented by circles 530, 532 in FIG. 11A). Regardless of the quantity, type, location, spacing, orientation and/or configuration of the thermal conditioning devices, the devices can be adapted to conductively heat or cool adjacent portions of the station 510, including the wells 514, 518 that receive the thermal handpiece assemblies 600.

In some embodiments, the station comprises one or more thermally conductive materials, such as, for example, aluminum, copper, other metal or alloys. As illustrated in FIG. 11B, one or more of the wells 514, 518 can include a pin, rod or other protruding member 516, 520. As discussed in greater detail below, the thermal conditioning handheld assemblies 600 can include a central opening. In some embodiments, the assemblies 600 are generally hollow along their centerlines. Accordingly, the assemblies 600 can be conveniently mounted or otherwise positioned on the pins 516, 520 when being placed within the wells 514, 518 of the station 510. Therefore, as illustrated in FIG. 11A, the pins 516, 520 can securely maintain the thermal handheld assemblies in a generally vertical orientation when the assemblies are positioned within the station 510 for thermal recharging.

When the thermoelectric devices and/or other heating and/or cooling devices of the station are activated, the wells of the station can be heated or cooled, in accordance with the desired thermal conditioning effect of that station 510. In some embodiments, if thermoelectric devices are used to heat or cool the station 510, an additional station (not shown) can be positioned on the opposite surface of the thermoelectric device so that the additional station also undergoes heating or cooling (e.g., the opposite thermal effect of the main station).

The assembly 600 can comprise an inner core and an outer housing or shell. In some embodiments, the inner core comprises copper, aluminum and/or any other high heat transfer material (e.g., beryllium, other metals or alloys, etc.). In some embodiments, the copper and/or other material can be coated (e.g., plated) with one or more layers of nickel, chrome and/or the like. The outer housing can include ABS, Nylon and/or any other plastic or other material with a relatively low thermal conductivity (e.g., to avoid excessively or uncomfortably hot or cold temperatures being felt by a user who grasps and handles the assembly 600).

According to some embodiments, the thermal handheld assembly 600 includes an interior lumen or opening that extends completely or partially through the assembly. The proximal end of the assembly 600 can be placed in fluid communication with a vacuum conduit, if the assembly will be configured for suction. In such arrangements, the conduit is placed in fluid communication with a vacuum or negative pressure source. In some embodiments, however, the heating or cooling system is configured to be used without suction.

The handheld assembly 600 can comprise a distal head. In the illustrated embodiment, the head includes a circular or rounded outer shape, having a generally smooth surface. In some embodiments, the head comprises one or more openings that are in fluid communication with the internal lumen or passage of the assembly 600. In some embodiments, the head forms a unitary structure with and is part of the core of the assembly 600. As such, it advantageously comprises one or more high heat transfer materials (e.g., copper) that can be heated or cooled relatively quickly when placed within a well of the station 510.

Regardless of their exact shape, size, configuration and/or other properties, the thermal handheld assemblies 600 can be used to selectively heat or cool a subject's skin surface. As noted above, in one embodiment, the surface to be treated (e.g., scalp, other skin surface where hair growth is desired, etc.) can first be heated to open the skin pores and/or provide one or more other benefits. With the pores open, a fluid delivery process can be performed, either with or without skin abrasion. Accordingly, any hair growth serums, other treatment fluids and/or other substances that are delivered to the working end of a skin treatment device (e.g., along the skin surface that was previously heated), could pass deeper and/or with greater ease into the open pores of the skin. Following the treatment protocol (e.g., fluid delivery only, fluid delivery with dermabrasion, etc.), the user can use a cold thermal conditioning assembly 600 to cool the skin surface that was treated. As a result of cooling the skin surface, the pores of the skin can at least partially close, thereby trapping the potentially beneficial serums and/or other components within the skin. Such a treatment method can provide for a quicker recovery time, fewer complications and/or one or more other benefits or advantages.

According to some embodiments, the level of heating or cooling of the thermal assemblies 600 can be adjusted and controlled (e.g., by modifying the duty cycle of the thermoelectric devices or any other heating or cooling device that is thermally conditioning the station 510). In some embodiments, a thermostat and/or other temperature detection is used to ensure that the operating temperature of the station 510 and the handheld assemblies that the station is configured to heat do not reach dangerous or uncomfortable extremes.

In other embodiments, a skin surface can be heated or cooled using any other method or device. For example, skin can be heated using any of the energy or other modalities discussed herein (e.g., RF, ultrasound, microwave, etc.). In one embodiment, the liquids, serums and/or other treatment fluids delivered to the tip of a microdermabrasion device (e.g., from a vial or cartridge, a bottle of a manifold or tower system, etc.) can be heated or cooled before it reaches the skin surface. Therefore, one or more heating or cooling devices can be incorporated into the microdermabrasion handheld device or the fluid system that is coupled to the handheld device.

Rollerball/Porous Assemblies for Fluid/Treatment Material Delivery

In some embodiments, the various treatment devices, systems and/or methods disclosed herein can be used together with alternative handheld assemblies and/or other devices or systems to help deliver hair growth fluids and/or other materials to a targeted skin region (e.g., a subject's scalp surface). Examples of such devices and systems are discussed below with reference to FIGS. 12A-15.

Figure 12A:
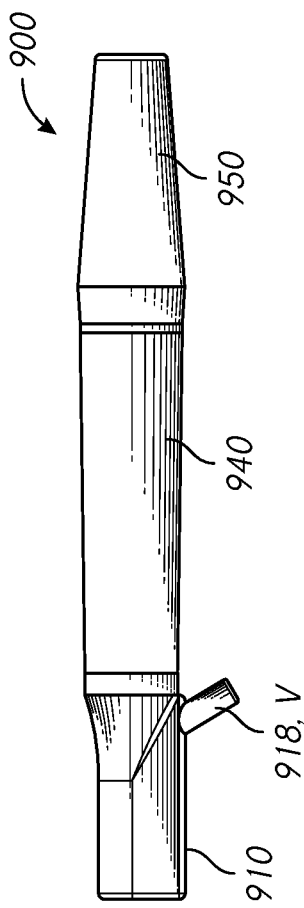
FIGS. 12A and 12B illustrate different views of an assembly comprising a rollerball for use with a treatment system according to one embodiment.
Figure 12B:
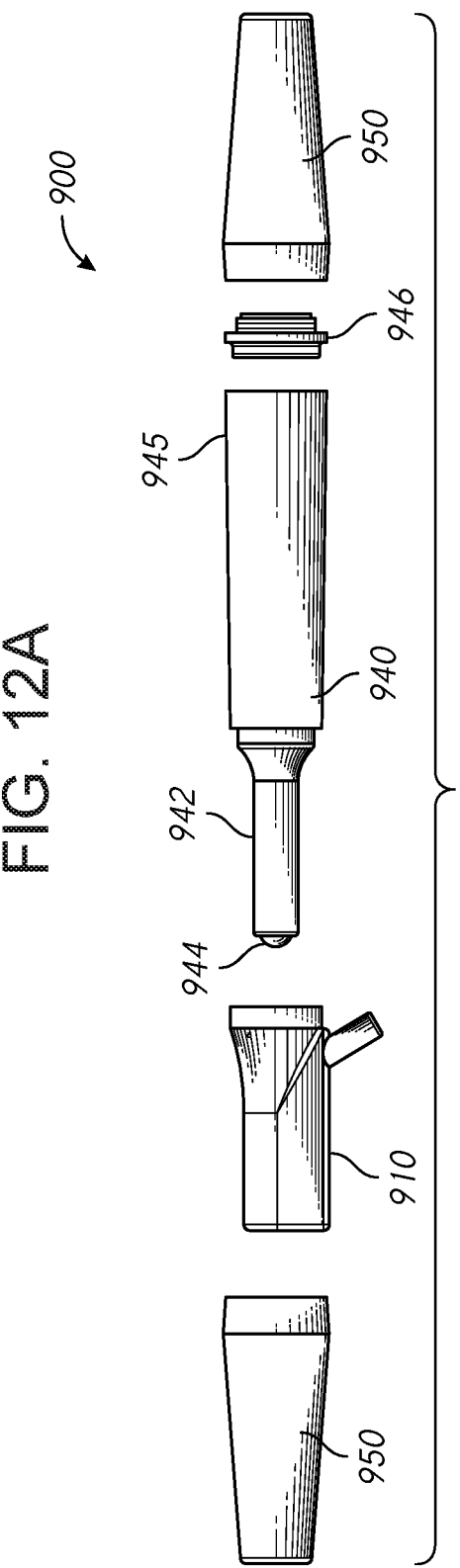

One embodiment of an assembly 900 comprising a rollerball and configured to be used for hair growth procedures is illustrated in FIGS. 12A and 12B. The depicted assembly 900 includes a handpiece and a tip that are integrated into a single unitary or monolithic structure 910. In some embodiments, such a combined handpiece and tip can be configured to be disposable so it is replaced between uses. According to some embodiments, the assembly 900 comprises a cartridge or other fluid source 940 that is configured to secure to the combination handpiece/tip 910.

With continued reference to FIG. 12B, the distal end 942 of the cartridge 940 can include a rollerball 944 that is routed through an interior portion of the combination handpiece/tip 910 when the cartridge 940 is positioned therein. In some embodiments, the rollerball 944 extends to or near the distal end of the combination handpiece/tip 910 when the assembly 900 is ready for use. Accordingly, as the assembly 900 is moved relative to a subject's skin surface (e.g. scalp), the rollerball can at least partially contact the skin surface being treated and rotate. Rotation of the rollerball 944 can facilitate the transfer of fluid and/or other contents of the cartridge 940 to the distal end of the combination handpiece/tip 910, and thus, the skin surface.

As shown in FIGS. 12A and 12B, the proximal end 945 of the cartridge 940 can include a closure member 946 that sealingly encloses an interior of the cartridge 940. Thus, in some embodiments, the interior of the cartridge 940 can be opened, refilled and closed. However, in other arrangements, the cartridge 940 is configured to remain sealed at all times. Thus, is such configurations, the cartridges are disposable after use. The above disclosure regarding cartridges that can be opened and cartridges that are configured to remain sealed can be applied to any of the assembly arrangements disclosed herein or variations thereof.

In some embodiments, the cartridge 940 included in the assembly 900 of FIGS. 12A and 12B can be re-used between sequential treatment procedures (e.g., hair growth treatments). For example, once the subject has completed a particular treatment session, the subject can be permitted to take home any used cartridge or cartridges (to the extent two or more different serums or other treatment materials were used). Thus, the subject can bring the unused cartridges to a subsequent treatment session, thereby eliminating waste and reducing the overall expense of a procedure. In some embodiments, the subject can be instructed to apply one or more of the serums and/or other materials contained within the corresponding unused cartridges 940 to his or her scalp or other skin between office visits. Accordingly, in order to prevent contamination of the cartridges and their internal contents, to prevent evaporation, leaks or other loss of the internal contents of the cartridges, to otherwise protect the cartridges (e.g., the rollerball 944 located along the cartridge's distal end) and/or to provide one or more additional benefits or advantages, a cap 950 can be used to protect the distal end 942 of a cartridge between uses. The rollerball 944 can facilitate the application of fluid to the subject's scalp or other skin surface where hair growth is desired between office visits. For example, the use of a rollerball can advantageously permit fluid to be delivered from the interior of the cartridge 940 to the subject's skin surface without the use of suction or a handpiece. Thus, the overall effectiveness of a hair growth and/or other skin treatment procedure can be advantageously enhanced by such embodiments.

In some embodiments, for example, two or more main hair growth serums or materials can be used during a treatment procedure. Thus, during a first visit to a professional, the subject undergoes a two-step treatment procedure in which a first formulation is first applied to the subject's skin surface (e.g., with or without the application of vacuum). As a follow-up step, a second serum or other fluid or material is applied to the skin. In some embodiments, as discussed herein, the user is then provided with cartridges or other fluid containers. Such cartridges can be advantageously returned to the professional for conducting a follow-up procedure during a subsequent visit. In addition, the subject can be instructed, in accordance with certain protocols, to periodically apply one or more of these serums or fluids to his or her skin between visits, as desired or required.

As noted herein, the combination handpiece/tip 910 included in the assembly of FIGS. 12A and 12B can be disposable between uses or sequential procedures. Thus, the use of such a disposable portion can reduce the likelihood of the transfer of contamination between subjects and/or procedures, thereby improving the overall hygiene and safety of skin treatment procedures.

With continued reference to FIGS. 12A and 12B, the combination handpiece/tip 910 can include a suction port or conduit 918 that is configured to be placed in fluid communication with a vacuum source. In the illustrated embodiment, suction port 918 extends along an exterior of the handpiece/tip component 910 (e.g., at an angle); however, in other arrangements, the suction port or conduit 918 can extend, at least partially or completely, within an interior of the assembly 900, as desired or required. In yet other embodiments, the assembly 900 is not configured to be placed in fluid communication with a suction or vacuum source. Accordingly, in such arrangements, the assembly need not have any suction or vacuum ports, passages, conduits and/or other related components or features.

In any of the embodiments disclosed herein, a rollerball or similar feature along the distal end of a cartridge, handpiece and/or tip can be replaced with one or more other features that to help to selectively deliver fluid to the skin surface being treated (e.g., from a reservoir of a cartridge or other container placed in fluid communication with the system). For example, as illustrated in the embodiment of FIG. 13, the rollerball can be replaced with a wicking or other fluidly porous member 1044 along its distal end.

With reference to FIG. 13, the distal end 1042 of the cartridge 1040 can include a wicking member 1044. In some embodiments, the rollerball 944 extends to or near the distal end of the combination handpiece/tip when the assembly is ready for use. Accordingly, as the assembly is moved relative to a subject's skin surface (e.g., scalp, other skin region where hair growth is desired, etc.), the wicking member 1044 can at least partially contact the skin surface being treated and deliver fluid from the fluid reservoir of the cartridge or other container 1040 to the skin surface. The wicking member 1044 can comprise one or more porous materials or features, such as, for example, foam, a porous stone, sponge or other member, another material or member comprising a porous or otherwise open or semi-open structure. In some embodiments, the wicking or other porous member 1044 can be saturated with the particular fluids contained within the reservoir of the cartridge or other container member. Thus, the wicking member 1044 can retain the necessary moisture level to selectively deliver fluid to the skin surface treated, even when the level of fluid within the cartridge or the other container 1040 is relatively low.

With continued reference to FIG. 13, the wicking member 1044 can comprise one or more foams, thermoplastics and/or other materials. The cross-sectional size of the wicking member can be between ¼ inch and 2 inches. In some embodiments, the wicking member 1044 extends, at least partially, within the interior reservoir of the cartridge or other container. The wicking member 1044 can include any cross-sectional shape, as desired or required, such as, for example, circular, oval, square or other rectangular, other polygonal (e.g., triangular, pentagonal, hexagonal, octagonal, decagonal, etc.), irregular.

Figure 14:
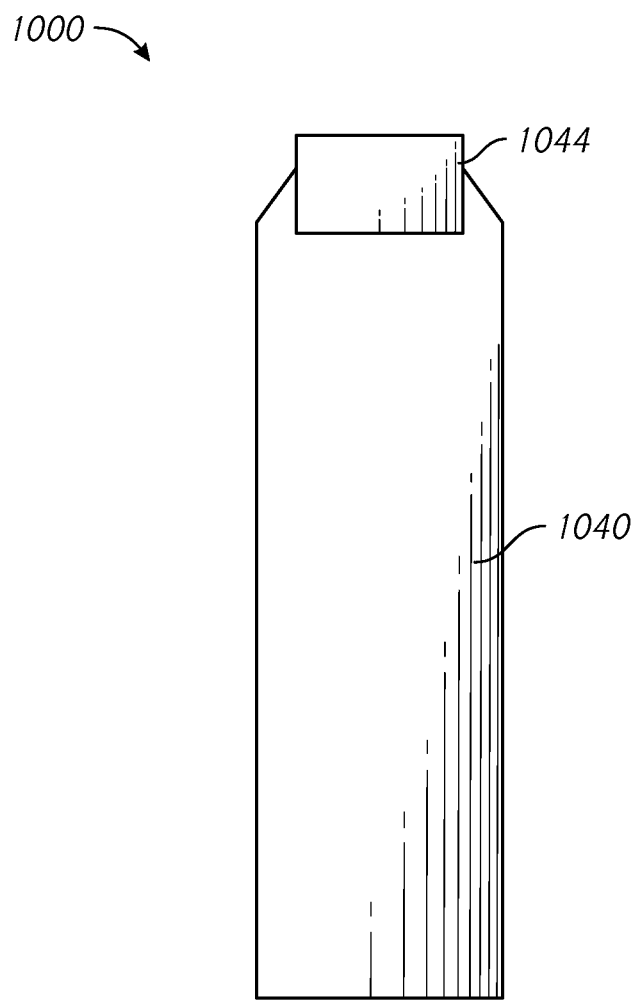
FIG. 14 schematically illustrates a side view of an assembly comprising a wicking or porous member for use with a treatment system according to one embodiment.

FIG. 14 schematically illustrates a skin treatment system 1000 similar to the system depicted in FIG. 13. As shown, the system 1000 can include a cartridge or other container 1040 comprising a wicking or other porous structure 1044 along its distal end. The wicking or other porous structure can include one or more materials that are configured to at least partially absorb, adsorb and/or otherwise retain a volume of liquid or other material. As discussed herein, according to some embodiments, such a wicking structure 1044 can be used to keep the distal end of the cartridge 1040 at least partially moist for purposes of delivering fluids and/or other materials to the subject's scalp and/or other skin surface during a particular procedure (e.g., a hair growth procedure).

According to some embodiments, the wicking or other porous structure 1044 incorporated into any of the embodiments herein (e.g., the distal end of a cartridge or other container, the handpiece, the tip, etc.) can be used for one or more purposes. For example, in some embodiments, the wicking material can be used to perform one or more of the following functions: (i) to store one or more materials within a portion of a skin treatment assembly (e.g., along a distal end of a cartridge, along a tip of an assembly, along a handpiece, etc.); (ii) as a filter (e.g., for waste debris leaving the skin surface being treated); (iii) for delivering fluids and/or other materials to the skin surface being treated; and/or the like. For example, in one embodiment, a wicking or other porous material 1044 can include a treatment material (e.g., as a liquid, gel, powder, etc.). Water or another dilution agent can then be delivered to or near the wicking or porous member 1040 to selectively release the materials stored within the wicking or other porous member.

Figure 15:
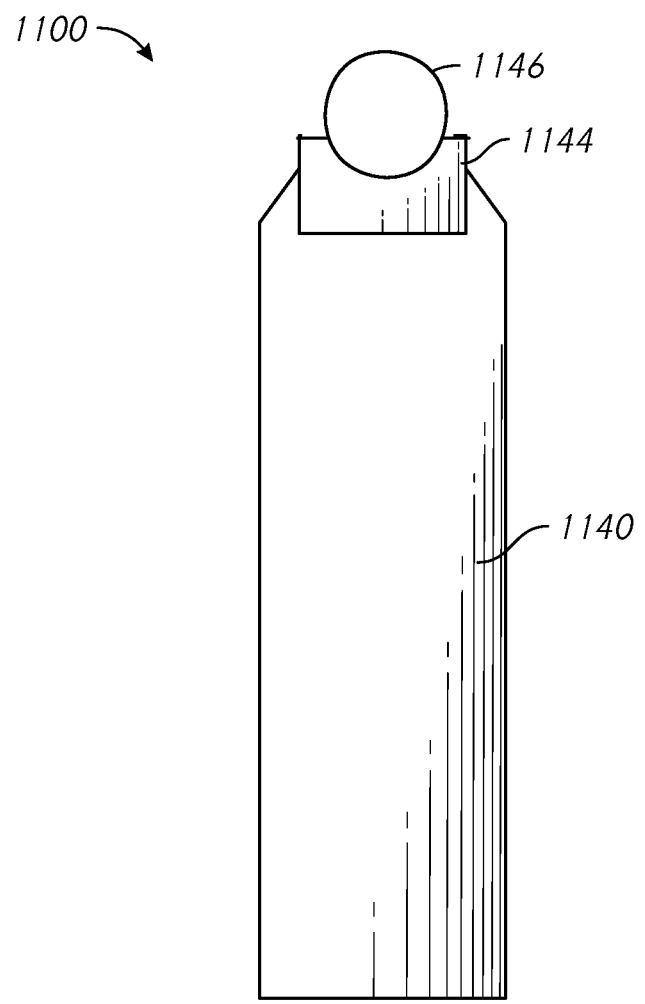
FIG. 15 schematically illustrates a side view of an assembly comprising a wicking or porous member and a rollerball for use with a treatment system according to one embodiment.

According to some embodiments, as schematically illustrated in FIG. 15, a rollerball or other movable member 1146 can be positioned along the distal end of a wicking or other porous member or structure 1144. In such a system 1100, the wicking member 1144 and rollerball 1146 can be positioned along the distal end of a cartridge 1140. Alternatively, as with other configurations disclosed herein, the wicking member 1144 and/or the rollerball 1146 (or combination thereof) can be located along the handpiece, the tip and/or any other location of the skin treatment assembly. In such embodiments, the rollerball 1146 can be kept in fluid communication with the fluid contained within the cartridge or other container with the assistance of the wicking member or structure. In other words, the proximal end of the rollerball can be advantageously maintained moist with the assistance of the wicking material.

Additional details regarding the use of rollerballs, wicking members and/or other porous structures to deliver treatment fluids and/or other materials to the scalp or other targeted skin surface of a subject are provided in International Patent Application No. PCT/US2015/067531, filed Dec. 22, 2015 and published on Jun. 30, 2016 as PCT Publ. No. WO 2016/067531, the entirety of which is incorporated by reference herein.

Implants/Transplants

In some embodiments, the various treatment devices, systems and/or methods disclosed herein can be used together with hair implants to further enhance a hair growth or hair supplementation procedure. For example, the delivery of certain fluids and/or other materials to a targeted skin surface, the use of exfoliation or abrasion steps, the delivery of light (e.g., infrared, ultraviolet, etc.), the use of laser, the use of other energy modalities and/or the like can be used to supplement a hair implant or hair transplant procedure. The use of the various technologies described herein (or referenced herein), or variations thereof, can further improve the likelihood of success for a hair implant or hair transplant procedure. By way of example, the selective delivery of growth factors (e.g., especially in light of the ability to drive or push such growth factors deeper into a portion of targeted tissue) can bolster the health and viability of adjacent or surrounding hair implants.

Massaging/Other Tip Details

In some embodiments, the targeted skin surface (e.g., scalp, other skin area where hair growth is desired, etc.) can be massaged or otherwise manipulated in conjunction with a hair growth procedure or protocol. For example, in some arrangements, the scalp or other targeted skin surface is massaged prior to and/or during the delivery of one or more fluids, agents and/or other materials. The messaging and/or other agitation of the scalp or other targeted skin tissue of the subject can be accomplished manually and/or using a device or system. For example, in some embodiments, massaging of skin tissue can be accomplished using a handpiece assembly (e.g., similar to any of the assemblies disclosed herein, such as, for example, those illustrated in FIGS. 1 to 15). In some embodiments, a massaging tip (e.g., a tip that is removably or permanently attached to the distal end or tip of the handpiece assembly) can be used to create the desired or required massaging or agitation action. For instance, the tip can include one or more undulations or other features (e.g., recesses, protrusions, etc.) that, when moved against the adjacent skin tissue, can massage such skin tissue. Such massaging action can be accomplished together with or in lieu of abrasion, as desired or required. In some embodiments, massaging of skin tissue can provide one or more therapeutic benefits related to hair growth. The massaging can help stimulate certain anatomical reactions that may assist with hair growth. In some arrangements, massaging can help drive or move any treatment fluids or other materials deeper into the scalp or other targeted tissue.

In other embodiments, tips or other distal portions of a handpiece assembly used in hair growth procedures can have include one or more desired materials on or within their structure. As discussed in greater detail herein, one or more materials can be strategically embedded, impregnated, placed, stored and/or otherwise disposed on one or more surfaces or areas of the tip or other portion or component of the skin treatment system. Such materials can comprise solids, semi-solids, other dried substances, gels, concentrated solutions and/or the like. For example, such materials can be provided in loose form (e.g., positioned on or within a recess, other portion of the tip, within a cartridge or other container, adhered to one or more surfaces, etc.), as a tablet, capsule, pill, disc or other dissolvable solid, saturated within a foam pad or other sponge-like material and/or the like. Thus, in certain arrangements, water (e.g., distilled, tap water, filtered, etc.), saline, other dilutants and/or other fluids which are delivered to the tip can selectively dissolve, liquefy, melt, soften, dilute or otherwise prepare the materials embedded, impregnated and/or otherwise positioned on the tip, within a cartridge or other container and/or on or within another portion or component of a skin treatment system (e.g., handpiece assembly, fluid line upstream of the handpiece assembly, etc.). Accordingly, any desired hair growth materials or formulations can be advantageously provided to the skin surface being treated, as desired or required. Such materials can include, without limitation, one or more of the following: growth factors (e.g., human-derived, non-human derived, liposome (courier) chemically altered growth factors, etc.), amino acids (e.g., leucine, isoleucine, valine, etc.), antioxidants, minoxidil, other anti-hypertensive vasodilators, finasteride, dutasteride, ketoconazole, spironolactone, flutamide, catechin, epicatechin, other phytochemicals, carnitine, rejuvaplex, copper peptides, other hair growth-stimulating agents, other pharmaceuticals and non-pharmaceuticals, plant-derived products, cleansing or pre-cleansing shampoos, other cleansing or pre-cleansing solutions (e.g., salicylic acid, GlySal™ (glycolic acid and salicylic acid mix), other acids, etc.), and other natural and synthetic materials.

According to some embodiments, one or more treatment materials can be applied to the targeted skin tissue (e.g., scalp) using dabbing the skin tissue (e.g., manually) with one or more treatment materials. Such dabbing action can be accomplished by contacting and/or moving a tip or other discharge portion of a fluid container (e.g., bottle, vial, etc.) relative to the targeted tissue. In other embodiments, an applicator (e.g., swab, fabric, other porous or absorbent member, etc.) can be used to deliver the fluid to the skin tissue, as desired or required. Any other device or method can also be used to deliver fluid and/or other treatment material to the skin surface, including, without limitation, spraying, misting, brush, roller, other dispenser and/or the like.

Needling

In some embodiments, needles may be used to help the passage of one or more treatment fluids and/or other materials deeper into skin tissue. For example, the use of needles can create passages within the targeted skin tissue to permit growth factors and/or other fluids or materials to be delivered deeper into the skin. Relatedly, such configurations can also assist in promoting the passage of treatment fluids and/or other materials closer to any hair follicles (e.g. including any follicles that result from a hair implant or transplant procedure). The use of needling or similar procedure that assists with the passage of fluids and/or other materials through the skin can be used alone or in conjunction with one or more techniques (e.g., abrasion, exfoliation, energy delivery, laser, light treatment, pulsing, other mechanical agitation, thermal treatment, etc.), as desired or required. For example, needling can include the use of a reciprocating needling assembly identical or similar to the one discussed herein with reference to FIGS. 4A-4E. Additional details regarding needling are provided in International Patent Application No. PCT/US2014/024992, filed Mar. 12, 2014 and published on Sep. 25, 2014 as PCT Publ. No. WO 2014/151104, the entirety of which is incorporated by reference herein.

With respect to needling embodiments, a needling step can be used in advance of and/or after the delivery of growth factors and/or other fluids or materials that are configured to promote hair growth or stability. In some embodiments, the needles or other members that are used to at least partially penetrate skin can be coated and/or otherwise configured to comprise one or more treatment fluids and/or other materials (e.g., growth factors). Such coated needles can be solid or hollow, as desired or required for a particular application or use. For example, such factors and/or other materials can be disposed along one or more surfaces (e.g., exposed surfaces) of the needles. In other embodiments, the various treatment materials can be located along interior cavities (e.g., interior of the needles, other recesses along or near the needles, and/or the like) of the corresponding handpiece assembly or other device or system. In some embodiments, such materials can be provided on or near the needles in a solid, semi-sold, gel, granular and/or other non-liquid form. In such configuration, the various materials positioned on, along and/or near the needles or similar members can be configured to at least partially dissolve for release onto a targeted skin surface. The use of the embodiments can further enhance the delivery of growth factors and/or other materials deeper into skin tissue to help promote hair growth and/or hair strengthening.

In other embodiments, needles are at least partially hollow to permit the delivery of fluids and/or other treatment materials (e.g., growth factors) therethrough. The use of such configurations can assist with the efficient and selective delivery of precise amounts of growth factors and/or other materials to and into the targeted skin tissue surface. For example, in some arrangements, the hollow portions of the needles are in fluid communication with a reservoir to allow the user to delivery one or more fluids and/or other materials at a desired flowrate, in accordance with a particular application, protocol or treatment procedure.

In any needle embodiments discussed herein, or alternatives thereof, needles that are used as part of a treatment procedure can be coated with one or more treatment materials. As noted above, treatment materials can include, without limitation, one or more of the following: growth factors (e.g., human-derived, non-human derived, liposome (courier) chemically altered growth factors, etc.), amino acids (e.g., leucine, isoleucine, valine, etc.), antioxidants, minoxidil, other antihypertensive vasodilators, finasteride, dutasteride, ketoconazole, spironolactone, flutamide, catechin, epicatechin, other phytochemicals, carnitine, rejuvaplex, copper peptides, other hair growth-stimulating agents, other pharmaceuticals and non-pharmaceuticals, plant-derived products, cleansing or pre-cleansing shampoos, other cleansing or pre-cleansing solutions (e.g., salicylic acid, GlySal™ (glycolic acid and salicylic acid mix), other acids, etc.), other natural and synthetic materials and/or the like. Such treatment materials can be coated onto the needles (e.g., completely or at least partially), otherwise deposited on the needles and/or the like. In some embodiments, such materials can be provided as a gel, solid, semi-solid and/or another form that can be dissolved or otherwise released in the presence of water, saline and/or another liquid.

Massaging/Undulating Embodiments for Enhanced Infusion

In some embodiments, a tip or other distal portion of a treatment device or system (e.g., handpiece assembly or something to secure to or near the distal end of a handpiece assembly) is configured to massage or otherwise manipulate the skin tissue being contacted without necessarily abrading skin tissue. For example, in some embodiments, the tip or other distal portion of a handpiece assembly can include non-linear or undulating portion(s) and/or feature(s) that are configured to provide mechanical agitation (e.g., with or without abrasion or exfoliation) when the handpiece assembly or other device or system is moved relative to said skin surface. In some embodiments, such massaging or pressure-inducing feature(s) and/or other configuration(s) can help open pores and/or otherwise facilities the penetration of treatment materials that are delivered to the skin deeper into the skin. This can enhance a treatment procedure, as the treatment materials can be "driven" or moved deeper into the skin tissue (e.g., closer to the follicle roots, closer to deeper portions of skin tissue, etc.) to further promote hair growth/stimulation, scape or skin health and/or the like.

Scalp Health/Other Indications

In some embodiments, the same or similar procedures described herein, or equivalents thereof, can be used to treat other ailments or conditions related to skin or hair. For example, in some embodiments, the procedures can be used to improve the health of a subject's scalp or other skin surface, to help treat or otherwise improve a subject's conditions related to dandruff, psoriasis, seborrheic dermatitis and/or the like.

To assist in the description of the disclosed embodiments, words such as upward, upper, bottom, downward, lower, rear, front, vertical, horizontal, upstream, downstream have been used above to describe different embodiments and/or the accompanying figures. It will be appreciated, however, that the different embodiments, whether illustrated or not, can be located and oriented in a variety of desired positions.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combine with or substituted for one another in order to form varying modes of the disclosed inventions. Thus, it is intended that the scope of the present inventions herein disclosed should not be limited by the particular disclosed embodiments described above, but should be determined only by a fair reading of the claims that follow.

While the inventions are susceptible to various modifications, and alternative forms, specific examples thereof have been shown in the drawings and are herein described in detail. It should be understood, however, that the inventions are not to be limited to the particular forms or methods disclosed, but, to the contrary, the inventions are to cover all modifications, equivalents, and alternatives falling within the spirit and scope of the various embodiments described and the appended claims. Any methods disclosed herein need not be performed in the order recited. The methods summarized above and set forth in further detail below describe certain actions taken by a practitioner; however, it should be understood that they can also include the instruction of those actions by another party. The methods summarized above and set forth in further detail below describe certain actions taken by a user (e.g., a professional in some instances); however, it should be understood that they can also include the instruction of those actions by another party. Thus, actions such as "moving a handpiece" or "delivering a fluid" include "instructing moving a handpiece" and "instructing delivering a fluid." The ranges disclosed herein also encompass any and all overlap, sub-ranges, and combinations thereof. Language such as "up to," "at least," "greater than," "less than," "between," and the like includes the number recited. Numbers proceeded by a term such as "about" or "approximately" include the recited numbers. For example, "about 10 mm" includes "10 mm." Terms or phrases preceded by a term such as "substantially" include the recited term or phrase. For example, "substantially parallel" includes "parallel."

What is claimed is:

1. A method of promoting hair growth or hair stimulation in a subject, the method comprising:
    abrading skin tissue of the subject by moving a handpiece assembly along a targeted portion of the subject's skin surface where hair growth or hair stimulation is desired;
    wherein abrading skin tissue comprises moving the handpiece assembly relative to the targeted portion of the subject's skin surface, the handpiece assembly comprising at least one abrading structure or feature along a distal end of the handpiece assembly, wherein the at least one abrading structure or feature is positioned within an area defined by a peripheral lip and is stationary relative to the peripheral lip, the peripheral lip being configured to contact the targeted portion of the subject's skin surface, wherein the peripheral lip is separate and distinct from the at least one abrading structure or feature;
    wherein the at least one abrading structure or feature has a height that is less than a height of the peripheral lip, such that the an end of the peripheral lip is more distal than an end of the at least one abrading structure or feature;
    applying vacuum or suction using the handpiece assembly along the targeted portion of the subject's skin surface; and
    providing at least one treatment material to said targeted portion of the subject's skin surface, wherein the at least one treatment material is drawn to the distal end of the handpiece assembly using the vacuum or suction that is applied along the targeted portion of the subject's skin surface;
    wherein abrading skin tissue is configured to facilitate a delivery of at least a portion of the at least one treatment material into the subject's skin tissue; and
    wherein the application of vacuum or suction helps promote hair growth or stimulate hair.

2. The method of claim 1, wherein the vacuum or suction is applied continuously or intermittently.

3. The method of claim 2, wherein the vacuum or suction is applied intermittently.

4. The method of claim 3, wherein an intermittent application of vacuum or suction is configured to create alternating first and second pressure along the subject's skin surface, wherein the first pressure is greater than the second pressure, and wherein the second pressure is a vacuum or suction.

5. The method of claim 4, wherein the first pressure is a vacuum or suction.

6. The method of claim 1, wherein at least a volume of the at least one treatment material is provided to the subject's skin (i) manually via hand application or dabbing or (ii) via the handpiece assembly.

7. The method of claim 1, wherein the distal end of the handpiece assembly comprises a tip.

8. The method of claim 7, wherein the tip is removable from a proximal portion of the handpiece assembly.

9. The method of claim 7, wherein the tip comprises at least one suction port or opening through which vacuum or suction is selectively applied.

10. The method of claim 1, wherein the at least one treatment material comprises one or more of the following: growth factors, leucine, isoleucine, valine, other amino acids, antioxidants, minoxidil, other antihypertensive vasodilators, finasteride, dutasteride, ketoconazole, spironolactone, flutamide, catechin, epicatechin, other phytochemicals, carnitine, rejuvaplex, copper peptides, other hair growth-stimulating agents, other pharmaceuticals and non-pharmaceuticals, plant-derived products, cleansing or pre-cleansing shampoos, salicylic acid, a glycolic acid and salicylic acid mix, other acids, other cleansing or pre-cleansing solutions, and other natural and synthetic materials.

11. A method of promoting hair growth or hair stimulation in a subject, the method comprising:
    abrading skin tissue of the subject by moving a handpiece assembly along a targeted portion of the subject's skin surface where hair growth or hair stimulation is desired;
    wherein abrading skin tissue comprises moving the handpiece assembly relative to the targeted portion of the subject's skin surface, the handpiece assembly comprising at least one abrading structure or feature along a distal end of the handpiece assembly, wherein the at least one abrading structure or feature is positioned within an area defined by a peripheral lip, the peripheral lip being configured to contact the targeted portion of the subject's skin surface, wherein the peripheral lip is separate and distinct from the at least one abrading structure or feature;
    wherein the at least one abrading structure or feature is stationary relative to the peripheral lip;
    applying vacuum along a targeted portion of the subject's skin surface where hair growth or hair stimulation is desired; and
    providing at least one treatment material to said targeted portion of the subject's skin surface, wherein the at least one treatment material is drawn to the distal end of the handpiece assembly using the vacuum that is applied along the targeted portion of the subject's skin surface;

wherein abrading skin tissue is configured to facilitate a delivery of at least a portion of the at least one treatment material into the subject's skin tissue; and wherein the application of vacuum helps promote hair growth or stimulate hair.

12. The method of claim 11, wherein the vacuum is applied continuously.

13. The method of claim 11, wherein the vacuum is applied intermittently.

14. The method of claim 13, wherein an intermittent application of vacuum is configured to create alternating first and second pressure along the subject's skin surface, wherein the first pressure is greater than the second pressure, and wherein the second pressure is a vacuum or suction.

15. The method of claim 11, wherein at least a volume of the at least one treatment material is provided to the subject's skin (i) manually via hand application or dabbing or (ii) via a handpiece assembly.

16. The method of claim 11, wherein the at least one treatment material comprises one or more of the following: growth factors, leucine, isoleucine, valine, other amino acids, antioxidants, minoxidil, other antihypertensive vasodilators, finasteride, dutasteride, ketoconazole, spironolactone, flutamide, catechin, epicatechin, other phytochemicals, carnitine, rejuvaplex, copper peptides, other hair growth-stimulating agents, other pharmaceuticals and non-pharmaceuticals, plant-derived products, cleansing or pre-cleansing shampoos, salicylic acid, a glycolic acid and salicylic acid mix, other acids, other cleansing or pre-cleansing solutions, and other natural and synthetic materials.

17. The method of claim 11, wherein the distal end of the handpiece assembly comprises a tip.

18. The method of claim 17, wherein the tip is removable from a distal portion of the handpiece assembly.

19. The method of claim 17, wherein the tip comprises at least one suction port or opening through which vacuum or suction is selectively applied.

* * * * *